United States Patent
Schmidt et al.

(10) Patent No.: US 9,751,847 B2
(45) Date of Patent: Sep. 5, 2017

(54) METHODS AND COMPOSITIONS RELATED TO NEUROACTIVE THIAZOLINE COMPOUNDS

(75) Inventors: Eric W. Schmidt, Salt Lake City, UT (US); Zhenjian Lin, Salt Lake City, UT (US); Rowena R. Antemano, Manila (PH); Alan Light, Park City, UT (US); Baldomero M. Olivera, Salt Lake City, UT (US); Gisela P. Concepcion, Quezen (PH)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 13/878,189

(22) PCT Filed: Oct. 14, 2011

(86) PCT No.: PCT/US2011/056299
§ 371 (c)(1),
(2), (4) Date: Sep. 25, 2013

(87) PCT Pub. No.: WO2012/051502
PCT Pub. Date: Apr. 19, 2012

(65) Prior Publication Data
US 2014/0018400 A1    Jan. 16, 2014

Related U.S. Application Data

(60) Provisional application No. 61/393,346, filed on Oct. 14, 2010.

(51) Int. Cl.
*A61K 31/427* (2006.01)
*A61K 31/425* (2006.01)
(Continued)

(52) U.S. Cl.
CPC .......... *C07D 277/10* (2013.01); *A61K 31/421* (2013.01); *A61K 31/426* (2013.01);
(Continued)

(58) Field of Classification Search
USPC ..................................................... 514/369
See application file for complete search history.

(56) References Cited

U.S. PATENT DOCUMENTS

| 5,457,101 A | 10/1995 | Greenwood | 514/220 |
| 5,952,331 A | 9/1999 | Berger | 514/256 |

(Continued)

FOREIGN PATENT DOCUMENTS

| CA | 2 694 270 | * | 2/2009 |
| JP | 48-8099 | * | 3/1973 |

(Continued)

OTHER PUBLICATIONS

English translation of JP 48-8099.*
(Continued)

*Primary Examiner* — San-Ming Hui
(74) *Attorney, Agent, or Firm* — Ballard Spahr LLP

(57) ABSTRACT

In one aspect, the invention relates to compounds having a general structure: and methods of using same to modulate calcium release. This abstract is intended as a scanning tool for purposes of searching in the particular art and is not intended to be limiting of the present invention.

24 Claims, 36 Drawing Sheets

(51) Int. Cl.
| | |
|---|---|
| C07D 277/10 | (2006.01) |
| A61K 31/421 | (2006.01) |
| A61K 31/426 | (2006.01) |
| A61K 45/06 | (2006.01) |
| C07D 277/12 | (2006.01) |

(52) U.S. Cl.
CPC ............ *A61K 31/427* (2013.01); *A61K 45/06* (2013.01); *C07D 277/12* (2013.01)

(56) References Cited

U.S. PATENT DOCUMENTS

| | | | | |
|---|---|---|---|---|
| 5,990,133 | A | 11/1999 | Gaster | 514/337 |
| 6,444,477 | B1 | 9/2002 | Borman | 436/503 |
| 7,396,943 | B2 | 7/2008 | Benesh | 549/29 |
| 2002/0035057 | A1 | 3/2002 | Richter | 514/1 |
| 2003/0027128 | A1 | 2/2003 | Borman | 435/4 |
| 2003/0166672 | A1 | 9/2003 | Lubbert | 514/297 |
| 2010/0152241 | A1 | 6/2010 | Whitten | 514/326 |

FOREIGN PATENT DOCUMENTS

| | | | |
|---|---|---|---|
| WO | WO 96/24351 | | 8/1996 |
| WO | WO 97/35578 | | 10/1997 |
| WO | WO2004/017959 | * | 3/2004 |
| WO | WO 2008/073929 | | 6/2008 |
| WO | PCT/US2011/056299 | | 10/2011 |
| WO | WO/2012/051502 | | 4/2012 |

OTHER PUBLICATIONS

U.S. Appl. No. 61/393,346, filed Oct. 14, 2010, Eric W. Schmidt.
Aira Z, et al. (2010) Subtype-specific changes in 5-HT receptor-mediated modulation of C fibre-evoked spinal field potentials are triggered by peripheral nerve injury. J. Neuroscience, 168: 831-841.
Almarasson O, et al. (2004) "Crystal Engineering of the Composition of Pharmaceutical Phases. Do Pharmaceutical Co-crystals Represent a New Path to Improved Medicines?" The Royal Society of Chemistry, 1889-1896.
Barradas MA, et al. (1994) Naftidrofuryl inhibits the release of 5-hydroxytryptamine and platelet-derived growth factor from human platelets. Clinica Chim Acta, 230:157-167.
Borman RA, et al. (1995) Functional evidence for a 5-HT$_{2B}$ receptor mediating contraction of longitudinal muscle in human small intestine. Brit J Pharmacol, 114:1525-1527.
Borman RA, et al. (1997) 5-HT$_{1D}$ and 5-HT$_{2B}$ receptors mediate contraction of smooth muscle in human small intestine. Ann NY Acad of Sci, 812:222-223.
Brea J, et al. (2010) Emerging opportunities and concerns for drug discovery at Serotonin 5-HT$_{2B}$ receptors. Curr Top Med Chem, 5: 493-503.
Bukovits GL, et al. (1982) Anorg Chem, Org Chem, 37B: 877-880.
Choi DS, et al. (1996) Immunohistochemical localisation of the serotonin 5-HT$_{2B}$ receptor in mouse gut, cardiovascular system, and brain. FEBS Lett 391: 45-51.
Christian EP, et al. (1989) Serotonin increases excitability of rabbit C-fiber neurons by two distinct mechanisms. J Applied Physiol, 67: 584-591.
Cockett AT, et al. (1993) Relationship of neuroendocrine cells of prostate and serotonin to benign prostatic hyperplasia. Urology, 42: 512-519.
Cox CD, et al. (1981) Pyochelin: novel structure of an iron-chelating growth promoter for Pseudomonas aeruginosa. Proc Natl Acad Sci U S A, 78: 4256-4260.
Crosa JH and Walsh CT. (2002) Genetics and assembly line enzymology of siderophore biosynthesis. Microbiol Mol Biol Rev, 66: 223-249.
Drechsel H, et al. (1995) Structure elucidation of yersiniabactin, a siderophore from highly virulent Yersinia strains. Liebigs Ann. 10: 1727-1733.

Gil-Turnes MS, et al. (1989) Symbiotic marine bacteria chemically defend crustacean embryos from a pathogenic fungus. Science, 246: 116-118.
Glusa E and Roos A. (1996) Endothelial 5-HT receptors mediate relation of porcine pulmonary arteries in response to ergotamine and dihdroergotamine. Brit J Pharmacol, 119: 330-334.
Glusa E, et al. (1993) Endothelium-dependent relaxation of procine pulmonary arteries via 5-HT$_{1C}$-like receptors. Naunyn—Schmied Arch Pharmacol 347: 471-477.
Govoni M, et al. (2003) Synthesis and pharmacological identification of neutral histamine H1-Receptor antagonists. Journal of Medicinal Chemistry, 46: 5812-5824.
Griffiths GL ,et al. (1984) Vibriobactin, a siderophore from Vibrio cholerae. J Biol Chem, 259: 383-385.
Hoyer D. (1989) 5-Hydroxytryptamine receptors and effector coupling mechainsm in peripheral tissues. In: The Peripheral Actions of 5-HT, Fozard J. (ed). Oxford University Press, Oxford, UK: 72-99.
James AL, et al. (1989) The mechanics of airway narrowing in asthma. Am Rev Respir Dis, 139: 242-246.
Kelleher MD, et al. (1995) Role of MAP kinase activation in bovine tracheal smooth muscle mitogenesis. Am J Physiol, 268(6 pt 1): L894-901.
Kennett GA. (1993) 5-HT$_{1C}$ receptors and their therapeutic relevance. Curr Opin Invest Drugs, 2:317-362.
Killam AL, et al. (1995) Role of alpha 1-adrenoceptors and 5-HT2 receptors in serotonin-induced contraction of rat prostate: autoradiographical and functional studies. Eur J Pharmacol, 273: 7-14.
Kobayashi S, et al. (1998) Micacocidin A, B, and C, novel antimycoplasma agents from *Pseudomonas* sp. I. Taxonomy, fermentation, isolation, physico-chemical properties and biological activities. J Antibiot, 51:323-327.
Kursar JD, et al. (1994) Molecular cloning, functional expression, and mRNA tissue distribution of the human 5-hydroxytryptamine$_{2B}$ receptor. Mol Pharmacol 46(2): 227-234.
Launay JM, et al. (1996) Ras involvement in signal transduction by serotonin 5-HT$_{2B}$ receptor. J Biol Chem, 271: 3141-3147.
Lechin F, et al. (1996) Increased levels of free serotonin in plasma of symptomatic asthmatic patients. Ann Allergy Asthma Immunol, 77:245-253.
Lee JC, et al. (2003) Improved production of teicoplanin using adsorbent resin in fermentations. Letters in Applied Microbiology, 27: 196-200.
Lee SL, et al. (1994) Serotonin produces both hyperplasia and hypertrophy of bovine pulmonary artery smooth muscle cells in culture. Am J Physiol, 266: L46-52.
Lee SL, et al. (1997) Association of Tyr phosphorylation of GTPase-activating protein with mitogenic action of serotonin. Am J Physiol, 272(1 pt 1): C223-230.
Len C, et al. (2005) Synthesis of diastereoisomeric pairs of novel analogues of d4T having an isochroman glycn moiety; their enzymatic kinetic resolution, their enantiopure synthesis, molecular modeling and NMR structural study. Tetrahedron, 61: 10583-10595.
Lessorf (1985) Scand J Gastroenterology, 109:117-121.
Li C, et al. (2010) Recent advances in thiopeptide antibiotic biosynthesis. Nat. Prod. Rep. 27: 153-164.
Light AR, et al. (2008) Dorsal root ganglion neurons innervating skeletal muscle respond to physiological combinations of protons, ATP, and lactate mediated by ASIC, P2X, and TRPV1. J Neurophysiol, 100: 1184-1201.
Margraf et al. (1991) Morphometric analysis of the lung in bronchopulmonary dysplasia. Am Review of Respiratory Disease, 143: 391-400.
Martin DJ, et al. (2002) Gabapentin-mediated inhibition of voltage-activated Ca2+ channel currents in cultured sensory neurones is dependent on culture conditions and channel subunit expression. Neuropharmacology, 42: 353-366.
Naegeli HU and Zaehner, H. (1980) Metabolites of microorganisms. Part 193. Helv. Chim. Acta, 63: 1400-1406.
Naturforsch B, et al. (1982) Anorg. Chem., Org. Chem., 37B: 877-880.
Nebigil et al. (2000) PNAS USA, 97: 22591-2596.

(56) References Cited

OTHER PUBLICATIONS

Noble AJ, et al. (1997) The effects of tamsulosin, a high affinity antagonist at functional α1A- and α1D-adrenoceptor subtypes. Brit J Pharmacol, 120: 231-238.
Pakala R, et al. (1994) Mitogenic effect of serotonin on vascular endothelial cells. Circulation, 90: 1919-1926.
Peraud O, et al. (2009) Microhabitats within venomous cone snails contain diverse Actinobacteria. Appl. Environ. Microbiol., 75: 6820-6826.
Piel J. (2004) Metabolites from symbiotic bacteria. J Nat Prod Rep, 21: 519-538.
Piel J. (2009) Metabolites from symbiotic bacteria. J Nat Prod Rep, 26: 338-362.
Richardson BP, et al. (1990) Serotonin and nociception Ann NY Acad Sci, 600: 511-520.
Sanger GJ, et al. (1996) 5-Hydroxytryptamine and functional bowel disorders. Neurogastroenterology and Motility, 8: 319-331.
Sasaki O, et al. (2002) Watasemycins A and B, new antibiotics produced by *Streptomyces* sp. TP-A0597. J Antibiot (Tokyo), 55: 249-255.
Schmidt EW, et al. (2008) Trading molecules and tracking targets in symbiotic interactions. Nat Chem Biol, 4: 466-473.
Sheehan JP, et al. (1997) Calcium homeostasis and reactive oxygen species production in cells transformed by mitochondria from individuals with sporadic Alzheimer's disease. Journal of Neuroscience, 17: 4612-4622.
Shindo K, et al. (1989) Thiazostatin A and thiazostatin B, new antioxidants produced by Streptomyces tolurosus. J Antibiot, 42: 1526-1529.
Sugimoto Y, et al. (1980) Chem Soc Jpn, 53: 3723-3724.
Symon DB, et al. (1995) Double blind placebo controlled trial of pizotifen syrup in the treatment of abdominal migraine. Arch Disease in Childhood, 72(1): 48-50.
Taguchi F, et al. (2010) The siderophore pyoverdine of Pseudomonas syringae pv. Tabaci 6605 is an intrinsic virulence factor in host tobacco infection. J Bacteriol, 192(1): 117-126.
Tanum L, et al. (1996) A new pharmacologic treatment of functional gastrointestinal disorder. A double-blind placebo-controlled study with mianserin. Scand J Gastroenterol, 31(4): 318-325.
Terlau H. (2004) Conus venoms: a rich source of novel ion channel-targeted peptides. M Physiol Rev, 84(1): 41-68.
Udwary DW, et al. (2007) Genome sequencing reveals complex secondary metabolome in the marine actinomycete Salinispora tropica. Proc Natl Acad Sci U S A , 104(25): 10376-10381.
Waterfield NR, et al. (2008) Rapid virulence annotation (RVA): identification of virulence factors using a bacterial genome library and multiple invertebrate hosts. Proc Natl Acad Sci U S A, 105: 15967-15972.
Watts SW, et al. (1996) The 5-hydroxytryptamine2B receptor and 5-HT receptor signal transduction in mesenteric arteries from deoxycorticosterone acetate-salt hypertensive rats. J Pharmacol Exp Ther, 277: 1103-13.
Watts SW, et al. (1995) 5-HydroxytryptaminesB receptor mediates contraction in the mesenteric artery of mineralocorticoid hypertensive rats. Hypertension, 26: 1056-1059.
Werth JL, et al. (1994) Mitochondria buffer physiological calcium loads in cultured rat dorsal root ganglion neurons. The Journal of Neuroscience, 14: 348-256.
Yamada Y, et al. (1970) The structure and synthesis of aeruginoic acid (2-o-hydroxy-phenylthiazole-4-carboxylic acid). Agr Biol Chem, 34(5): 780-783.
Yasuhara F and Yamaguchi S. (1977) Use of shift reagent with MTPA derivates in 1H NMR spectroscopy. III. Determination of absolute configuration and entiomeric purity of primary carbinols with chiral center at the C-2 position. Tetrahedron Lett., 47: 4085-4088.
You MX, et al. , (2008)-Q. Chinese J Chem, 26: 1332-1334.
Zamri A and Abdallah MA. (1999) An improved stereocontrolled synthesis of pyochellin, siderophone of Pseudomonas aeruginosa and Burkholderia cepacia. Tetrahedron, 56: 249-256.
Zunnundzhanov A, et al. (1987) K Khim Prir Soedin, 553-558.
Preliminary Amendment file Apr. 5, 2013 for U.S. Appl. No. 13/878,189, filed Sep. 25, 2013 (Inventors—Schmidt et al.) (3 pages).
Requirement for Restriction issued Jun. 20, 2014 for U.S. Appl. No. 13/878,189, filed Sep. 25, 2013 (Inventors—Schmidt et al.) (11 pages).
Written Opinion mailed on Mar. 9, 2012 for International Application No. PCT/US2011/056299 filed Oct. 14, 2011 and published as WO 2012/051502 on Apr. 19, 2012 (Inventors—Schmidt et al.) (7 pages).
International Search Report mailed on Mar. 9, 2012 for International Application No. PCT/US2011/056299 filed Oct. 14, 2011 and published as WO 2012/051502 on Apr. 19, 2012 (Inventors—Schmidt et al.) (3 pages).

\* cited by examiner

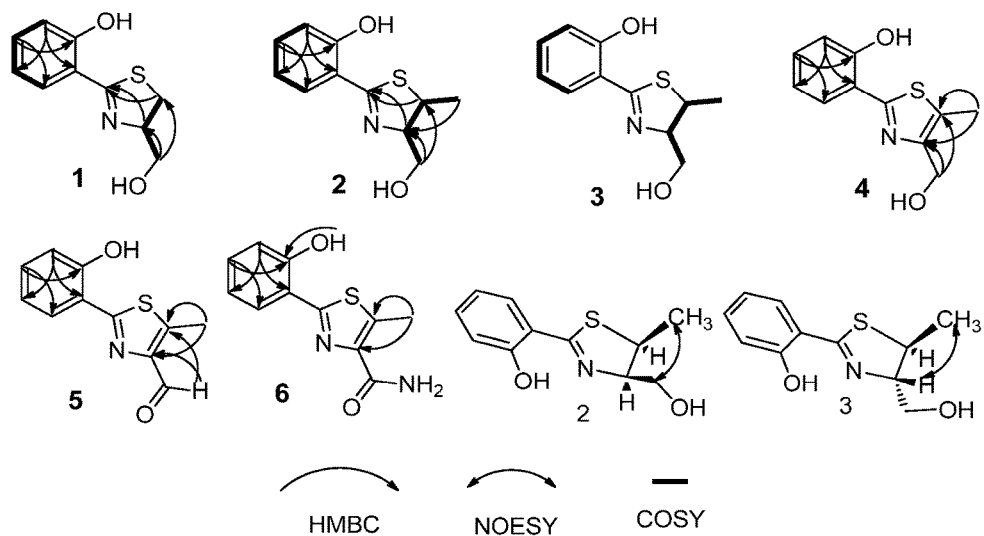
FIGURE 2
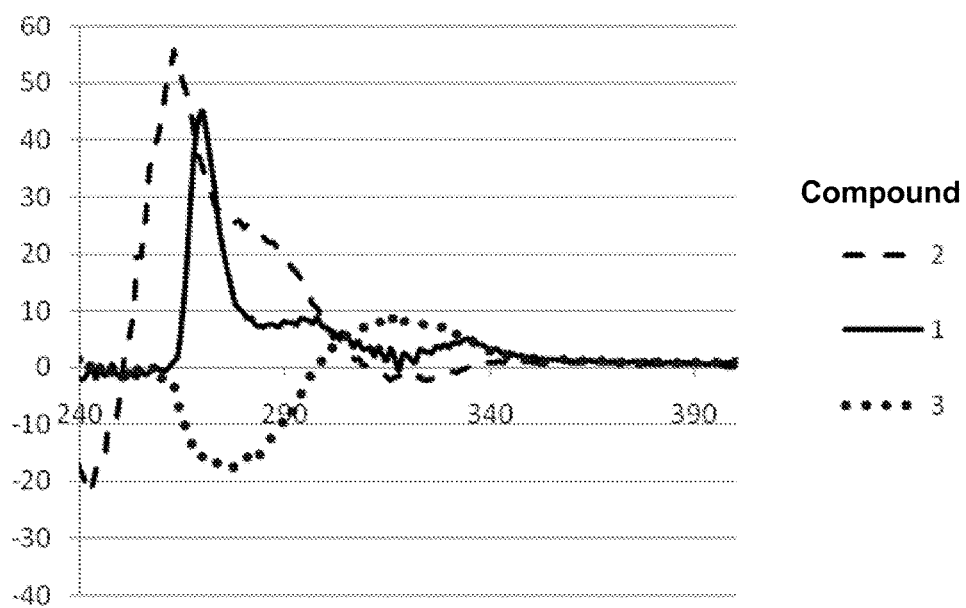

METHODS AND COMPOSITIONS RELATED TO NEUROACTIVE THIAZOLINE COMPOUNDS

CROSS-REFERENCE TO RELATED APPLICATIONS

This application is a National Phase Application of International Application No. PCT/US2011/056299, filed Oct. 14, 2011, which claims priority to U.S. Patent Application No. 61/393,346, filed Oct. 14, 2010, which applications are incorporated herein fully by this reference.

STATEMENT REGARDING FEDERALLY SPONSORED RESEARCH

This invention was made with government support under Grant No. U01 TW008163 awarded by the Fogarty International Center of the National Institutes of Health and under support provided by the National Institute of Mental Health's Psychoactive Drug Screening Program, Contact #HHSN-271-2008-00025-C (NIMH PDSP). The government has certain rights in the invention.

SUMMARY

In accordance with the purpose(s) of the invention, as embodied and broadly described herein, the invention, in one aspect, relates to compounds useful as modulators of calcium release, pharmaceutical compositions comprising same, and methods of treating disorders associated with modulation of calcium release.

Disclosed method for treating a disorder related to calcium release in a mammal, the method comprising the step of administering to the mammal an effective amount of least one compound having a structure represented by a formula:

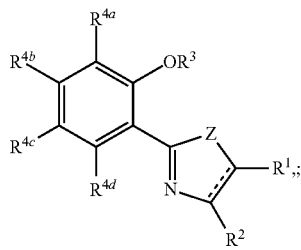

wherein ----- is an optional covalent bond, wherein valency is satisfied; wherein Z is selected from O and S; wherein $R^1$ is selected from hydrogen and optionally substituted C1-C6 alkyl; wherein $R^2$ is selected from nitrile, formyl, optionally substituted heteroaryl, optionally substituted heterocycloalkyl, optionally substituted alkoxyl, optionally substituted thioalkyl, optionally substituted alkylsulfonyl, optionally substituted alkylamino, thioamido, alkoxycarbonyl, carboxamide, amino-carbonyl, and alkylamine-carbonyl; wherein $R^3$ is selected from hydrogen and optionally substituted C1-C6 alkyl; wherein each of $R^{4a}$, $R^{4b}$, $R^{4c}$, and $R^{4d}$ is independently selected from hydrogen, halogen, hydroxyl, nitrile, nitro, thiol, formyl, optionally substituted amino, optionally substituted aryl, optionally substituted heteroaryl, optionally substituted alkoxyl, optionally substituted thioalkyl, optionally substituted alkylsulfinyl, optionally substituted alkylsulfonyl, optionally substituted alkylamino, thioamido, amidosulfonyl, alkoxycarbonyl, carboxamide, amino-carbonyl, alkylamine-carbonyl, and optionally substituted C1-C6 alkyl; or a pharmaceutically acceptable salt thereof.

Also disclosed are methods for modulating calcium release activity in a mammal, the method comprising the step of administering to the mammal an effective amount of least one compound having a structure represented by a formula:

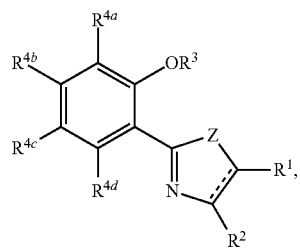

wherein ----- is an optional covalent bond, wherein valency is satisfied; wherein Z is selected from O and S; wherein $R^1$ is selected from hydrogen and optionally substituted C1-C6 alkyl; wherein $R^2$ is selected from nitrile, formyl, optionally substituted heteroaryl, optionally substituted heterocycloalkyl, optionally substituted alkoxyl, optionally substituted thioalkyl, optionally substituted alkylsulfonyl, optionally substituted alkylamino, thioamido, alkoxycarbonyl, carboxamide, amino-carbonyl, and alkylamine-carbonyl; wherein $R^3$ is selected from hydrogen and optionally substituted C1-C6 alkyl; wherein each of $R^{4a}$, $R^{4b}$, $R^{4c}$, and $R^{4d}$ is independently selected from hydrogen, halogen, hydroxyl, nitrile, nitro, thiol, formyl, optionally substituted amino, optionally substituted aryl, optionally substituted heteroaryl, optionally substituted alkoxyl, optionally substituted thioalkyl, optionally substituted alkylsulfinyl, optionally substituted alkylsulfonyl, optionally substituted alkylamino, thioamido, amidosulfonyl, alkoxycarbonyl, carboxamide, amino-carbonyl, alkylamine-carbonyl, and optionally substituted C1-C6 alkyl; or a pharmaceutically acceptable salt thereof.

Also disclosed are methods for modulating calcium release activity in a mammalian cell, the method comprising the step of administering to the cell an effective amount of least one compound having a structure represented by a formula:

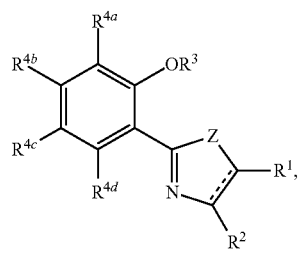

wherein ----- is an optional covalent bond, wherein valency is satisfied; wherein Z is selected from O and S; wherein $R^1$ is selected from hydrogen and optionally substituted C1-C6 alkyl; wherein $R^2$ is selected from nitrile, formyl, optionally substituted heteroaryl, optionally substituted heterocycloalkyl, optionally substituted alkoxyl, optionally substituted thioalkyl, optionally substituted alkylsulfonyl, optionally substituted alkylamino, thioamido, alkoxycarbonyl, carboxamide, amino-carbonyl, and alkylamine-carbonyl;

wherein R³ is selected from hydrogen and optionally substituted C1-C6 alkyl; wherein each of R⁴ᵃ, R⁴ᵇ, R⁴ᶜ, and R⁴ᵈ is independently selected from hydrogen, halogen, hydroxyl, nitrile, nitro, thiol, formyl, optionally substituted amino, optionally substituted aryl, optionally substituted heteroaryl, optionally substituted alkoxyl, optionally substituted thioalkyl, optionally substituted alkylsulfinyl, optionally substituted alkylsulfonyl, optionally substituted alkylamino, thioamido, amidosulfonyl, alkoxycarbonyl, carboxamide, amino-carbonyl, alkylamine-carbonyl, and optionally substituted C1-C6 alkyl; or a pharmaceutically acceptable salt thereof.

Also disclosed are kits comprising at least one compound having a structure represented by a formula:

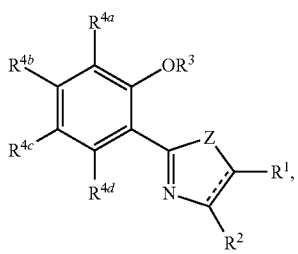

wherein ----- is an optional covalent bond, wherein valency is satisfied; wherein Z is selected from O and S; wherein R¹ is selected from hydrogen and optionally substituted C1-C6 alkyl; wherein R² is selected from nitrile, formyl, optionally substituted heteroaryl, optionally substituted heterocycloalkyl, optionally substituted alkoxyl, optionally substituted thioalkyl, optionally substituted alkylsulfonyl, optionally substituted alkylamino, thioamido, alkoxycarbonyl, carboxamide, amino-carbonyl, and alkylamine-carbonyl; wherein R³ is selected from hydrogen and optionally substituted C1-C6 alkyl; wherein each of R⁴ᵃ, R⁴ᵇ, R⁴ᶜ, and R⁴ᵈ is independently selected from hydrogen, halogen, hydroxyl, nitrile, nitro, thiol, formyl, optionally substituted amino, optionally substituted aryl, optionally substituted heteroaryl, optionally substituted alkoxyl, optionally substituted thioalkyl, optionally substituted alkylsulfinyl, optionally substituted alkylsulfonyl, optionally substituted alkylamino, thioamido, amidosulfonyl, alkoxycarbonyl, carboxamide, amino-carbonyl, alkylamine-carbonyl, and optionally substituted C1-C6 alkyl; or a pharmaceutically acceptable salt thereof, and one or more of: at least one agent known to increase calcium release; at least one agent known to decrease calcium release; at least one agent known to treat a disorder related to calcium release in a mammal; or instructions for treating a disorder related to calcium release in a mammal.

Also disclosed are pharmaceutical compositions comprising a therapeutically effective amount of a compound having a structure represented by a formula:

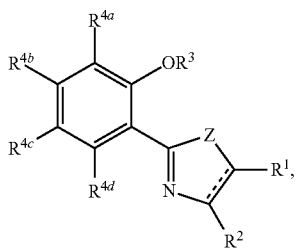

wherein ----- is an optional covalent bond, wherein valency is satisfied; wherein Z is selected from O and S; wherein R¹ is selected from hydrogen and optionally substituted C1-C6 alkyl; wherein R² is selected from nitrile, formyl, optionally substituted heteroaryl, optionally substituted heterocloalkyl, optionally substituted alkoxyl, optionally substituted thioalkyl, optionally substituted alkylsulfonyl, optionally substituted alkylamino, thioamido, alkoxycarbonyl, carboxamide, amino-carbonyl, and alkylamine-carbonyl; wherein R³ is selected from hydrogen and optionally substituted C1-C6 alkyl; wherein each of R⁴ᵃ, R⁴ᵇ, R⁴ᶜ, and R⁴ᵈ is independently selected from hydrogen, halogen, hydroxyl, nitrile, nitro, thiol, formyl, optionally substituted amino, optionally substituted aryl, optionally substituted heteroaryl, optionally substituted alkoxyl, optionally substituted thioalkyl, optionally substituted alkylsulfinyl, optionally substituted alkylsulfonyl, optionally substituted alkylamino, thioamido, amidosulfonyl, alkoxycarbonyl, carboxamide, amino-carbonyl, alkylamine-carbonyl, and optionally substituted C1-C6 alkyl; or a pharmaceutically acceptable salt thereof, and a pharmaceutically acceptable carrier or diluent.

Also disclosed are uses of a compound for the treatment of a disorder related to calcium release in a mammal, the compound having a structure represented by a formula:

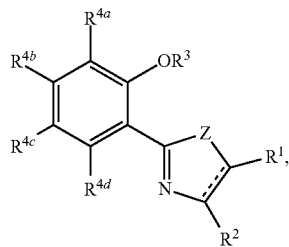

wherein ----- is an optional covalent bond, wherein valency is satisfied; wherein Z is selected from O and S; wherein R¹ is selected from hydrogen and optionally substituted C1-C6 alkyl; wherein R² is selected from nitrile, formyl, optionally substituted heteroaryl, optionally substituted heterocycloalkyl, optionally substituted alkoxyl, optionally substituted thioalkyl, optionally substituted alkylsulfonyl, optionally substituted alkylamino, thioamido, alkoxycarbonyl, carboxamide, amino-carbonyl, and alkylamine-carbonyl; wherein R³ is selected from hydrogen and optionally substituted C1-C6 alkyl; wherein each of R⁴ᵃ, R⁴ᵇ, R⁴ᶜ, and R⁴ᵈ is independently selected from hydrogen, halogen, hydroxyl, nitrile, nitro, thiol, formyl, optionally substituted amino, optionally substituted aryl, optionally substituted heteroaryl, optionally substituted alkoxyl, optionally substituted thioalkyl, optionally substituted alkylsulfinyl, optionally substituted alkylsulfonyl, optionally substituted alkylamino, thioamido, amidosulfonyl, alkoxycarbonyl, carboxamide, amino-carbonyl, alkylamine-carbonyl, and optionally substituted C1-C6 alkyl; or a pharmaceutically acceptable salt thereof.

Also disclosed are methods for isolating biologically active compounds comprising the steps of: culturing *Streptomyces* sp. CP32 in ISP2 medium for about 5-10 days; extracting the supernatant with a resin; and, eluting the resin.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several embodiments and together with the description serve to explain the principles of the invention.

FIG. 2 representative heteronuclear multiple bond coherence (HMBC), $^1$H-$^1$H COSY, and NOESY correlations of exemplary compounds.

Figure 1:
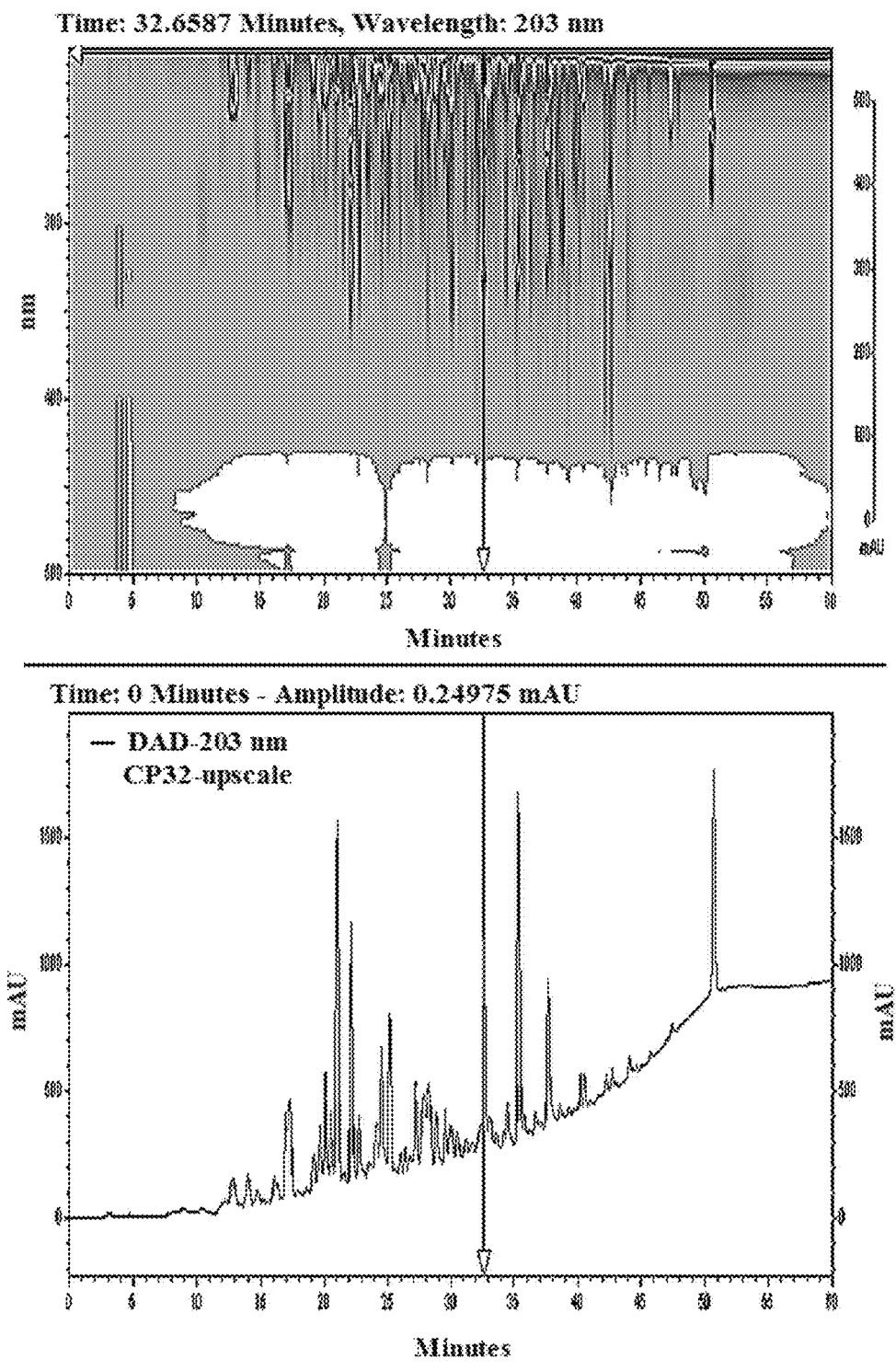
FIG. 1 shows a representative elution profile for an extract prepared from Streptomyces sp. CP32 according to the methods of the invention.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples and Figures included herein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. DEFINITIONS

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or can not occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of one or more neurological and/or psychiatric disorder associated with glutamate dysfunction prior to the administering step. In some aspects of the disclosed method, the subject has been diagnosed with a need for negative allosteric modulation of metabotropic glutamate receptor activity prior to the administering step. In some aspects of the disclosed method, the subject has been diagnosed with a need for partial antagonism of metabotropic glutamate receptor activity prior to the administering step.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein.

As used herein, the phrase "identified to be in need of treatment for a disorder," or the like, refers to selection of a subject based upon need for treatment of the disorder. For example, a subject can be identified as having a need for treatment of a disorder (e.g., a disorder related to intracellular calcium release) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, target metabotropic glutamate receptor, or other biological entity together in such a manner that the compound can affect the activity of the target (e.g., receptor, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side affects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "$EC_{50}$," is intended to refer to the concentration of a substance (e.g., a compound or a drug) that is required for 50% agonism of a biological process, or component of a process, including a protein, subunit, organelle, ribonucleoprotein, etc. In one aspect, an $EC_{50}$ can refer to the concentration of a substance that is required for 50% agonism in vivo, as further defined elsewhere herein. In a further aspect, $EC_{50}$ refers to the concentration of agonist that provokes a response halfway between the baseline and maximum response.

As used herein, "$IC_{50}$," is intended to refer to the concentration of a substance (e.g., a compound or a drug) that is required for 50% inhibition of a biological process, or component of a process, including a protein, subunit, organelle, ribonucleoprotein, etc. In one aspect, an $IC_{50}$ can refer to the concentration of a substance that is required for 50% inhibition in vivo, as further defined elsewhere herein. In a further aspect, $IC_{50}$ refers to the half maximal (50%) inhibitory concentration (IC) of a substance.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

As used herein, the term "agonist" refers to any exogenously administered compound or agent that binds to the target receptor and increases the activity of the target receptor. An agonist mimics the action of a "native" or "natural" ligand which interacts with the target receptor. Agonists can be homologous to these natural ligands in respect to conformation, charge or other characteristics. Thus, agonists can be recognized by receptors expressed on cell surfaces. This recognition can result in physiologic and/or biochemical changes within the cell, such that the cell reacts to the presence of the agonist in the same manner as if the natural compound was present. "Agonist" also encompasses full agonists, partial agonists, irreversible agonists, co-agonists and inverse agonists. A "partial agonist" is a compound or agent in which the maximal physiologic and/or biochemical changes that occur upon partial agonist administration may be less than the maximal effect exhibited by full agonists or the natural ligand. "A co-agonist" works with other co-agonists to produce the desired agonist effect together. For example, NMDA receptor activation requires the binding of both of glutamate and glycine co-agonists. An "irreversible agonist" binds permanently to a receptor in such a manner that the receptor is permanently activated.

As used herein, the term "antagonist" refers to any exogenously administered compound or agent that interacts or binds with the target receptor and reduces, blocks or inhibits the physiological or pharmacological response characteristic of the receptor. Thus, an antagonist can inhibit the action of a "native" or "natural" ligand which activates the target receptor. Antagonists may or may not be homologous to these natural ligands in respect to conformation, charge or other characteristics. Antagonists do not result in physiologic and/or biochemical changes within the cell, such that the cell reacts to the presence of the antagonist in the same manner as if the natural compound was absent.

As used herein, the term "negative allosteric modulator" refers to any exogenously administered compound or agent that directly or indirectly inhibits the activity of the target receptor in the presence of the endogenous ligand in an animal, in particular a mammal, for example a human. The term is synonymous with the terms "allosteric inhibitor," "noncompetitive inhibitor," "allosteric antagonist," and "noncompetitive antagonist".

As used herein, the term "positive allosteric modulator" refers to any exogenously administered compound or agent that directly or indirectly augments the activity of the target receptor in the presence or in the absence of the endogenous ligand (such as glutamate) in an animal, in particular a mammal, for example a human. The term "positive allosteric modulator" includes a compound that is an "allosteric potentiator" or an "allosteric agonist," as well as a compound that has mixed activity as both an "allosteric potentiator" and an "allosteric agonist."

As used herein, the term "allosteric potentiator" refers to any exogenously administered compound or agent that directly or indirectly augments the response produced by the endogenous ligand (such as glutamate) when it binds to the orthosteric site of the target receptor in an animal, in particular a mammal, for example a human. A receptor allosteric potentiator binds to a site other than the orthosteric site (an allosteric site) and positively augments the response of the receptor to an agonist. Because it does not induce desensitization of the receptor, activity of a compound as a receptor allosteric potentiator provides advantages over the use of a pure receptor allosteric agonist. Such advantages can include, for example, increased safety margin, higher tolerability, diminished potential for abuse, and reduced toxicity.

As used herein, the term "allosteric agonist" refers to any exogenously administered compound or agent that directly augments the activity of the target receptor in the absence of the endogenous ligand (such as glutamate) in an animal, in particular a mammal, for example a human. A receptor allosteric agonist binds to the orthosteric glutamate site of the target receptor and directly influences the orthosteric site of the target receptor. Because it does not require the presence of the endogenous ligand, activity of a compound as a receptor allosteric agonist provides advantages over the use of a pure receptor allosteric potentiator, such as more rapid onset of action.

As used herein, the term "direct activator" refers to any exogenously administered compound or agent that directly interacts with the target receptor and causes an increase in the activity of the receptor.

As used herein, the term "indirect activator" refers to any exogenously administered compound or agent that does not directly interact with the target receptor, but interacts with another cellular molecule to cause an increase in the activity of the receptor. For example, an indirect activator can interact with a cellular molecule that is involved in a signal transduction pathway that modulates the function of the target receptor. An example of an indirect inhibitor that is involved in a signal transduction pathway of the target receptor is one that inhibits a kinase that inhibits the target receptor via phosphorrylation. Another example of an indirect inhibitor of target receptor would be an agent that increases the expression of target receptor and thereby increase the target receptor function. Another example of an indirect activator of a target receptor would be an agent that increases translation of a gene encoding the target receptor.

As used herein, the term "direct inhibitor" refers to any exogenously administered compound or agent that directly interacts with the target receptor and causes a decrease in the activity of the receptor.

As used herein, the term "indirect inhibitor" refers to any exogenously administered compound or agent that does not directly interact with the target receptor, but interacts with another cellular molecule to cause a decrease in the activity of the receptor. For example, an indirect inhibitor can interact with a cellular molecule that is involved in a signal transduction pathway that modulates the function of the target receptor. An example of an indirect inhibitor that is involved in a signal transduction pathway of the target receptor is one that inhibits a kinase that activates the target receptor via phosphorrylation. Another example of an indirect inhibitor of NF-~B would be an agent that inhibits the expression of target receptor and thereby prevent the target receptor from functioning. Another example of an indirect inhibitor of a target receptor would be an agent that inhibits translation of a gene encoding the target receptor.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "A$^1$," "A$^2$," "A$^3$," and "A$^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more CH$_2$ groups linked to one another. The polyalkylene group can be represented by the formula —(CH$_2$)$_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —OA$^1$ where A$^1$ is alkyl or cycloalkyl as defined above. "Alkoxy" also includes polymers of alkoxy groups as just described; that is, an alkoxy can be a polyether such as —OA$^1$-OA$^2$ or —OA$^1$-(OA$^2$)$_a$-OA$^3$, where "a" is an integer of from 1 to 200 and A$^1$, A$^2$, and A$^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as (A$^1$A$^2$)C=C(A$^3$A$^4$) are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —$N(-alkyl)_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)$A^1$ or —C(O)O$A^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula -($A^1$O(O)C-$A^2$-C(O)O)$_a$— or -($A^1$O(O)C-$A^2$-OC(O))$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1$O$A^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula -($A^1$O-$A^2$O)$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "heterocycle," as used herein refers to single and multi-cyclic aromatic or non-aromatic ring systems in which at least one of the ring members is other than carbon. Heterocycle includes pyridinde, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridine, pyridazine, pyrimidine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like.

The term "hydroxyl" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" as used herein is represented by the formula —$N_3$.

The term "nitro" as used herein is represented by the formula —$NO_2$.

The term "nitrile" as used herein is represented by the formula —CN.

The term "silyl" as used herein is represented by the formula —$SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —$S(O)A^1$, —$S(O)_2A^1$, —$OS(O)_2A^1$, or —$OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —$S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" is used herein is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; —$(CH_2)_{0-4}R°$; —$(CH_2)_{0-4}OR°$; —$O(CH_2)_{0-4}R°$, —O—$(CH_2)_{0-4}C(O)OR°$; —$(CH_2)_{0-4}CH(OR°)_2$; —$(CH_2)_{0-4}SR°$; —$(CH_2)_{0-4}$Ph, which may be substituted with R°; —$(CH_2)_{0-4}O(CH_2)_{0-1}$Ph which may be substituted with R°; —CH=CHPh, which may be substituted with R°; —$(CH_2)_{0-4}O(CH_2)_{0-1}$-pyridyl which may be substituted with R°; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR$—, $SC(S)SR°$; —$(CH_2)_{0-4}SC(O)R°$; —$(CH_2)_{0-4}C(O)NR°_2$; —$C(S)NR°_2$; —$C(S)SR°$; —$SC(S)SR°$, —$(CH_2)_{0-4}OC(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R°$; —$N(R°)S(O)_2NR°_2$; —$N(R°)S(O)_2R°$; —$N(OR°)R°$; —$C(NH)NR°_2$; —$P(O)_2R°$; —$P(O)R°_2$; —$OP(O)R°_2$; —$OP(O)(OR°)_2$; $SiR°_3$; —$(C_{1-4}$ straight or branched)alkylene)O—$N(R°)_2$; or —$(C_{1-4}$ straight or branched alkylene)$C(O)O$—$N(R°)_2$, wherein each R° may be substituted as defined below and is independently hydrogen, $C_{1-6}$ aliphatic, —$CH_2$Ph, —$O(CH_2)_{0-1}$Ph, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —$(CH_2)_{0-2}R^●$, -(haloR$^●$), —$(CH_2)_{0-2}OH$, —$(CH_2)_{0-2}OR^●$, —$(CH_2)_{0-2}CH(OR^●)_2$; —O(haloR$^●$), —CN, —$N_3$, —$(CH_2)_{0-2}C(O)R^●$, —$(CH_2)_{0-2}C(O)OH$, —$(CH_2)_{0-2}C(O)OR^●$, —$(CH_2)_{0-2}SR^●$, —$(CH_2)_{0-2}SH$, —$(CH_2)_{0-2}NH_2$, —$(CH_2)_{0-2}NHR^●$, —$(CH_2)_{0-2}NR^●_2$, —$NO_2$, —$SiR^●_3$, —$OSiR^●_3$, —$C(O)SR^●$, —$(C_{1-4}$ straight or branched alkylene)$C(O)OR^●$, or —$SSR^●$ wherein each $R^●$ is unsubstituted or where preceded by "halo" is substituted only with one or more halogens, and is independently selected from $C_{1-4}$ aliphatic, —$CH_2$Ph, —$O(CH_2)_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =$NNR^*_2$, =$NNHC(O)R^*$, =$NNHC(O)OR^*$, =$NNHS(O)_2R^*$, =$NR^*$, =$NOR^*$, —$O(C(R^*_2))_{2-3}O$—, or —$S(C(R^*_2))_{2-3}S$—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R is unsubstituted or where preceded by "halo" is substituted only with one or more halogens, and is independently $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger_2$, —C(S)NR$^\dagger_2$, —C(NH)NR$^\dagger_2$, or —N(R$^\dagger$)S(O)$_2$R$^\dagger$; wherein each R$^\dagger$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, brosylate, and halides.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure

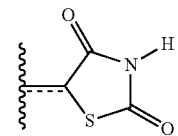

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5,6,7,8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds can be isotopically-labelled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of the present invention and prodrugs thereof can generally be prepared by carrying out the procedures below, by substituting a readily available isotopically labelled reagent for a non-isotopically labelled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

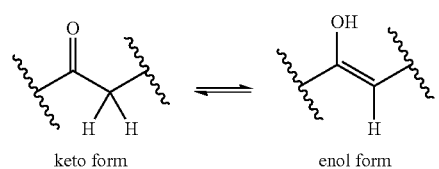

-continued

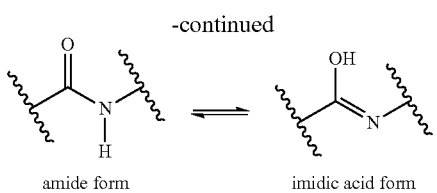

amide form          imidic acid form

Likewise, amides with an N-hydrogen can exist in an equilibrium of the amide form and the imidic acid form. Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

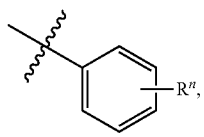

which is understood to be equivalent to a formula:

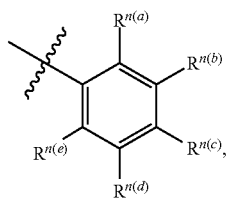

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. COMPOUNDS

In one aspect, the invention relates to compounds, or pharmaceutically acceptable derivatives thereof, useful as modulators of calcium release. One way the disclosed compounds or pharmaceutically acceptable derivatives thereof achieve this action is through binding to a cellular protein. In a further aspect, the cellular protein is a cell surface receptor. In a yet further aspect, the activity of the cell surface receptor modulates, either directly or indirectly, calcium release from and/or calcium uptake into intracellular calcium stores. In a still further aspect, the cell surface receptor is a G-protein. In an even further aspect, the G-protein is selected from histamine H1 receptor, 5HT-2B receptor, and kappa opioid receptor. In a further aspect, the cellular protein is an intracellular protein.

1. Structure

In one aspect, the invention relates to a compound having a structure represented by a formula:

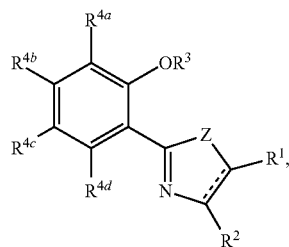

wherein ----- is an optional covalent bond, wherein valency is satisfied; wherein Z is selected from O and S; wherein $R^1$ is selected from hydrogen and optionally substituted C1-C6 alkyl; wherein $R^2$ is selected from nitrile, formyl, optionally substituted heteroaryl, optionally substituted heterocycloalkyl, optionally substituted alkoxyl, optionally substituted thioalkyl, optionally substituted alkylsulfonyl, optionally substituted alkylamino, thioamido, alkoxycarbonyl, carboxamide, amino-carbonyl, and alkylamine-carbonyl; wherein $R^3$ is selected from hydrogen and optionally substituted C1-C6 alkyl; wherein each of $R^{4a}$, $R^{4b}$, $R^{4c}$, and $R^{4d}$ is independently selected from hydrogen, halogen, hydroxyl, nitrile, nitro, thiol, formyl, optionally substituted amino, optionally substituted aryl, optionally substituted heteroaryl, optionally substituted alkoxyl, optionally substituted thioalkyl, optionally substituted alkylsulfinyl, optionally substituted alkylsulfonyl, optionally substituted alkylamino, thioamido, amidosulfonyl, alkoxycarbonyl, carboxamide, amino-carbonyl, alkylamine-carbonyl, and optionally substituted C1-C6 alkyl; or a pharmaceutically acceptable salt thereof. In a further aspect, the covalent bond represented by ----- is present.

In a further aspect, the compound is isolated. In a still further aspect, the compound is isolated from extract of *Streptomyces* sp. CP32. In a further aspect, the compound is synthetic or semi-synthetically prepared. In a further aspect, the compound is purified.

In a further aspect, the compound has a structure represented by a formula:

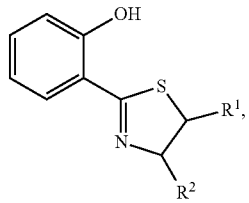

wherein $R^1$ is selected from hydrogen and optionally substituted C1-C6 alkyl; wherein $R^2$ is selected from nitrile, formyl, optionally substituted C1-C6 alkyl, optionally substituted heteroaryl, optionally substituted heterocycloalkyl, optionally substituted alkoxyl, optionally substituted thioalkyl, optionally substituted alkylsulfonyl, optionally substituted alkylamino, thioamido, alkoxycarbonyl, carboxamide, amino-carbonyl, and alkylamine-carbonyl; or a pharmaceutically acceptable salt thereof.

In a further aspect, the compound has a structure represented by a formula:

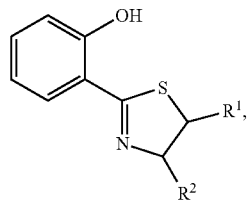

wherein $R^1$ is selected from hydrogen and optionally substituted C1-C6 alkyl; wherein $R^2$ is selected from nitrile, formyl, optionally substituted heteroaryl, optionally substituted heterocycloalkyl, optionally substituted alkoxyl, optionally substituted thioalkyl, optionally substituted alkylsulfonyl, optionally substituted alkylamino, thioamido, alkoxycarbonyl, carboxamide, amino-carbonyl, and alkylamine-carbonyl; or a pharmaceutically acceptable salt thereof.

a. Z Groups

In one aspect, Z is selected from O and S. In a further aspect, Z is S. In a still further aspect Z is O.

b. Y Groups

In one aspect, Y is selected from O, S, and NH. In a further aspect, Y is O. In a still further aspect, Y is S. In a yet further aspect, Y is NH. In an even further aspect, Y is O or S. In a further aspect, Y is O or NH. In a yet further aspect, Y is S or NH.

c. $R^1$ Groups

In one aspect, $R^1$ is selected from hydrogen and optionally substituted C1-C6 alkyl. In a further aspect, $R^1$ is hydrogen. In a still further aspect, $R^1$ is optionally substituted C1-C6 alkyl. In a yet further aspect, $R^1$ is C1-C6 alkyl. In an even further aspect, $R^1$ is methyl. In a further aspect, $R^1$ is methyl, ethyl, propyl, or butyl.

d. $R^2$ Groups

In one aspect, $R^2$ is selected from nitrile, formyl, optionally substituted heteroaryl, optionally substituted heterocycloalkyl, optionally substituted alkoxyl, optionally substituted thioalkyl, optionally substituted alkylsulfonyl, optionally substituted alkylamino, thioamido, alkoxycarbonyl, carboxamide, amino-carbonyl, and alkylamine-carbonyl. In a further aspect, $R^2$ is selected from nitrile, formyl, optionally substituted heteroaryl, optionally substituted heterocycloalkyl, optionally substituted alkoxyl, optionally substituted thioalkyl, optionally substituted alkylamino, thioamido, alkoxycarbonyl, carboxamide, amino-carbonyl, and alkylamine-carbonyl. In a still further aspect, $R^2$ is selected from formyl, optionally substituted heterocycloalkyl, alkoxycarbonyl, carboxamide, amino-carbonyl, and alkylamine-carbonyl.

In one aspect, $R^2$ is has a structure represented by a formula:

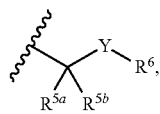

wherein Y is selected from O, S, and NH; wherein $R^{5a}$ and $R^{5b}$ together comprise =O or =S, or wherein each of $R^{5a}$ and $R^{5b}$ is independently selected from hydrogen and optionally substituted C1-C6 alkyl; wherein $R^6$ is selected from hydrogen, optionally substituted C1-C6 alkyl, optionally substituted aryl, optionally substituted heteroaryl, optionally substituted cycloalkyl, optionally substituted heterocycloalkyl, and optionally substituted benzyl.

In one aspect, $R^2$ is has a structure represented by a formula:

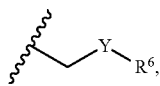

wherein Y is selected from O, S, and NH; wherein $R^6$ is selected from hydrogen, optionally substituted C1-C6 alkyl, optionally substituted aryl, optionally substituted heteroaryl, optionally substituted cycloalkyl, optionally substituted heterocycloalkyl, and optionally substituted benzyl.

In one aspect, $R^2$ is has a structure represented by a formula:

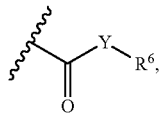

wherein Y is selected from O, S, and NH; wherein $R^6$ is selected from hydrogen, optionally substituted C1-C6 alkyl, optionally substituted aryl, optionally substituted heteroaryl, optionally substituted cycloalkyl, optionally substituted heterocycloalkyl, and optionally substituted benzyl.

In one aspect, $R^2$ is has a structure represented by a formula:

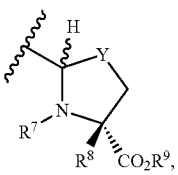

wherein Y is selected from O, S, and NH; wherein each of $R^7$, $R^8$, and $R^9$ is independently selected from hydrogen and optionally substituted C1-C6 alkyl.

In one aspect, $R^2$ is has a structure represented by a formula:

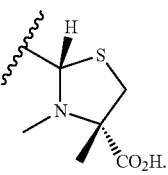

In one aspect, $R^2$ is has a structure represented by a formula:

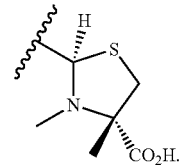

e. $R^3$ Groups

In one aspect, $R^{3'}$ is selected from hydrogen and optionally substituted C1-C6 alkyl. In a further aspect, $R^3$ is hydrogen. In a still further aspect, $R^3$ is optionally substituted C1-C6 alkyl.

f. $R^{4a}$, $R^{4b}$, $R^{4c}$, and $R^{4d}$ Groups

In one aspect, each of $R^{4a}$, $R^{4b}$, $R^{4c}$, and $R^{4d}$ is independently selected from hydrogen, halogen, hydroxyl, nitrile, nitro, thiol, formyl, optionally substituted amino, optionally substituted aryl, optionally substituted heteroaryl, optionally substituted alkoxyl, optionally substituted thioalkyl, optionally substituted alkylsulfinyl, optionally substituted alkylsulfonyl, optionally substituted alkylamino, thioamido, amidosulfonyl, alkoxycarbonyl, carboxamide, amino-carbonyl, alkylamine-carbonyl, and optionally substituted C1-C6 alkyl.

In one aspect, $R^{4a}$ is hydrogen, halogen, or optionally substituted C1-C6 alkyl. In a further aspect, $R^{4b}$ is hydrogen, halogen, or optionally substituted C1-C6 alkyl. In a still further aspect, $R^{4c}$ is hydrogen, halogen, or optionally substituted C1-C6 alkyl. In an even further aspect, $R^{4d}$ is hydrogen, halogen, or optionally substituted C1-C6 alkyl. In one aspect, g. $R^{5a}$ and $R^{5b}$ Groups In one aspect, $R^{5a}$ and $R^{5b}$ together comprise =O or =S, or wherein each of $R^{5a}$ and $R^{5b}$ is independently selected from hydrogen and optionally substituted C1-C6 alkyl.

h. $R^6$ Groups

In one aspect, $R^6$ is selected from hydrogen, optionally substituted C1-C6 alkyl, optionally substituted aryl, optionally substituted heteroaryl, optionally substituted cycloalkyl, optionally substituted heterocycloalkyl, and optionally substituted benzyl.

i. $R^7$ Groups

In one aspect, each of $R^7$, $R^8$, and $R^9$ is independently selected from hydrogen and optionally substituted C1-C6 alkyl. In a further aspect, of $R^7$ is selected from hydrogen and optionally substituted C1-C6 alkyl.

j. $R^8$ Groups

In one aspect, each of $R^7$, $R^8$, and $R^9$ is independently selected from hydrogen and optionally substituted C1-C6 alkyl. In a further aspect, of $R^8$ is selected from hydrogen and optionally substituted C1-C6 alkyl.

k. R⁹ Groups

In one aspect, each of $R^7$, $R^8$, and $R^9$ is independently selected from hydrogen and optionally substituted C1-C6 alkyl. In a further aspect, of $R^9$ is selected from hydrogen and optionally substituted C1-C6 alkyl.

2. Example Compounds

In one aspect, the compound is selected from:

In a further aspect, the compound is selected from:

In a still further aspect, the compound is not:

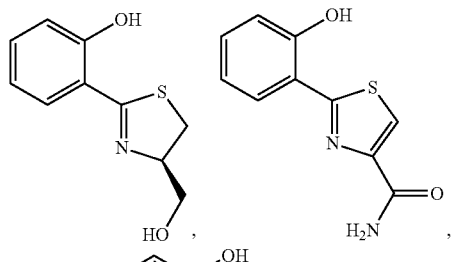

-continued

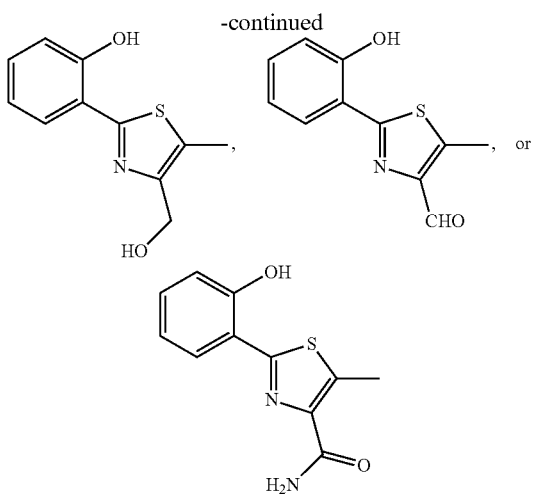

It is understood that the disclosed compounds can be used in connection with the disclosed methods, compositions, kits, and uses.

3. Activity

In one aspect, the disclosed compounds and pharmaceutically acceptable derivatives thereof that are disclosed herein exhibit modulation of calcium release in a mammal. In a yet further aspect, the compounds exhibit modulation of calcium release in the dorsal root ganglion cells of a mammal. In a still further aspect, the compounds modulate calcium release by acting as an agonist, antagonist, negative allosteric modulator, positive allosteric modulator, allosteric potentiator, allosteric agonist, direct inhibitor or indirect inhibitor.

In one aspect, the disclosed compounds and pharmaceutically acceptable derivatives thereof that are disclosed herein exhibit modulation of calcium release in a mammal cells. In a yet further aspect, the compounds exhibit modulation of calcium release in mouse dorsal root ganglion cells. In a still further aspect, the compounds modulate calcium release by acting as an agonist, antagonist, negative allosteric modulator, positive allosteric modulator, allosteric potentiator, allosteric agonist, direct inhibitor or indirect inhibitor.

In a further aspect, the compounds exhibit positive modulation of calcium release. In a still further aspect, the modulation is agonism. In a yet further aspect, the modulation is stimulation.

In a further aspect, the compounds exhibit negative modulation of calcium release. In a still further aspect, the modulation is antagonism. In a yet further aspect, the modulation is inhibition.

In one aspect, the disclosed compounds and pharmaceutically acceptable derivatives thereof that are disclosed herein exhibit modulation of calcium release in a mammal by modulation of a target cell receptor. In a yet further aspect, the compounds exhibit modulation of calcium release by modulation of a target cell receptor in dorsal root ganglion cells. In a further aspect, the compounds modulate a target cell receptor by acting as an agonist, antagonist, negative allosteric modulator, positive allosteric modulator, allosteric potentiator, allosteric agonist, direct inhibitor or indirect inhibitor.

In one aspect, the disclosed compounds and pharmaceutically acceptable derivatives thereof that are disclosed herein exhibit modulation of calcium release in a mammal cells by modulation of a target cell receptor. In a yet further aspect, the compounds exhibit modulation of calcium release by modulation of target cell receptor in mouse dorsal root ganglion cells. In a still further aspect, the compounds modulate calcium release by acting as an agonist, antagonist, negative allosteric modulator, positive allosteric modulator, allosteric potentiator, allosteric agonist, direct activator, indirect activator, direct inhibitor or indirect inhibitor.

In a further aspect, the compounds exhibit positive modulation of a target cell receptor. In a still further aspect, the modulation is agonism. In a yet further aspect, the modulation is stimulation. In an even further aspect modulation is positive allosteric modulation. In a further aspect, modulation is by direct activation. In a still further aspect, activation is by indirect activation.

In a further aspect, the compounds exhibit negative modulation of calcium release. In a still further aspect, the modulation is antagonism. In a yet further aspect, the modulation is inhibition. In an even further aspect, modulation is negative allosteric modulation. In a further aspect, modulation is by direct inhibition. In a still further aspect, modulation is a indirect inhibition.

In one aspect, the compound modulates the 5HT-2B receptor. In a further aspect, modulation of the 5HT-2B receptor modulates calcium release. In a still further aspect, modulation of the 5HT-2B receptor is negative. In a still further aspect, the modulation is antagonism. In a yet further aspect, the modulation is inhibition. In an even further aspect, modulation is negative allosteric modulation. In a further aspect, modulation is by direct inhibition. In a still further aspect, modulation is a indirect inhibition.

In one aspect, the compound modulates the 5HT-2B receptor. In a further aspect, modulation of the 5HT-2B receptor modulates calcium release. In a still further aspect, modulation of the 5HT-2B receptor is positive. In a still further aspect, the modulation is agonism. In a yet further aspect, the modulation is stimulation. In an even further aspect modulation is positive allosteric modulation. In a further aspect, modulation is by direct activation. In a still further aspect, activation is by indirect activation.

In one aspect, the compound modulates the histamine H1 receptor. In a further aspect, modulation of the histamine H1 receptor modulates calcium release. In a still further aspect, modulation of the histamine H1 receptor is negative. In a still further aspect, the modulation is antagonism. In a yet further aspect, the modulation is inhibition. In an even further aspect, modulation is negative allosteric modulation. In a further aspect, modulation is by direct inhibition. In a still further aspect, modulation is a indirect inhibition.

In one aspect, the compound modulates the histamine H1 receptor. In a further aspect, modulation of the histamine H1 receptor modulates calcium release. In a still further aspect, modulation of the histamine H1 receptor is positive. In a still further aspect, the modulation is agonism. In a yet further aspect, the modulation is stimulation. In an even further aspect modulation is positive allosteric modulation. In a further aspect, modulation is by direct activation. In a still further aspect, activation is by indirect activation.

In one aspect, the compound modulates the kappa opioid receptor. In a further aspect, modulation of the kappa opioid receptor modulates calcium release. In a still further aspect, modulation of the kappa opioid receptor is negative. In a still further aspect, the modulation is antagonism. In a yet further aspect, the modulation is inhibition. In an even further aspect, modulation is negative allosteric modulation. In a further aspect, modulation is by direct inhibition. In a still further aspect, modulation is a indirect inhibition.

In one aspect, the compound modulates the kappa opioid receptor. In a further aspect, modulation of the kappa opioid receptor modulates calcium release. In a still further aspect, modulation of the kappa opioid receptor is positive. In a still further aspect, the modulation is agonism. In a yet further aspect, the modulation is stimulation. In an even further aspect modulation is positive allosteric modulation. In a further aspect, modulation is by direct activation. In a still further aspect, activation is by indirect activation.

In a further aspect, the compound has an $EC_{50}$ of less than about 20 µM, less than about 10 µM, less than about 5 µM, or less than about 1 µM. In one aspect, the modulation is inhibition. In a further aspect, the compound has an $IC_{50}$ of less than about 20 µM, less than about 10 µM, less than about 5 µM, or less than about 1 µM.

C. METHODS OF MAKING THE COMPOUNDS

In one aspect, the invention relates to methods of making the disclosed compounds. The compounds of this invention can be prepared by employing reactions as shown in the disclosed schemes, in addition to other standard manipulations that are known in the literature, exemplified in the experimental sections or clear to one skilled in the art. An exemplary synthetic route is disclosed herein.

In one aspect, the invention relates to methods of making compounds useful as calcium release modulators, which can be useful in disorders associated with calcium release dysfunction and other diseases in which calcium release is involved. The compounds of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

In a further aspect, a compound comprises products of the disclosed methods. In a still further aspect, the invention comprises a pharmaceutical composition comprising a therapeutically effective amount of the product of the disclosed methods and a pharmaceutically acceptable carrier. In a still further aspect, the invention comprises a method for manufacturing a medicament comprising combining at least one compound of any of disclosed compounds or at least one product of the disclosed methods with a pharmaceutically acceptable carrier or diluent.

In one aspect, disclosed thaizolines and analogs thereof can be prepared as shown below.

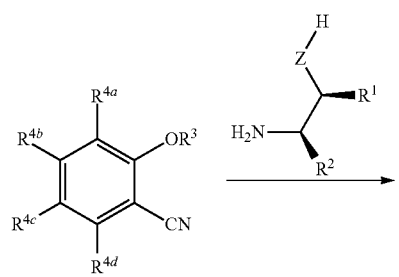

-continued

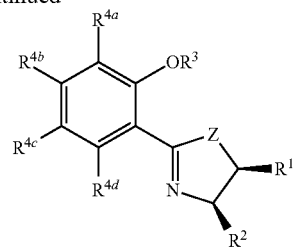

In the preceding example synthetic route, Z can be O or S; $R^1$ is selected from hydrogen and optionally substituted C1-C6 alkyl; $R^2$ is selected from nitrile, formyl, optionally substituted heteroaryl, optionally substituted heterocycloalkyl, optionally substituted alkoxyl, optionally substituted thioalkyl, optionally substituted alkylsulfonyl, optionally substituted alkylamino, thioamido, alkoxycarbonyl, carboxamide, amino-carbonyl, and alkylamine-carbonyl; $R^3$ is selected from hydrogen and optionally substituted C1-C6 alkyl; and each of $R^{4a}$, $R^{4b}$, $R^{4c}$, and $R^{4d}$ is independently selected from hydrogen, halogen, hydroxyl, nitrile, nitro, thiol, formyl, optionally substituted amino, optionally substituted aryl, optionally substituted heteroaryl, optionally substituted alkoxyl, optionally substituted thioalkyl, optionally substituted alkylsulfinyl, optionally substituted alkylsulfonyl, optionally substituted alkylamino, thioamido, amidosulfonyl, alkoxycarbonyl, carboxamide, amino-carbonyl, alkylamine-carbonyl, and optionally substituted C1-C6 alkyl.

Compounds are represented in generic form, with substituents as noted in compound descriptions elsewhere herein. A more specific example is set forth below.

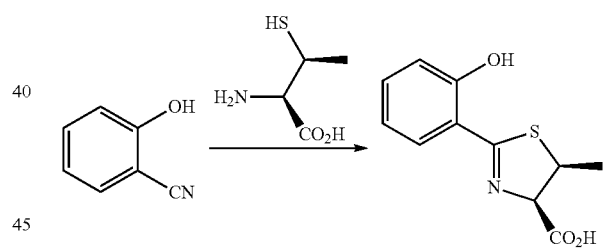

In one aspect, preparation begins with commercially available 2-hydroxybenzonitrile. As would be readily appreciated by those of skill, 2-hydroxybenzonitrile can be further substituted and/or alkylated. Cyclization of the thiazoline moiety can then be accomplished by condensation with an appropriately substituted 2-aminoethanethiol. Reaction can be performed, for example, in a phosphate buffer (pH 6.4) and methanol (1:1) at 50° C. over several days. In this example, 2-hydroxybenzonitrile can be condensed with (2R,3S)-2-amino-3-mercaptobutanoic acid to provide (4R,5S)-2-(2-hydroxyphenyl)-5-methyl-4,5-dihydrothiazole-4-carboxylic acid.

By appropriate selection of the 2-aminoethanethiol substituents, the identity of $R^1$ and $R^2$ as well as the stereochemistry at the carbon atoms adjacent to $R^1$ and $R^2$ can be controlled. Further, by appropriate selection of the 2-aminoethanethiol substituents, further reactions can be contemplated. For example, preparation of an analog bearing a leaving group (e.g., a halogen) can provide a pathway to unsaturated derivatives, as exemplified below:

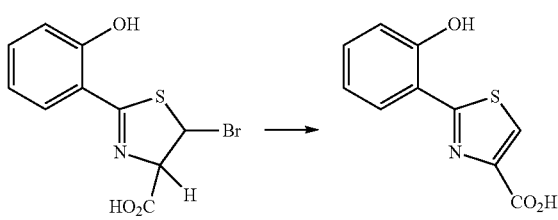 [SMILES: O=C(O)C1N=C(c2ccccc2O)SC1Br ; O=C(O)c1csc(-c2ccccc2O)n1]

As would also be readily appreciated by those of skill, functional group transformation of the remaining substituents (e.g., carboxylic acid converted to amide) can yield further analogs.

D. PHARMACEUTICAL COMPOSITIONS

In one aspect, the invention relates to pharmaceutical compositions comprising a therapeutically effective amount of a compound having a structure represented by a formula:

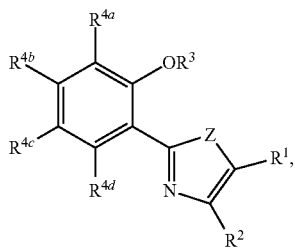

wherein ----- is an optional covalent bond, wherein valency is satisfied; wherein Z is selected from O and S; wherein $R^1$ is selected from hydrogen and optionally substituted C1-C6 alkyl; wherein $R^2$ is selected from nitrile, formyl, optionally substituted heteroaryl, optionally substituted heterocycloalkyl, optionally substituted alkoxyl, optionally substituted thioalkyl, optionally substituted alkylsulfonyl, optionally substituted alkylamino, thioamido, alkoxycarbonyl, carboxamide, amino-carbonyl, and alkylamine-carbonyl; wherein $R^3$ is selected from hydrogen and optionally substituted C1-C6 alkyl; wherein each of $R^{4a}$, $R^{4b}$, $R^{4c}$, and $R^{4d}$ is independently selected from hydrogen, halogen, hydroxyl, nitrile, nitro, thiol, formyl, optionally substituted amino, optionally substituted aryl, optionally substituted heteroaryl, optionally substituted alkoxyl, optionally substituted thioalkyl, optionally substituted alkylsulfinyl, optionally substituted alkylsulfonyl, optionally substituted alkylamino, thioamido, amidosulfonyl, alkoxycarbonyl, carboxamide, amino-carbonyl, alkylamine-carbonyl, and optionally substituted C1-C6 alkyl; or a pharmaceutically acceptable salt thereof.

In a further aspect, the compound has a structure represented by a formula:

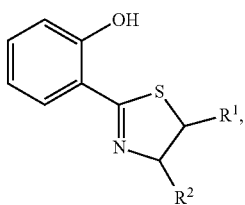

wherein $R^1$ is selected from hydrogen and optionally substituted C1-C6 alkyl; wherein $R^2$ is selected from nitrile, formyl, optionally substituted C1-C6 alkyl, optionally substituted heteroaryl, optionally substituted heterocycloalkyl, optionally substituted alkoxyl, optionally substituted thioalkyl, optionally substituted alkylsulfonyl, optionally substituted alkylamino, thioamido, alkoxycarbonyl, carboxamide, amino-carbonyl, and alkylamine-carbonyl; or a pharmaceutically acceptable salt thereof.

In a further aspect, the compound has a structure represented by a formula:

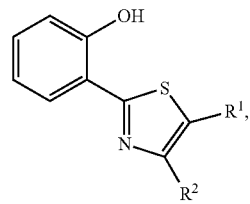

wherein $R^1$ is selected from hydrogen and optionally substituted C1-C6 alkyl; wherein $R^2$ is selected from nitrile, formyl, optionally substituted heteroaryl, optionally substituted heterocycloalkyl, optionally substituted alkoxyl, optionally substituted thioalkyl, optionally substituted alkylsulfonyl, optionally substituted alkylamino, thioamido, alkoxycarbonyl, carboxamide, amino-carbonyl, and alkylamine-carbonyl; or a pharmaceutically acceptable salt thereof.

In one aspect, the compound is selected from:

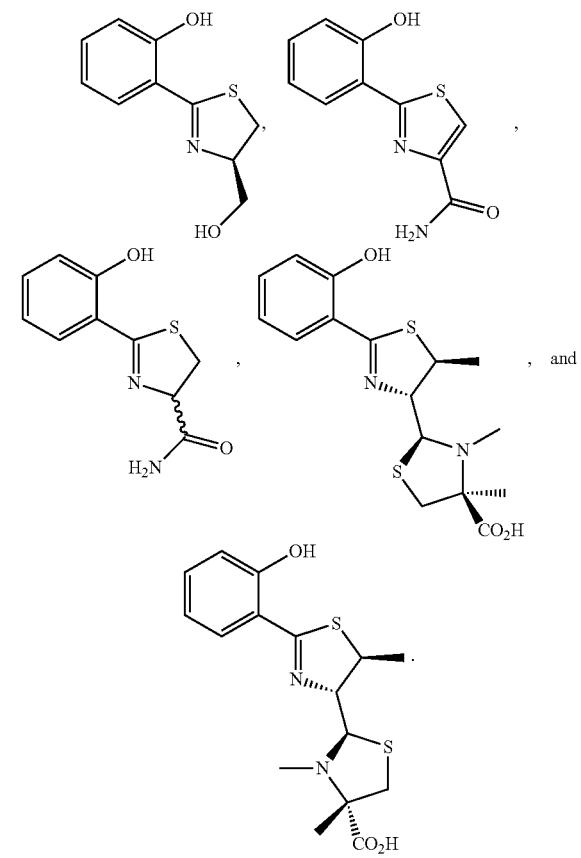

In a further aspect, the compound is selected from:

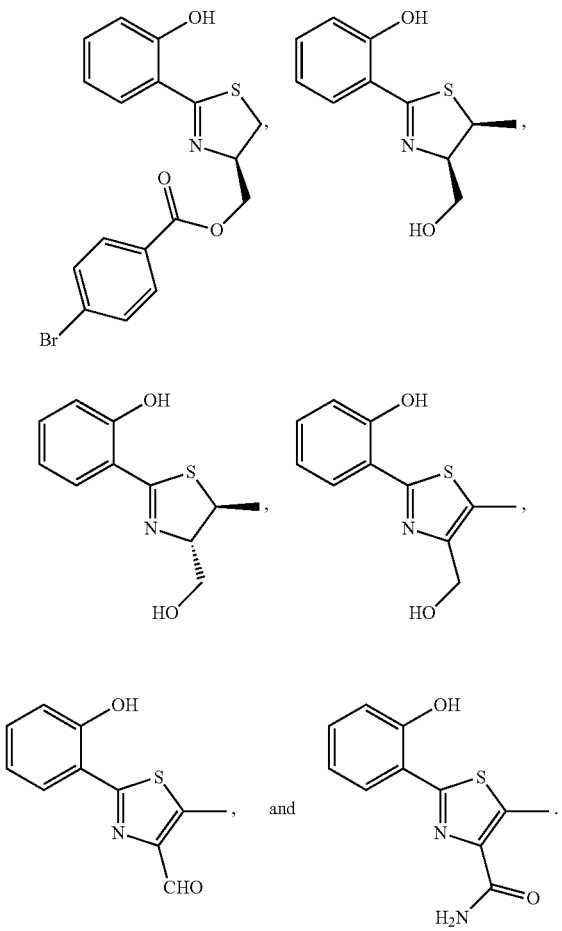

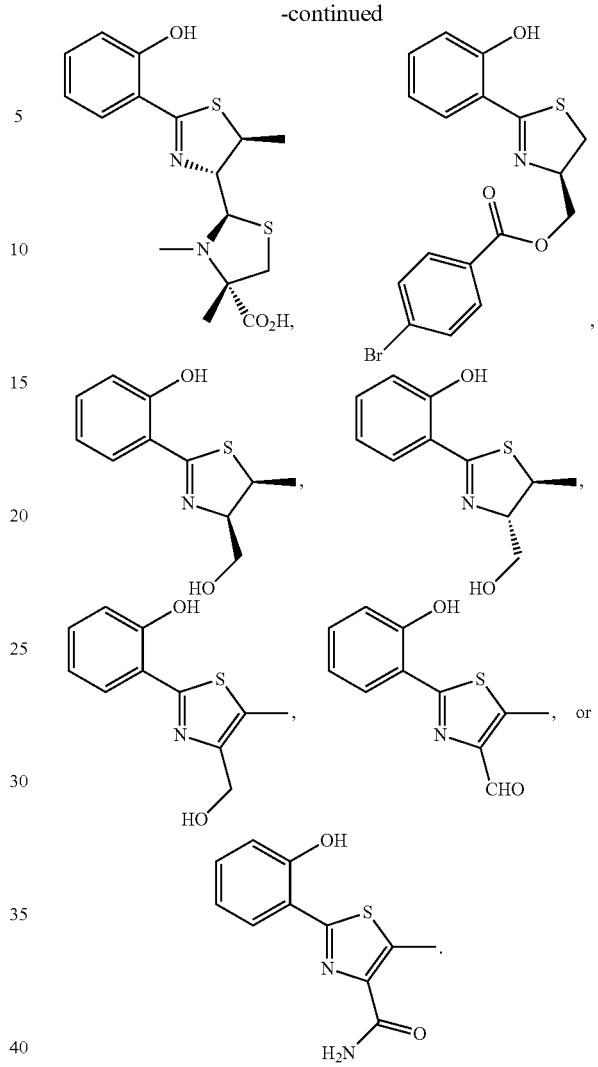

In a still further aspect, the compound is not:

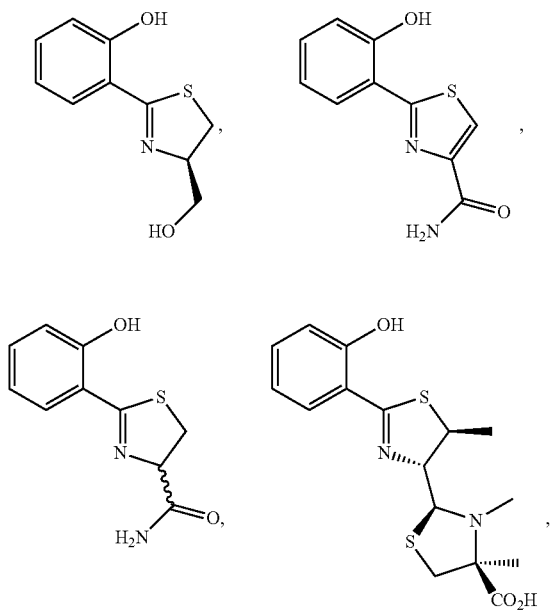

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carriers) followed by chilling and shaping in moulds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In the treatment conditions which require negative allosteric modulation of metabotropic glutamate receptor activity an appropriate dosage level will generally be about 0.01 to 500 mg per kg patient body weight per day and can be administered in single or multiple doses. Preferably, the dosage level will be about 0.1 to about 250 mg/kg per day; more preferably 0.5 to 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the from of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

The disclosed pharmaceutical compositions can further comprise other therapeutically active compounds, as discussed further herein, which are usually applied in the treatment of the above mentioned pathological conditions.

It is understood that the disclosed compositions can be prepared from the disclosed compounds. It is also understood that the disclosed compositions can be employed in the disclosed methods of using.

E. KITS

In one aspect, the invention relates to a kit comprising at least one disclosed compound and one or more of at least one agent known to modulate calcium release; at least one agent known to modulate calcium release; at least one agent known to treat a neurological and/or psychiatric disorder; or instructions for treating a disorder associated with calcium release. In a further aspect, the at least one compound or the at least one product and the at least one agent are co-formulated. In a further aspect, the at least one compound or the at least one product and the at least one agent are co-packaged.

In one aspect, the invention relates to kits comprising at least one compound having a structure represented by a formula:

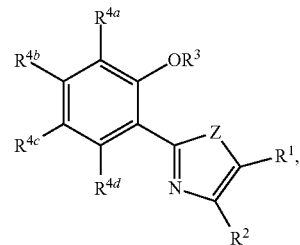

wherein ----- is an optional covalent bond, wherein valency is satisfied; wherein Z is selected from O and S; wherein $R^1$ is selected from hydrogen and optionally substituted C1-C6 alkyl; wherein $R^2$ is selected from nitrile, formyl, optionally substituted heteroaryl, optionally substituted heterocycloalkyl, optionally substituted alkoxyl, optionally substituted thioalkyl, optionally substituted alkylsulfonyl, optionally substituted alkylamino, thioamido, alkoxycarbonyl, carboxamide, amino-carbonyl, and alkylamine-carbonyl; wherein $R^3$ is selected from hydrogen and optionally substituted C1-C6 alkyl; wherein each of $R^{4a}$, $R^{4b}$, $R^{4c}$, and $R^{4d}$ is independently selected from hydrogen, halogen, hydroxyl, nitrile, nitro, thiol, formyl, optionally substituted amino, optionally substituted aryl, optionally substituted heteroaryl, optionally substituted alkoxyl, optionally substituted thioalkyl, optionally substituted alkylsulfinyl, optionally substituted alkylsulfonyl, optionally substituted alkylamino, thioamido, amidosulfonyl, alkoxycarbonyl, carboxamide, amino-carbonyl, alkylamine-carbonyl, and optionally substituted C1-C6 alkyl; or a pharmaceutically acceptable salt thereof.

In a further aspect, the compound has a structure represented by a formula:

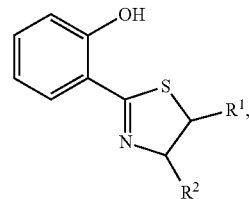

wherein $R^1$ is selected from hydrogen and optionally substituted C1-C6 alkyl; wherein $R^2$ is selected from nitrile, formyl, optionally substituted C1-C6 alkyl, optionally substituted heteroaryl, optionally substituted heterocycloalkyl, optionally substituted alkoxyl, optionally substituted thioalkyl, optionally substituted alkylsulfonyl, optionally substituted alkylamino, thioamido, alkoxycarbonyl, carboxamide, amino-carbonyl, and alkylamine-carbonyl; or a pharmaceutically acceptable salt thereof.

In a further aspect, the compound has a structure represented by a formula:

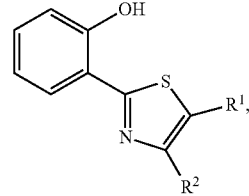

wherein R¹ is selected from hydrogen and optionally substituted C1-C6 alkyl; wherein R² is selected from nitrile, formyl, optionally substituted heteroaryl, optionally substituted heterocycloalkyl, optionally substituted alkoxyl, optionally substituted thioalkyl, optionally substituted alkylsulfonyl, optionally substituted alkylamino, thioamido, alkoxycarbonyl, carboxamide, amino-carbonyl, and alkylamine-carbonyl; or a pharmaceutically acceptable salt thereof.

In one aspect, the compound is selected from:

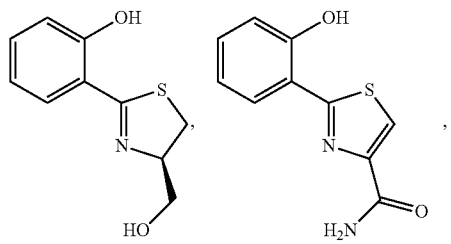

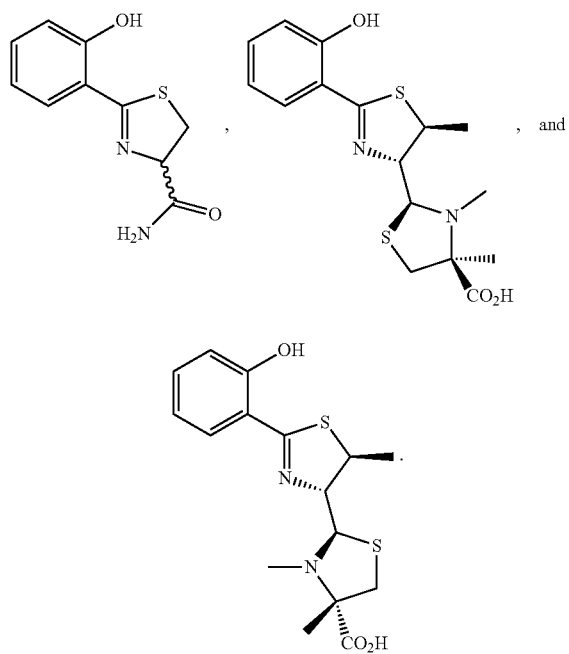

In a further aspect, the compound is selected from:

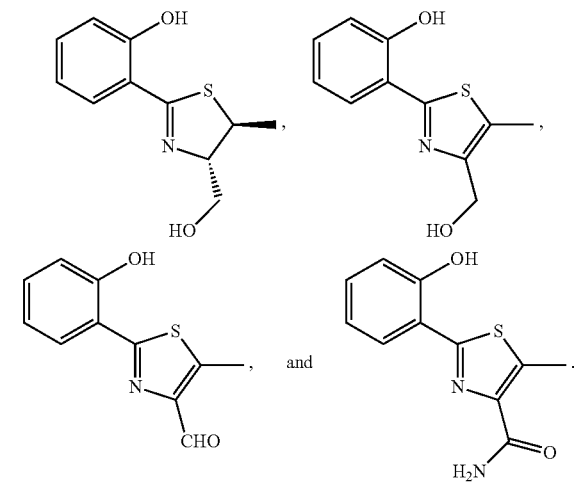

In a still further aspect, the compound is not:

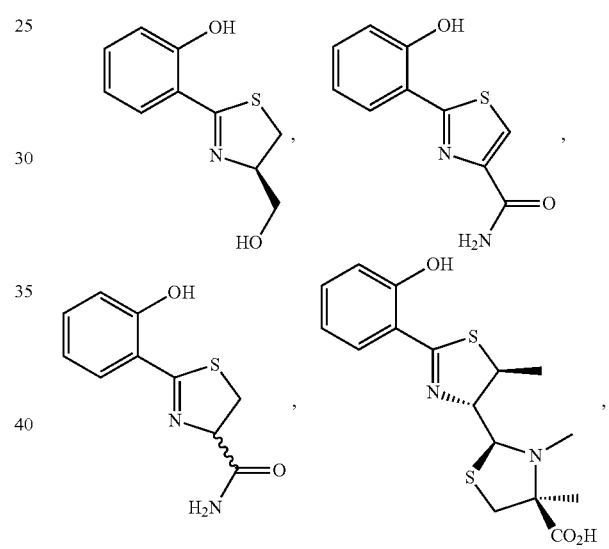

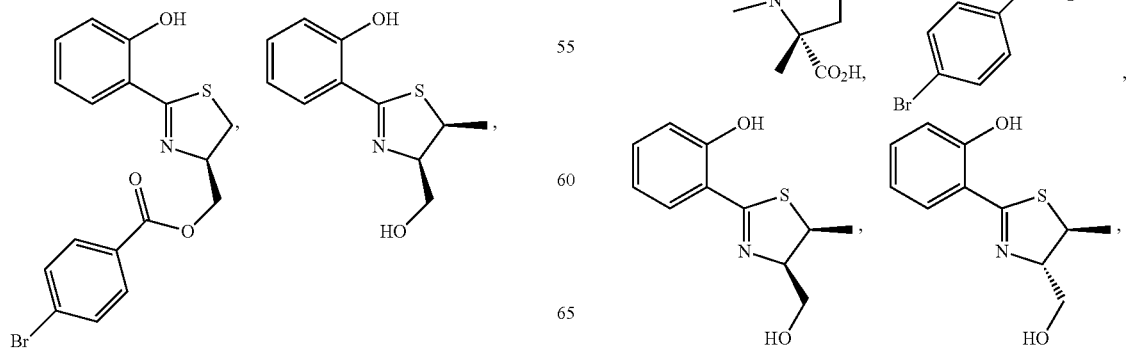

-continued

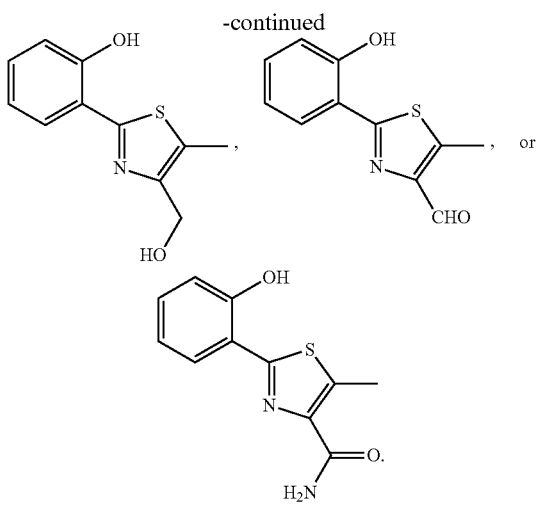

In a further aspect, the at least one compound or the at least one product and the at least one agent are co-formulated. In a further aspect, the at least one compound or the at least one product and the at least one agent are co-packaged.

It is understood that the disclosed kits can be prepared from the disclosed compounds. It is also understood that the disclosed compositions can be employed in the disclosed methods of using.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is contemplated that the disclosed kits can be used in connection with the disclosed methods of using, and/or the disclosed compositions.

F. METHODS OF USING THE COMPOUNDS AND COMPOSITIONS

Also provided are methods of use of a disclosed compounds, compositions, and medicaments. The pharmaceutical compositions and methods of the present invention can further comprise other therapeutically active compounds as noted herein which are usually applied in the treatment of the above mentioned pathological conditions.

1. 5HT-2B Receptors

Serotonin receptors, also known as 5-hydroxytryptamine receptors or 5-HT receptors, are a family of G protein-coupled receptors (GPCRs) and ligand-gated ion channels (LGICs) found in the central and peripheral nervous systems. They mediate both excitatory and inhibitory neurotransmission. The serotonin receptors are activated by the neurotransmitter serotonin, which acts as their natural ligand.

The 5HT-2B receptors, previously known as 5HT-2F receptors, are a specific a member of the larger family of 5-HT receptors. This sub-type is located primarily in the stomach fundus, uterus, vascular endothelial and vascular and GI smooth muscle, with little limited distribution in the brain. 5HT-2B receptor activity is via its action by association with G proteins that activate a phosphatidylinositol-calcium second messenger system.

The roles for the 5HT-2B receptor include, but are not limited to, regulation of differentiation and proliferation of the embryonic and adult heart, gastrointestinal contraction and endothelium-dependent relaxation. Drugs that specifically and potently bind this receptor, and activate or inhibit this receptor are need to study 5HT-2B's effects and potential utility for treating a variety of diseases and disorders such has heart disease, birth defects, and psychiatric disorders including schizophrenia, and depression. The 5HT-2B receptor is also associated with disease states including, but are not limited to, migraine, pain (e.g. acute, chronic, neuropathic, inflammatory and cancer pain) hypertension, disorders of the gastrointestinal tract (e.g., irritable bowel syndrome, hypertonic lower esophageal sphincter, motility disorders), restenosis, asthma and obstructive airway disease, prostatic hyperplasia (e.g., benign prostatic hyperplasia), and priapism.

The distribution and activity of 5HT-2B receptor antagonists indicate that they can be selective for diseased pulmonary vasculature (i.e., vessels affected by hypoxic conditions) compared to normal pulmonary and systemic vessels. Due to this selectivity, 5HT-2B antagonists can have therapeutic advantage over the available agents for the treatment of pulmonary hypertension. 5HT-2B antagonists can be used for treatment of migraine headaches. For example, RS-127,445 was tested in humans up to Phase I for this therapeutic indication. More recent research has focused on possible application of 5HT-2B antagonists as treatments for chronic heart disease.

Because of the similarities in the pharmacology of ligand interactions at 5HT-2B and 5HT-2C receptors, many of the therapeutic targets that have been proposed for 5HT-2C receptor antagonists are also targets for 5HT-2B receptor antagonists. Current evidence supports a therapeutic role for 5HT-2B and/or 5HT-2C receptor antagonists in treating anxiety (e.g., generalized anxiety disorder, panic disorder and obsessive compulsive disorder), alcoholism and addiction to other drugs of abuse, depression, migraine, sleep disorders, feeding disorders (e.g., anorexia nervosa) and priapism. Additionally, current evidence supports a therapeutic role for selective 5HT-2B receptor antagonists that will offer distinct therapeutic advantages collectively in efficacy, rapidity of onset and absence of side effects. Such gents are expected to be useful in the treatment of hypertension, disorders of the gastrointestinal track (e.g., irritable bowel syndrome, hypertonic lower esophageal sphincter, motility disorders), restenosis, asthma and obstructive airway disease, and prostatic hyperplasia (e.g., benign prostatic hyperplasia).

Experimental evidence indicates that the compound of the present invention are useful in the treatment of pain, including acute, chronic, neuropathic, inflammatory, and cancer pain, particularly inflammatory pain. 5-HT (serotonin) plays a key role in the regulation of transmission of nociceptive information at various levels of the peripheral and central nervous systems (see Richardson B. P. 1990 Ann NY Acad Sci 600:511-520). Moreover, neuronal systems containing 5-HT are involved not only in the regulation of nociceptive input at the spinal and supraspinal level, but in mediating the nociceptive action of other analgesics including the opiates. 5-HT is a mediator of sensitization of nerve terminal nociceptors that may occur in the genesis of pain associated with inflammation. The 5HT-2B receptor is highly sensitive to activation by 5-HT and specific blockade by selective 5-HT 2B antagonists may provide a novel avenue toward analgesia therapy.

Experimental evidence supports a therapeutic role for 5HT-2B receptor antagonists in treating hypertension. In hypertension, one of the most profound increases in vascular responsiveness is observed for serotonin. Two lines of evidence imply that this results from a switch in the receptor mediating vasoconstriction from predominantly 5HT-2A to predominantly 5HT-2B. First, serotonin induced contractions of isolated blood vessels from hypertensive animals become resistant to block by selective 5HT-2A receptor antagonists, but remain sensitive to non-selective 5HT-2B receptor antagonists. Second, there is an increase in 5HT-2B receptor mRNA in vessels from hypertensive animals (Watts et al. 1996 J Pharmacol Exp Ther 277:1103-13; and Watts et al. 1995 Hypertension 26:1056-1059). This hypertension-induced shift in the population of receptor subtype mediating constrictor responses to 5-HT suggests that selective block of vasoconstrictor 5HT-2B receptor may be of therapeutic benefit in the treatment of hypertension.

Clinical and experimental evidence supports a therapeutic role for 5HT-2B receptor antagonists in treating disorders of the gastrointestinal tract, in particular irritable bowel syndrome (IBS). Although the pathology underlying IBS remains unclear, there is a well-established implied role for the involvement of serotonin. Thus, meals with a high serotonin content can exacerbate symptoms in some patients (Lessorf 1985 Scand J Gastroenterology 109:117-121), while in pre-clinical studies, serotonin has been shown directly to sensitize visceral sensory neurons resulting in an enhanced pain response similar to that observed in IBS (Christian et al. 1989 J Applied Physiol 67:584-591; Sanger et al. 1996 Neurogastroenterology and Motility 8:319-331). The possibility that 5HT-2B receptor play a crucial role in the sensitizing actions of serotonin are suggested by several lines of evidence. Firstly, 5HT-2B receptor are present in the human intestine (Borman et al. 1995 Brit J Pharmacol 114:1525-1527; Borman et al. 1997 Ann of the New York Acad of Sciences 812:222-223). Secondly, activation of 5HT-2B receptor can result in the production of nitric oxide, an agent capable of sensitizing sensory nerve fibers (Glusa et al. 1993 Naunyn-Schmied Arch Pharmacol 347:471-477; Glusa et al. 1996 Brit J Pharmacol 119:330-334). Thirdly, poorly selective drugs which display high affinity for the 5HT-2B receptor are clinically effective in reducing the pain associated with IBS and related disorders (Symon et al. 1995 Arch Disease in Childhood 72:48-50; Tanum et al. 1996 Scand J Gastroenterol 31:318-325). Together these findings suggest that a selective 5HT-2B receptor antagonist will attenuate both the gastrointestinal pain and abnormal motility associated with IBS.

Clinical and experimental evidence supports a therapeutic role for 5HT-2B receptor antagonists in treating restenosis. Angioplasty and bypass grafting are associated with restenosis which limits the efficacy of these procedures. Platelet-rich thrombus formation is the predominant cause of acute occlusion whereas serotonin, among other platelet-derived mediators, is thought to contribute to late restenosis (Barradas et al. 1994 Clinica Chim Acta 230:157-167). This late restenosis involves proliferation of the vascular smooth muscle. Two lines of evidence implicate a role for 5HT-2B receptor in this process. Firstly, serotonin displays a potent mitogenic activity in cultured smooth muscle and endothelial cells via activation of 5-HT 2 receptors (Pakala et al. 1994 Circulation 90:1919-1926). Secondly, this mitogenic activity appears to be mediated via activation of a tyrosine kinase second messenger pathway involving mitogen activated protein kinase (MAPK) (Lee et al. 1997 Am J Physiol 272(1 pt 1):C223-230; Kelleher et al. 1995 Am J Physiol 268(6 pt 1):L894-901). The recent demonstration that 5HT-2B receptor couple to MAPK (Nebigil et al. 2000 PNAS USA 97:22591-2596), coupled with the high affinity of serotonin for this receptor subtype, indicates that a selective 5HT-2B receptor antagonist may offer protection against restenosis of autografted blood vessels or of vessels following angioplasty.

Clinical and experimental evidence supports a therapeutic role for 5HT-2B receptor antagonists in treating asthma and obstructive airway disease. Abnormal proliferation of airways smooth muscle, together with hyper-reactivity of the smooth muscle to constrictor stimuli including serotonin, plays a significant role in the pathogenesis of human airway disease such as asthma and bronchial pulmonary dysplasia (James et al. 1989 Am Review of Respiratory Disease 139:242-246; Margraf et al. 1991 Am Review of Respiratory Disease 143:391-400). In addition to other subtypes of serotonin receptor, 5HT-2B receptor are present in bronchial smooth muscle (Choi et al. 1996 FEBS Lett 391:45-51) and have been shown to stimulate smooth muscle mitogenesis in airways smooth muscle (Lee et al. 1994 Am J Physiol 266:L46-52). Since elevated concentrations of circulating free serotonin are closely associated with clinical severity and pulmonary function in symptomatic asthmatics, serotonin may play an important role in the pathophysiology of acute attacks (Lechin et al. 1996 Ann Allergy Asthma Immunol 77:245-253). These data suggest that an antagonist of 5HT-2B receptor in airways smooth muscle may therefore be useful in preventing airways constriction resulting from the elevated levels of circulating serotonin and prevent proliferation of the airways smooth muscle that contributes to the long-term pathology of this disease.

Experimental evidence supports a therapeutic role for 5HT-2B receptor antagonists in treating prostatic hyperplasia. Obstruction of the urinary tract can occur as a result of prostatic hyperplasia and excessive prostatic constriction of the urethra. This in turn leads to diminished urinary flow rates and an increased urgency and frequency of urination. 5HT-2B receptor are present in the human prostate (Kursar et al. 1994 Mol Pharmacol 46:227-234) and a receptor with the pharmacological attributes of this receptor subtype mediates contraction of the tissue (Killam et al. 1995 Eur J Pharmacol 273:7-14). Some drugs effective in the treatment of benign prostatic hyperplasia block 5-HT mediated contractions of the prostate (Noble et al. 1997 Brit J Pharmacol 120:231-238). 5HT-2B receptor mediate smooth muscle and fibrotic hyperplasia (Launay et al. 1996 J Biol Chem 271:3141-3147) and serotonin is mitogenic in the prostate (Cockett et al. 1993 Urology 43:512-519), therefore a selective 5HT-2B receptor antagonist may have utility not only in mitigating the excessive prostatic constriction, but also in preventing progression of tissue hyperplasia.

Experimental evidence supports a therapeutic role for 5-HT 2C receptor antagonists in treating priapism (Kennett 1993 Curr Opin Invest Drugs 2:317-362). MCPP produces penile erections in rats, which effect is blocked by non-selective 5-HT 2C/2A/2B receptor antagonists but not by selective 5-HT 2A receptor antagonists (Hoyer 1989 Peripheral actions of 5-HT Fozard J. ed., Oxford University Press, Oxford, 72-99). This therapeutic target for 5-HT 2C receptor antagonists is equally a target for 5HT-2B receptor antagonists.

2. Histamine H1 Receptors

The H1 receptor is a histamine receptor belonging to the family of G-protein-coupled receptors. This receptor, which is activated by the biogenic amine histamine, is expressed throughout the body, to be specific, in smooth muscles, on vascular endothelial cells, in the heart, and in the central nervous system. The H1 receptor is linked to an intracellular G-protein (Gq) that activates phospholipase C and the phosphatidylinositol (PIP2) signaling pathway. Based on the number of drugs available on market it is the most clinically important molecular drug target.

Histamine H1 receptors are activated by endogenous histamine, which is released by neurons that have their cell bodies in the tuberomamillary nucleus of the hypothalamus. The histaminergic neurons of the tuberomammillary nucleus become active during the 'wake' cycle, firing at approximately 2 Hz; during slow wave sleep, this firing rate drops to approximately 0.5 Hz. Finally, during REM sleep, histaminergic neurons stop firing altogether. It has been reported that histaminergic neurons have the most wake-selective firing pattern of all known neuronal types.

In the cortex, activation of H1 receptors leads to inhibition of cell membrane potassium channels. This depolarizes the neurons and increases the resistance of the neuronal cell membrane, bringing the cell closer to its firing threshold and increasing the excitatory voltage produced by a given excitatory current. H1 receptor antagonists, or antihistamines, produce drowsiness because they oppose this action, reducing neuronal excitation.

3. Kappa Opioid Receptor

The kappa opioid receptor is a type of opioid receptor which binds the opioid peptide dynorphin as the primary endogenous ligand. These receptors are receptors are widely distributed in the brain (hypothalamus, periaqueductal gray, and claustrum), spinal cord (substantia gelatinosa), and in pain neurons. The receptors belong to the superfamily of G protein-coupled receptors (GPCR), postulated to possess seven helical transmembrane (7TM) spanning regions, they are now known to be anatomically distributed in both the central and peripheral nervous systems and aside from modulation of pain are intimately involved in a diversity of biological events ranging from of the modulation of immune response to hibernation.

The modulation of the kappa opioid receptor has therapeutic utility in disease states including, but are not limited to, migraines, arthritis, allergy, viral infections, diarrhea, psychosis, schizophrenia, depression, stress, anxiety, uropathy, addiction, and obesity. Experimental evidence also indicates that kappa opioid antagonists can be useful as cytostatic, immunomodulatory, immunosuppressive, anti-tussive, hypotensive agents, anti-diuretic, stimulatory and anti-convulsant agents. Additionally, the inhibition of the kappa opioid receptor can be useful in the treatment of Parkinson's disease as an adjunct to L-dopa for treatment of dyskinesia associated with the L-dopa treatment.

In terms of substance abuse treatment, experimental evidence indicates that that the endogenous kappa opioid system opposes the actions of mu agonists, suggesting that antagonists selective for the kappa receptor could suppress or eliminate the symptoms of withdrawal which arise from an overactive kappa receptor system and thus could promote abstinence and prevent relapse. Selective pharmacological kappa receptor antagonism or genetic deletion of kappa receptors has been shown to decrease ethanol self-administration in animal models of alcoholism. These data further suggest that a pharmaceutical agent which is a selective antagonist for the kappa versus mu and delta opioid receptors could fill a significant need in ethanol use disorder therapy.

4. Modulation of Calcium Release

The compounds and pharmaceutically acceptable derivatives thereof that are disclosed herein, modulate calcium release. That is, the disclosed compounds and pharmaceutically acceptable derivatives thereof that are disclosed herein modulate, among other things, calcium release in a mammal. Thus in one aspect, the invention relates to a method for treating a disorder related to calcium release in a mammal, the method comprising the step of administering to a mammal an effective amount of at least one compound having a structure represented by a formula:

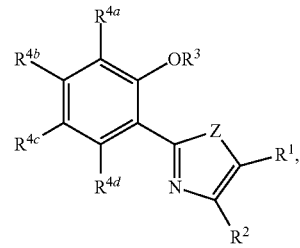

wherein ----- is an optional covalent bond, wherein valency is satisfied; wherein Z is selected from O and S; wherein $R^1$ is selected from hydrogen and optionally substituted C1-C6 alkyl; wherein $R^2$ is selected from nitrile, formyl, optionally substituted heteroaryl, optionally substituted heterocycloalkyl, optionally substituted alkoxyl, optionally substituted thioalkyl, optionally substituted alkylsulfonyl, optionally substituted alkylamino, thioamido, alkoxycarbonyl, carboxamide, amino-carbonyl, and alkylamine-carbonyl; wherein $R^3$ is selected from hydrogen and optionally substituted C1-C6 alkyl; wherein each of $R^{4a}$, $R^{4b}$, $R^{4c}$, and $R^{4d}$ is independently selected from hydrogen, halogen, hydroxyl, nitrile, nitro, thiol, formyl, optionally substituted amino, optionally substituted aryl, optionally substituted heteroaryl, optionally substituted alkoxyl, optionally substituted thioalkyl, optionally substituted alkylsulfinyl, optionally substituted alkylsulfonyl, optionally substituted alkylamino, thioamido, amidosulfonyl, alkoxycarbonyl, carboxamide, amino-carbonyl, alkylamine-carbonyl, and optionally substituted C1-C6 alkyl; or a pharmaceutically acceptable salt thereof.

In a further aspect, the compound has a structure represented by a formula:

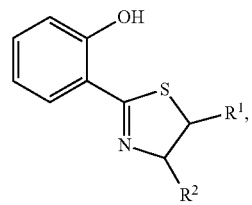

wherein $R^1$ is selected from hydrogen and optionally substituted C1-C6 alkyl; wherein $R^2$ is selected from nitrile, formyl, optionally substituted C1-C6 alkyl, optionally substituted heteroaryl, optionally substituted heterocycloalkyl, optionally substituted alkoxyl, optionally substituted thioalkyl, optionally substituted alkylsulfonyl, optionally substituted alkylamino, thioamido, alkoxycarbonyl, carboxamide, amino-carbonyl, and alkylamine-carbonyl; or a pharmaceutically acceptable salt thereof.

In a further aspect, the compound has a structure represented by a formula:

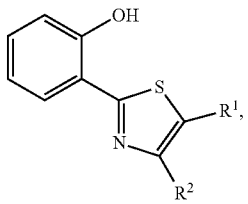

wherein $R^1$ is selected from hydrogen and optionally substituted C1-C6 alkyl; wherein $R^2$ is selected from nitrile, formyl, optionally substituted heteroaryl, optionally substituted heterocycloalkyl, optionally substituted alkoxyl, optionally substituted thioalkyl, optionally substituted alkylsulfonyl, optionally substituted alkylamino, thioamido, alkoxycarbonyl, carboxamide, amino-carbonyl, and alkylamine-carbonyl; or a pharmaceutically acceptable salt thereof.

In one aspect, the compound is selected from:

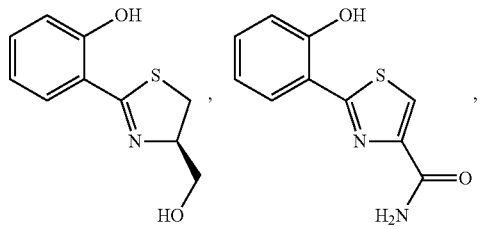

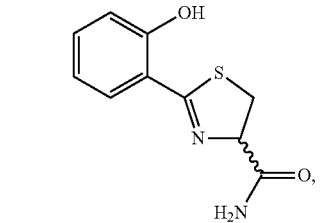

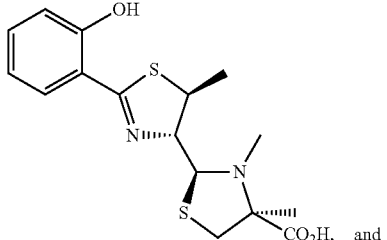

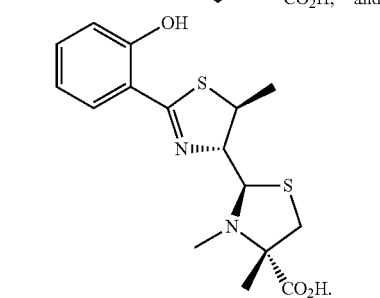

In a further aspect, the compound is selected from:

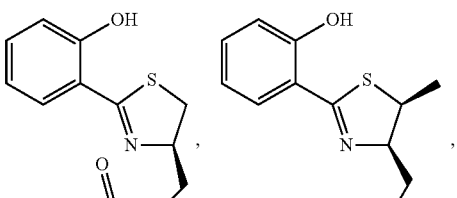

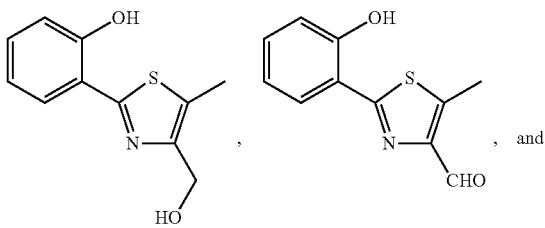

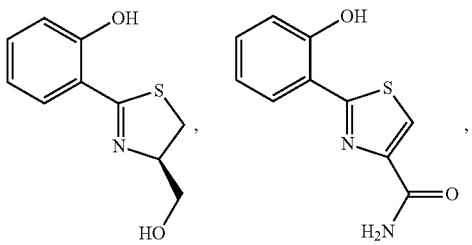

In a still further aspect, the compound is not:

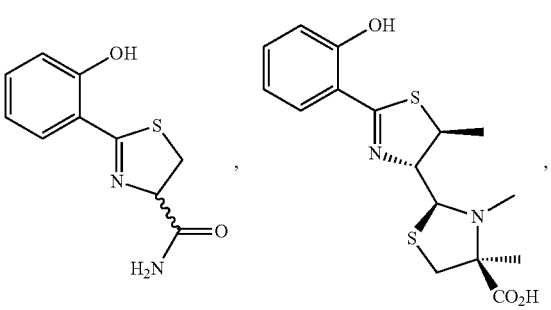

-continued

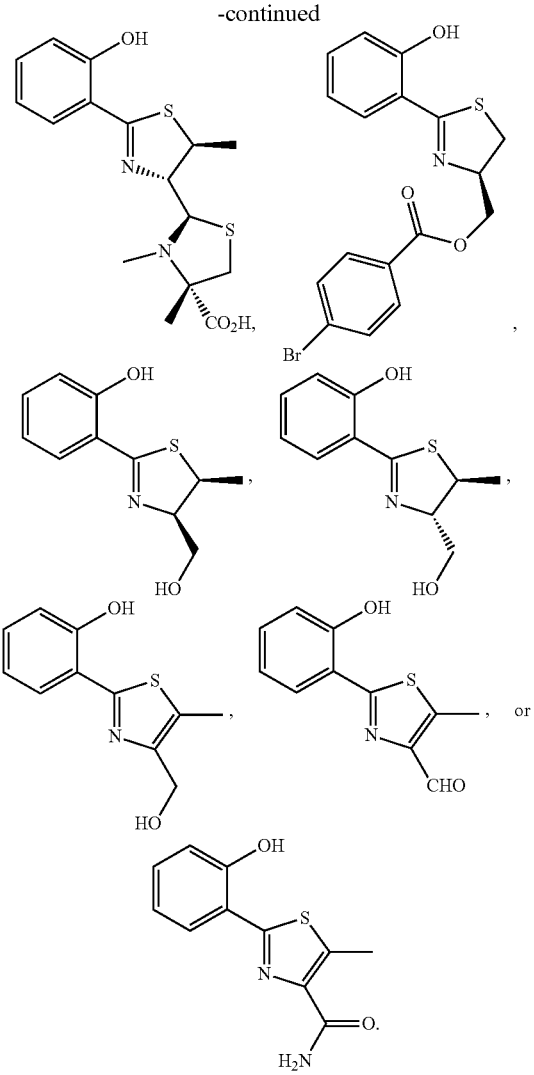

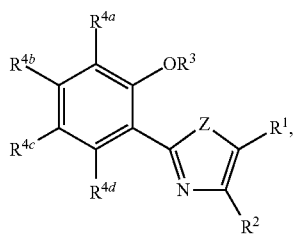

In a further aspect, the invention relates to a method for modulating calcium release activity in a mammal, the method comprising the step of administering to the mammal an effective amount of least one compound having a structure represented by a formula:

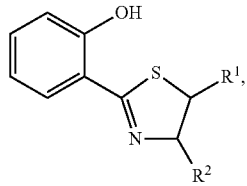

wherein ----- is an optional covalent bond, wherein valency is satisfied; wherein Z is selected from O and S; wherein $R^1$ is selected from hydrogen and optionally substituted C1-C6 alkyl; wherein $R^2$ is selected from nitrile, formyl, optionally substituted heteroaryl, optionally substituted heterocycloalkyl, optionally substituted alkoxyl, optionally substituted thioalkyl, optionally substituted alkylsulfonyl, optionally substituted alkylamino, thioamido, alkoxycarbonyl, carboxamide, amino-carbonyl, and alkylamine-carbonyl; wherein $R^3$ is selected from hydrogen and optionally substituted C1-C6 alkyl; wherein each of $R^{4a}$, $R^{4b}$, $R^{4c}$, and $R^{4d}$ is independently selected from hydrogen, halogen, hydroxyl, nitrile, nitro, thiol, formyl, optionally substituted amino, optionally substituted aryl, optionally substituted heteroaryl, optionally substituted alkoxyl, optionally substituted thioalkyl, optionally substituted alkylsulfinyl, optionally substituted alkylsulfonyl, optionally substituted alkylamino, thioamido, amidosulfonyl, alkoxycarbonyl, carboxamide, amino-carbonyl, alkylamine-carbonyl, and optionally substituted C1-C6 alkyl; or a pharmaceutically acceptable salt thereof.

In a further aspect, the compound has a structure represented by a formula:

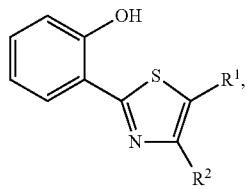

wherein $R^1$ is selected from hydrogen and optionally substituted C1-C6 alkyl; wherein $R^2$ is selected from nitrile, formyl, optionally substituted C1-C6 alkyl, optionally substituted heteroaryl, optionally substituted heterocycloalkyl, optionally substituted alkoxyl, optionally substituted thioalkyl, optionally substituted alkylsulfonyl, optionally substituted alkylamino, thioamido, alkoxycarbonyl, carboxamide, amino-carbonyl, and alkylamine-carbonyl; or a pharmaceutically acceptable salt thereof.

In a further aspect, the compound has a structure represented by a formula:

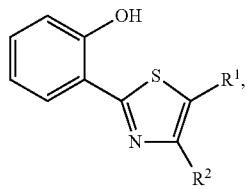

wherein $R^1$ is selected from hydrogen and optionally substituted C1-C6 alkyl; wherein $R^2$ is selected from nitrile, formyl, optionally substituted heteroaryl, optionally substituted heterocycloalkyl, optionally substituted alkoxyl, optionally substituted thioalkyl, optionally substituted alkylsulfonyl, optionally substituted alkylamino, thioamido, alkoxycarbonyl, carboxamide, amino-carbonyl, and alkylamine-carbonyl; or a pharmaceutically acceptable salt thereof.

In one aspect, the compound is selected from:

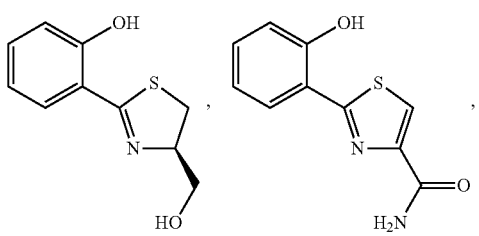

-continued
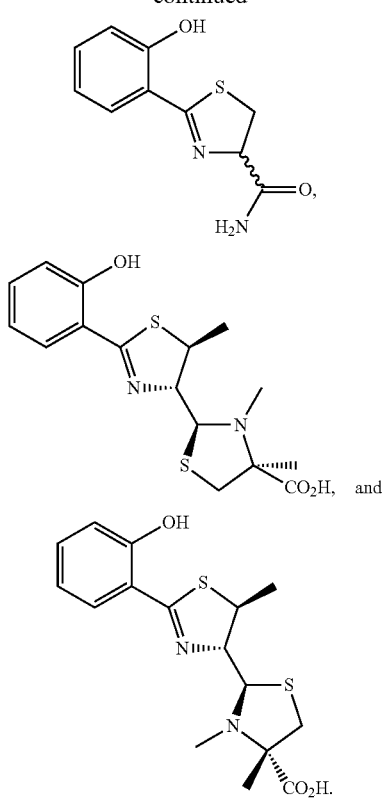
In a further aspect, the compound is selected from:
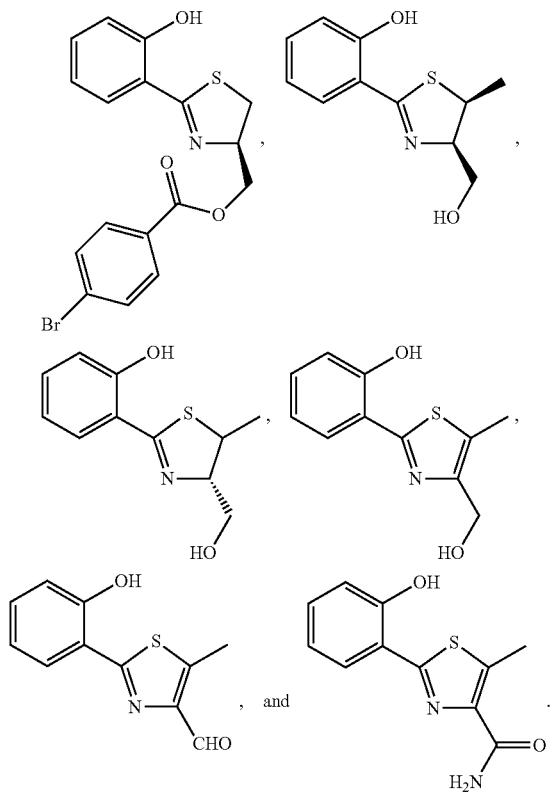
In a still further aspect, the compound is not:
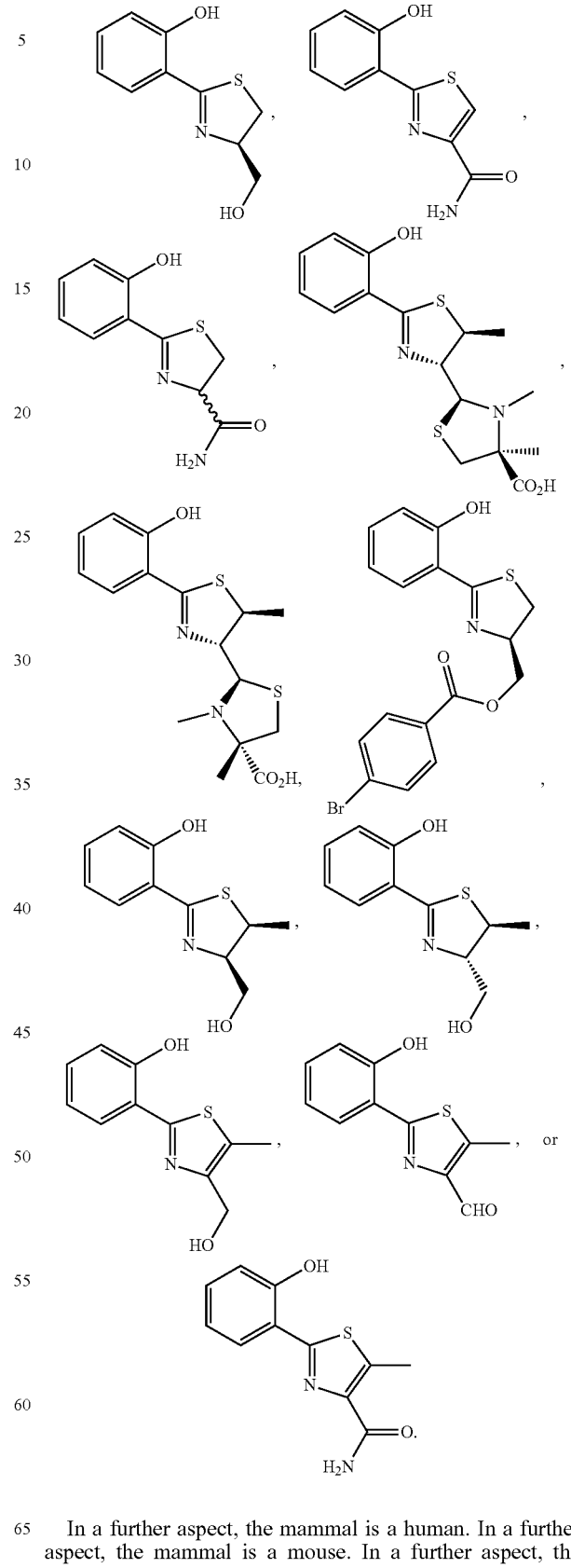
In a further aspect, the mammal is a human. In a further aspect, the mammal is a mouse. In a further aspect, the mammal has been diagnosed with a need for treatment of the disorder prior to the administering step. In a further aspect, the method further comprises the step of identifying a mammal in need of treatment of the disorder.

In a further aspect, the invention relates to a method for modulating calcium release activity in a mammalian cell, the method comprising the step of administering to the cell an effective amount of least one compound having a structure represented by a formula:

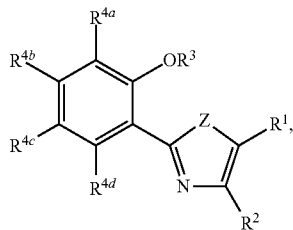

wherein ----- is an optional covalent bond, wherein valency is satisfied; wherein Z is selected from O and S; wherein $R^1$ is selected from hydrogen and optionally substituted C1-C6 alkyl; wherein $R^2$ is selected from nitrile, formyl, optionally substituted heteroaryl, optionally substituted heterocycloalkyl, optionally substituted alkoxyl, optionally substituted thioalkyl, optionally substituted alkylsulfonyl, optionally substituted alkylamino, thioamido, alkoxycarbonyl, carboxamide, amino-carbonyl, and alkylamine-carbonyl; wherein $R^3$ is selected from hydrogen and optionally substituted C1-C6 alkyl; wherein each of $R^{4a}$, $R^{4b}$, $R^{4c}$, and $R^{4d}$ is independently selected from hydrogen, halogen, hydroxyl, nitrile, nitro, thiol, formyl, optionally substituted amino, optionally substituted aryl, optionally substituted heteroaryl, optionally substituted alkoxyl, optionally substituted thioalkyl, optionally substituted alkylsulfinyl, optionally substituted alkylsulfonyl, optionally substituted alkylamino, thioamido, amidosulfonyl, alkoxycarbonyl, carboxamide, amino-carbonyl, alkylamine-carbonyl, and optionally substituted C1-C6 alkyl; or a pharmaceutically acceptable salt thereof.

In a further aspect, the compound has a structure represented by a formula:

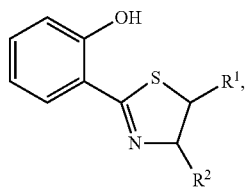

wherein $R^1$ is selected from hydrogen and optionally substituted C1-C6 alkyl; wherein $R^2$ is selected from nitrile, formyl, optionally substituted C1-C6 alkyl, optionally substituted heteroaryl, optionally substituted heterocycloalkyl, optionally substituted alkoxyl, optionally substituted thioalkyl, optionally substituted alkylsulfonyl, optionally substituted alkylamino, thioamido, alkoxycarbonyl, carboxamide, amino-carbonyl, and alkylamine-carbonyl; or a pharmaceutically acceptable salt thereof.

In a further aspect, the compound has a structure represented by a formula:

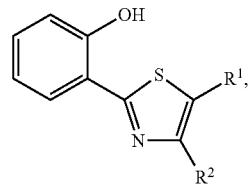

wherein $R^1$ is selected from hydrogen and optionally substituted C1-C6 alkyl; wherein $R^2$ is selected from nitrile, formyl, optionally substituted heteroaryl, optionally substituted heterocycloalkyl, optionally substituted alkoxyl, optionally substituted thioalkyl, optionally substituted alkylsulfonyl, optionally substituted alkylamino, thioamido, alkoxycarbonyl, carboxamide, amino-carbonyl, and alkylamine-carbonyl; or a pharmaceutically acceptable salt thereof.

In one aspect, the compound is selected from:

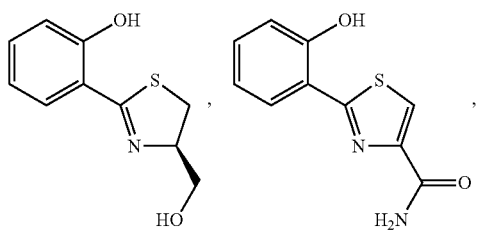

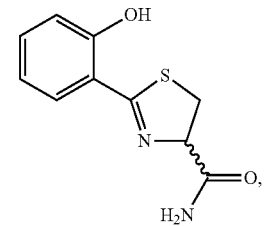

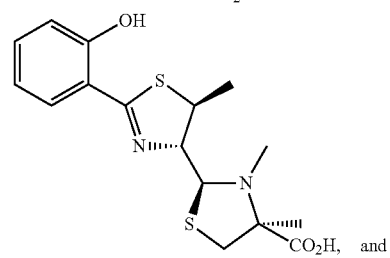

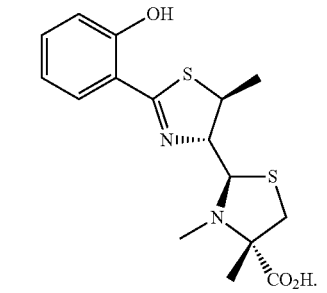

In a further aspect, the compound is selected from:

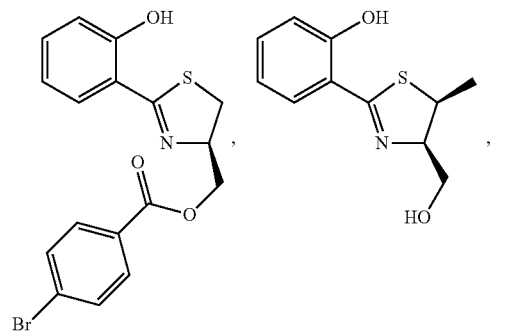

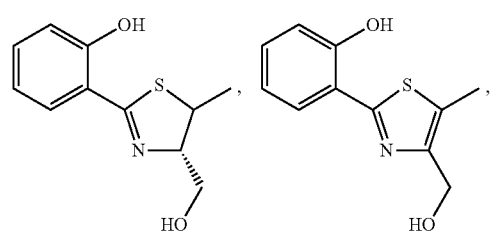

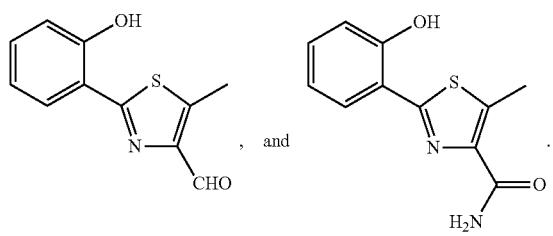

In a still further aspect, the compound is not:

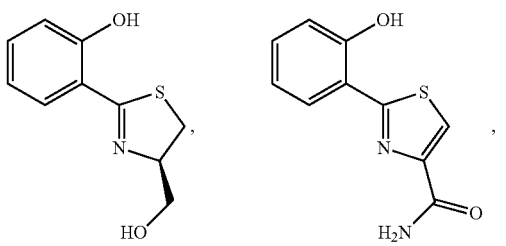

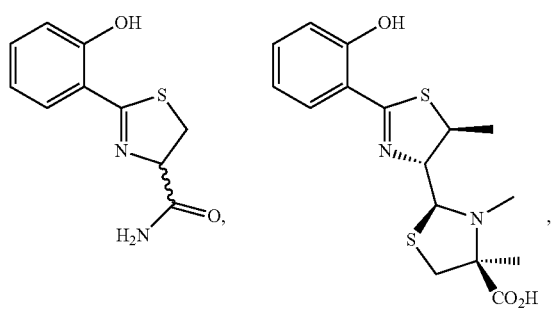

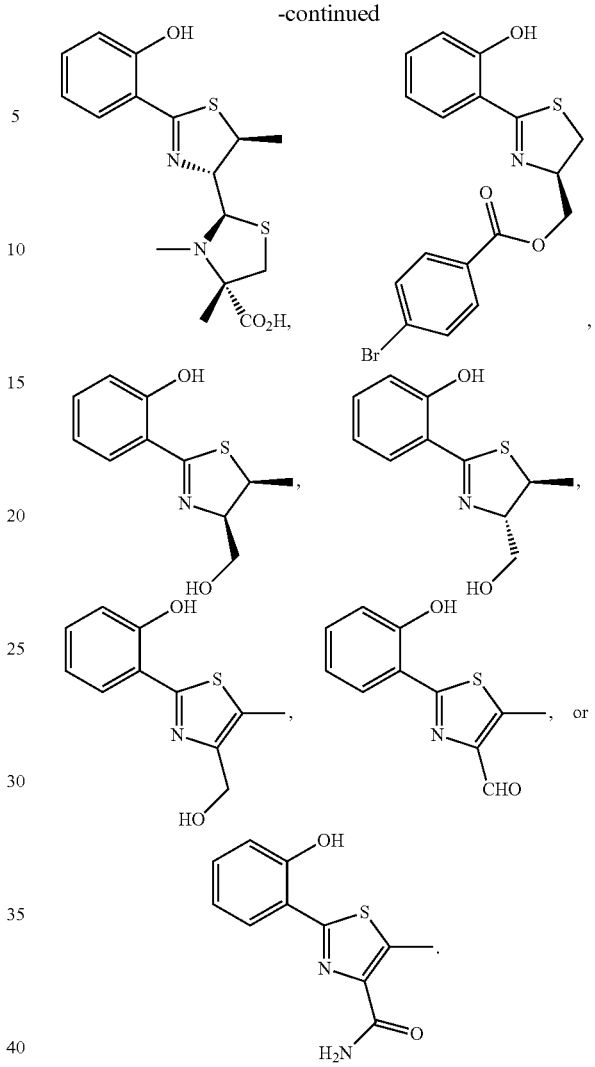

In a further aspect, the cell is a mouse dorsal root ganglion cell. In a further aspect, the cell has been isolated from the mammal prior to the administration step. In a further aspect, modulating is increasing. In a further aspect, modulating is decreasing.

In one aspect, the compounds, or pharmaceutically acceptable derivatives thereof, modulate calcium release. One way the disclosed compounds or pharmaceutically acceptable derivatives thereof achieve this action is through binding to a cellular protein. In a further aspect, the cellular protein is a cell surface receptor. In a yet further aspect, the activity of the cell surface receptor modulates, either directly or indirectly, calcium release from and/or calcium uptake into intracellular calcium stores. In a still further aspect, the cell surface receptor is a G-protein. In an even further aspect, the G-protein is selected from histamine H1 receptor, 5HT-2B receptor, and kappa opioid receptor. In a further aspect, the cellular protein is an intracellular protein.

In one aspect, the compound modulates the 5HT-2B receptor. In a further aspect, modulation of the 5HT-2B receptor modulates calcium release. In a still further aspect, modulation of the 5HT-2B receptor is negative. In a still further aspect, the modulation is antagonism. In a yet further aspect, the modulation is inhibition. In an even further aspect, modulation is negative allosteric modulation. In a further aspect, modulation is by direct inhibition. In a still further aspect, modulation is a indirect inhibition.

In one aspect, the compound modulates the 5HT-2B receptor. In a further aspect, modulation of the 5HT-2B receptor modulates calcium release. In a still further aspect, modulation of the 5HT-2B receptor is positive. In a still further aspect, the modulation is agonism. In a yet further aspect, the modulation is stimulation. In an even further aspect modulation is positive allosteric modulation. In a further aspect, modulation is by direct activation. In a still further aspect, activation is by indirect activation.

In one aspect, the compound modulates the histamine H1 receptor. In a further aspect, modulation of the histamine H1 receptor modulates calcium release. In a still further aspect, modulation of the histamine H1 receptor is negative. In a still further aspect, the modulation is antagonism. In a yet further aspect, the modulation is inhibition. In an even further aspect, modulation is negative allosteric modulation. In a further aspect, modulation is by direct inhibition. In a still further aspect, modulation is a indirect inhibition.

In one aspect, the compound modulates the histamine H1 receptor. In a further aspect, modulation of the histamine H1 receptor modulates calcium release. In a still further aspect, modulation of the histamine H1 receptor is positive. In a still further aspect, the modulation is agonism. In a yet further aspect, the modulation is stimulation. In an even further aspect modulation is positive allosteric modulation. In a further aspect, modulation is by direct activation. In a still further aspect, activation is by indirect activation.

In one aspect, the compound modulates the kappa opioid receptor. In a further aspect, modulation of the kappa opioid receptor modulates calcium release. In a still further aspect, modulation of the kappa opioid receptor is negative. In a still further aspect, the modulation is antagonism. In a yet further aspect, the modulation is inhibition. In an even further aspect, modulation is negative allosteric modulation. In a further aspect, modulation is by direct inhibition. In a still further aspect, modulation is a indirect inhibition.

In one aspect, the compound modulates the kappa opioid receptor. In a further aspect, modulation of the kappa opioid receptor modulates calcium release. In a still further aspect, modulation of the kappa opioid receptor is positive. In a still further aspect, the modulation is agonism. In a yet further aspect, the modulation is stimulation. In an even further aspect modulation is positive allosteric modulation. In a further aspect, modulation is by direct activation. In a still further aspect, activation is by indirect activation.

In a further aspect, the compound has an $EC_{50}$ of less than about 20 µM, less than about 10 µM, less than about 5 µM, or less than about 1 µM. In one aspect, the modulation is inhibition. In a further aspect, the compound has an $IC_{50}$ of less than about 20 µM, less than about 10 µM, less than about 5 µM, or less than about 1 µM.

It is understood and disclosed herein that the compounds disclosed herein are useful in treating a disorder in need of modulation of calcium release. In a further aspect, the compounds disclosed are useful in treating a disorder related to calcium release. In a further aspect, the compounds are useful in treating a disorder related to the 5HT-2B receptor. In a further aspect, the compounds are useful in treating a disorder related to the histamine H1 receptor. In a further aspect, the compounds are useful in treating a disorder related to the kappa opioid receptor.

In one aspect, the disorder is selected from motion sickness, emesis, post-operative nausea and vomiting (PONV), allergic disorders, allergic rhinitis, pruritus, psychiatric disorders, anxiety, neoplasia, cancer, periodontitis and osteoporosis, allergic conjunctivitis, ocular itching, allergic rhinitis, asthma, chronic urticaria, eczema dermatitis, prurigo, pruritis cutaneous, psoriasis vulgaris, erythema exsudativum multiforme, and an autoimmune disorder. In a further aspect, the autoimmune disorder is selected from rheumatoid arthritis, graft-versus host disease (GvHD), inflammatory bowel disease (IBD), insulin dependent diabetes mellitus (IDDM), multiple sclerosis, primary biliary cirrhosis, systemic sclerosis, psoriasis, autoimmune thyroiditis, and autoimmune thrombocytopenic purpura. In a yet further aspect, the autoimmune disorder is a Th1-mediated autoimmune disorder. In a still further, the Th1-mediated autoimmune disorder is multiple sclerosis.

In one aspect, the disorder is selected from anxiety, addiction, migraines, arthritis, allergy, viral infections, hypertension, diarrhea, psychosis, schizophrenia, depression, stress, anxiety, uropathy, addiction, ischemic trauma, L-dopa induced dyskinesia and obesity.

In one aspect, the disorder is selected from pulmonary hypertension, migraine, pain, hypertension, disorders of the gastrointestinal tract, restenosis, asthma, chronic heart disease, heart hypertrophy, obstructive airway disease, prostatic hyperplasia and priapism. In a further aspect, the pain disorder is selected from acute, chronic, neuropathic, inflammatory and cancer pain. In a still further aspect, the gastrointestinal tract disorder is selected from irritable bowel syndrome, hypertonic lower esophageal sphincter, and motility disorders. In a yet further aspect, prostatic hyperplasia disorder is selected from benign prostatic hyperplasia.

It is understood that the disclosed methods can be used in connection with the disclosed compounds, compositions, kits, and uses.

5. Manufacture of a Medicament

In one aspect, the invention relates to a method for the manufacture of a medicament for the treatment of a disorder related to calcium release in a mammal, comprising combining one or more compounds having a structure represented by a formula:

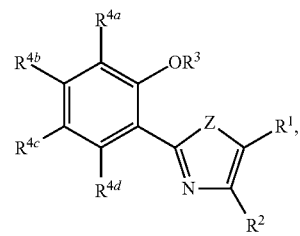

wherein ----- is an optional covalent bond, wherein valency is satisfied; wherein Z is selected from O and S; wherein $R^1$ is selected from hydrogen and optionally substituted C1-C6 alkyl; wherein $R^2$ is selected from nitrile, formyl, optionally substituted heteroaryl, optionally substituted heterocycloalkyl, optionally substituted alkoxyl, optionally substituted thioalkyl, optionally substituted alkylsulfonyl, optionally substituted alkylamino, thioamido, alkoxycarbonyl, carboxamide, amino-carbonyl, and alkylamine-carbonyl; wherein $R^3$ is selected from hydrogen and optionally substituted C1-C6 alkyl; wherein each of $R^{4a}$, $R^{4b}$, $R^{4c}$, and $R^{4d}$ is independently selected from hydrogen, halogen, hydroxyl, nitrile, nitro, thiol, formyl, optionally substituted amino, optionally substituted aryl, optionally substituted heteroaryl, optionally substituted alkoxyl, optionally substituted thioalkyl, optionally substituted alkylsulfinyl, optionally substituted alkylsulfonyl, optionally substituted alkylamino, thioamido, amidosulfonyl, alkoxycarbonyl, carboxamide, amino-carbonyl, alkylamine-carbonyl, and optionally substituted C1-C6 alkyl; or a pharmaceutically acceptable salt thereof.

In a further aspect, the compound has a structure represented by a formula:

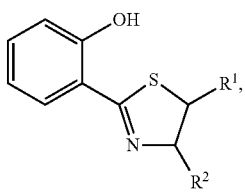

wherein $R^1$ is selected from hydrogen and optionally substituted C1-C6 alkyl; wherein $R^2$ is selected from nitrile, formyl, optionally substituted C1-C6 alkyl, optionally substituted heteroaryl, optionally substituted heterocycloalkyl, optionally substituted alkoxyl, optionally substituted thioalkyl, optionally substituted alkylsulfonyl, optionally substituted alkylamino, thioamido, alkoxycarbonyl, carboxamide, amino-carbonyl, and alkylamine-carbonyl; or a pharmaceutically acceptable salt thereof.

In a further aspect, the compound has a structure represented by a formula:

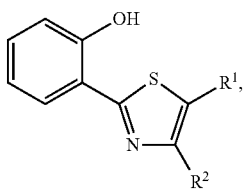

wherein $R^1$ is selected from hydrogen and optionally substituted C1-C6 alkyl; wherein $R^2$ is selected from nitrile, formyl, optionally substituted heteroaryl, optionally substituted heterocycloalkyl, optionally substituted alkoxyl, optionally substituted thioalkyl, optionally substituted alkylsulfonyl, optionally substituted alkylamino, thioamido, alkoxycarbonyl, carboxamide, amino-carbonyl, and alkylamine-carbonyl; or a pharmaceutically acceptable salt thereof.

In one aspect, the compound is selected from:

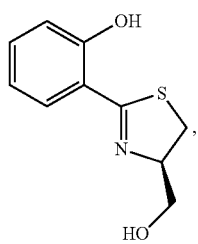, 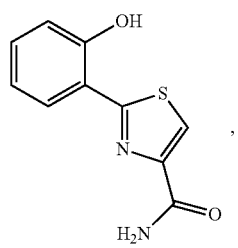, 

-continued

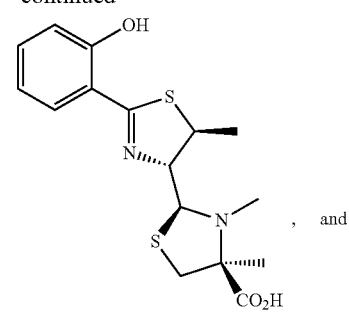

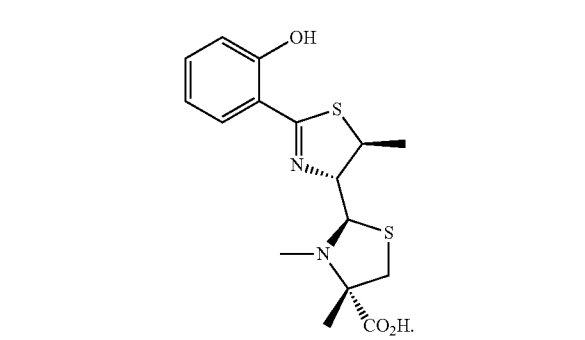, and

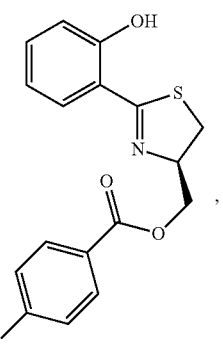

In a further aspect, the compound is selected from:

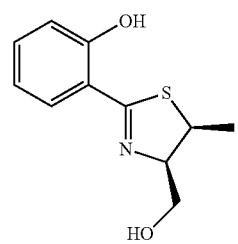

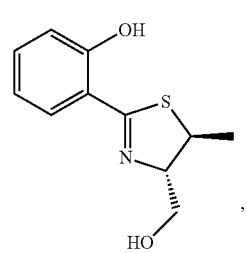, 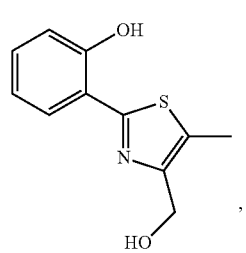

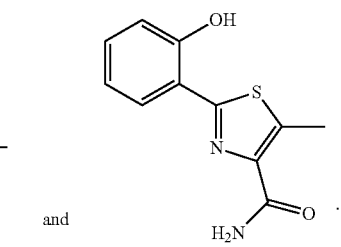.

In a still further aspect, the compound is not:

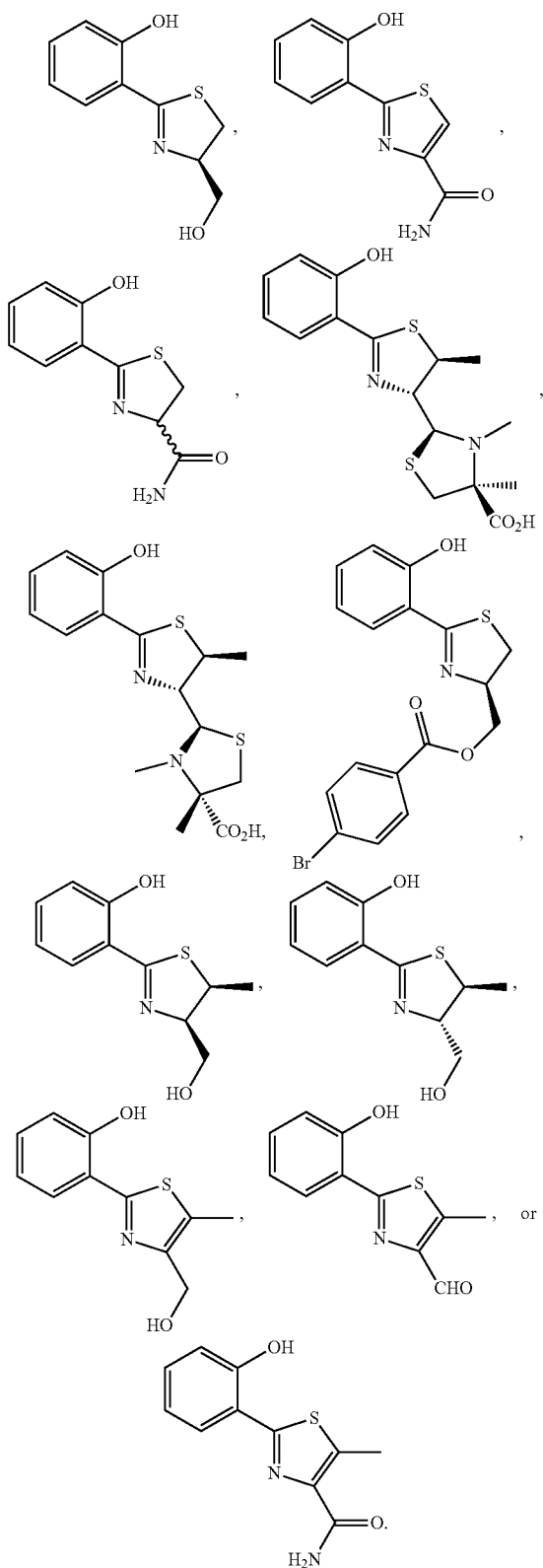

In a further aspect, the disorder is selected from motion sickness, emesis, post-operative nausea and vomiting (PONV), allergic disorders, allergic rhinitis, pruritus, psychiatric disorders, anxiety, neoplasia, cancer, periodontitis and osteoporosis, allergic conjunctivitis, ocular itching, allergic rhinitis, asthma, chronic urticaria, eczema dermatitis, prurigo, pruritis cutaneous, psoriasis vulgaris, erythema exsudativum multiforme, and an autoimmune disorder. In a further aspect, the autoimmune disorder is selected from rheumatoid arthritis, graft-versus host disease (GvHD), inflammatory bowel disease (IBD), insulin dependent diabetes mellitus (IDDM), multiple sclerosis, primary biliary cirrhosis, systemic sclerosis, psoriasis, autoimmune thyroiditis, and autoimmune thrombocytopenic purpura. In a yet further aspect, the autoimmune disorder is a Th1-mediated autoimmune disorder. In a still further, the Th1-mediated autoimmune disorder is multiple sclerosis.

In one aspect, the disorder is selected from anxiety, addiction, migraines, arthritis, allergy, viral infections, hypertension, diarrhea, psychosis, schizophrenia, depression, stress, anxiety, uropathy, addiction, ischemic trauma, L-dopa induced dyskinesia and obesity.

In one aspect, the disorder is selected from pulmonary hypertension, migraine, pain, hypertension, disorders of the gastrointestinal tract, restenosis, asthma, chronic heart disease, heart hypertrophy, obstructive airway disease, prostatic hyperplasia and priapism. In a further aspect, the pain disorder is selected from acute, chronic, neuropathic, inflammatory and cancer pain. In a still further aspect, the gastrointestinal tract disorder is selected from irritable bowel syndrome, hypertonic lower esophageal sphincter, and motility disorders. In a yet further aspect, prostatic hyperplasia disorder is selected from benign prostatic hyperplasia.

6. Use of Compounds

In one aspect, the invention relates to use of a compound for the treatment of a disorder related to calcium release in a mammal, the compound having a structure represented by a formula:

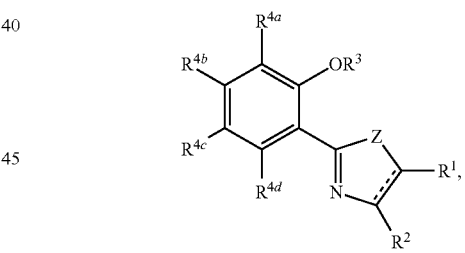

wherein ----- is an optional covalent bond, wherein valency is satisfied; wherein Z is selected from O and S; wherein $R^1$ is selected from hydrogen and optionally substituted C1-C6 alkyl; wherein $R^2$ is selected from nitrile, formyl, optionally substituted heteroaryl, optionally substituted heterocycloalkyl, optionally substituted alkoxyl, optionally substituted thioalkyl, optionally substituted alkylsulfonyl, optionally substituted alkylamino, thioamido, alkoxycarbonyl, carboxamide, amino-carbonyl, and alkylamine-carbonyl; wherein $R^3$ is selected from hydrogen and optionally substituted C1-C6 alkyl; wherein each of $R^{4a}$, $R^{4b}$, $R^{4c}$, and $R^{4d}$ is independently selected from hydrogen, halogen, hydroxyl, nitrile, nitro, thiol, formyl, optionally substituted amino, optionally substituted aryl, optionally substituted heteroaryl, optionally substituted alkoxyl, optionally substituted thioalkyl, optionally substituted alkylsulfinyl, optionally substituted alkylsulfonyl, optionally substituted alkylamino, thioamido, amidosulfonyl, alkoxycarbonyl, carboxamide, amino-carbonyl, alkylamine-carbonyl, and optionally substituted C1-C6 alkyl; or a pharmaceutically acceptable salt thereof.

In a further aspect, the compound has a structure represented by a formula:

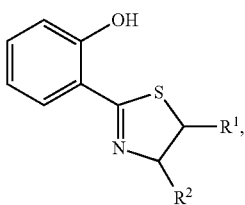

wherein R¹ is selected from hydrogen and optionally substituted C1-C6 alkyl; wherein R² is selected from nitrile, formyl, optionally substituted C1-C6 alkyl, optionally substituted heteroaryl, optionally substituted heterocycloalkyl, optionally substituted alkoxyl, optionally substituted thioalkyl, optionally substituted alkylsulfonyl, optionally substituted alkylamino, thioamido, alkoxycarbonyl, carboxamide, amino-carbonyl, and alkylamine-carbonyl; or a pharmaceutically acceptable salt thereof.

In a further aspect, the compound has a structure represented by a formula:

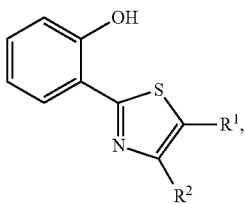

wherein R¹ is selected from hydrogen and optionally substituted C1-C6 alkyl; wherein R² is selected from nitrile, formyl, optionally substituted heteroaryl, optionally substituted heterocycloalkyl, optionally substituted alkoxyl, optionally substituted thioalkyl, optionally substituted alkylsulfonyl, optionally substituted alkylamino, thioamido, alkoxycarbonyl, carboxamide, amino-carbonyl, and alkylamine-carbonyl; or a pharmaceutically acceptable salt thereof.

In one aspect, the compound is selected from:

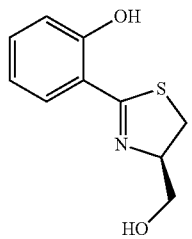, 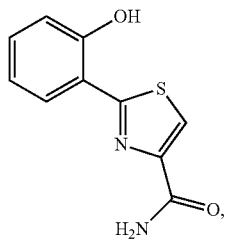,

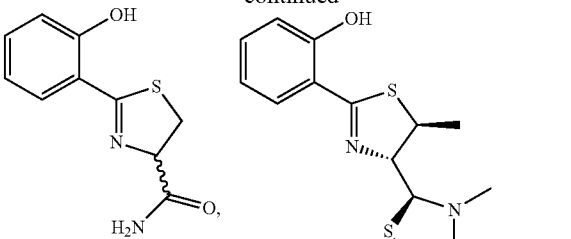

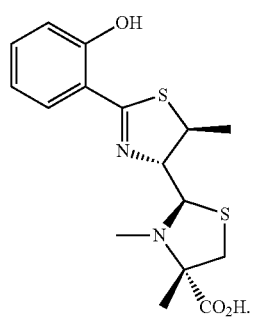

In a further aspect, the compound is selected from:

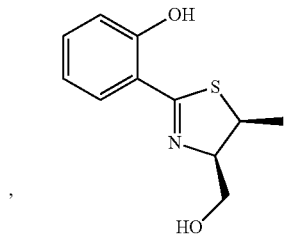

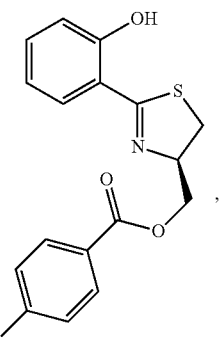

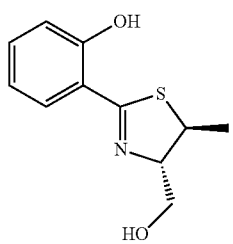, 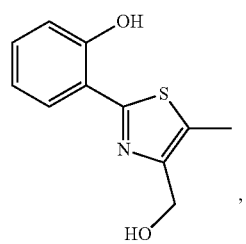,

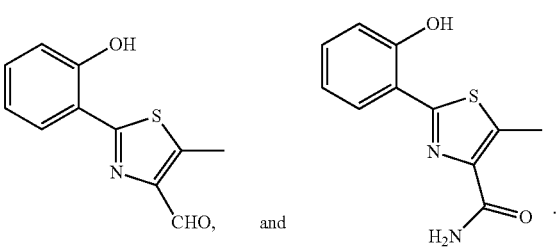

In a still further aspect, the compound is not:

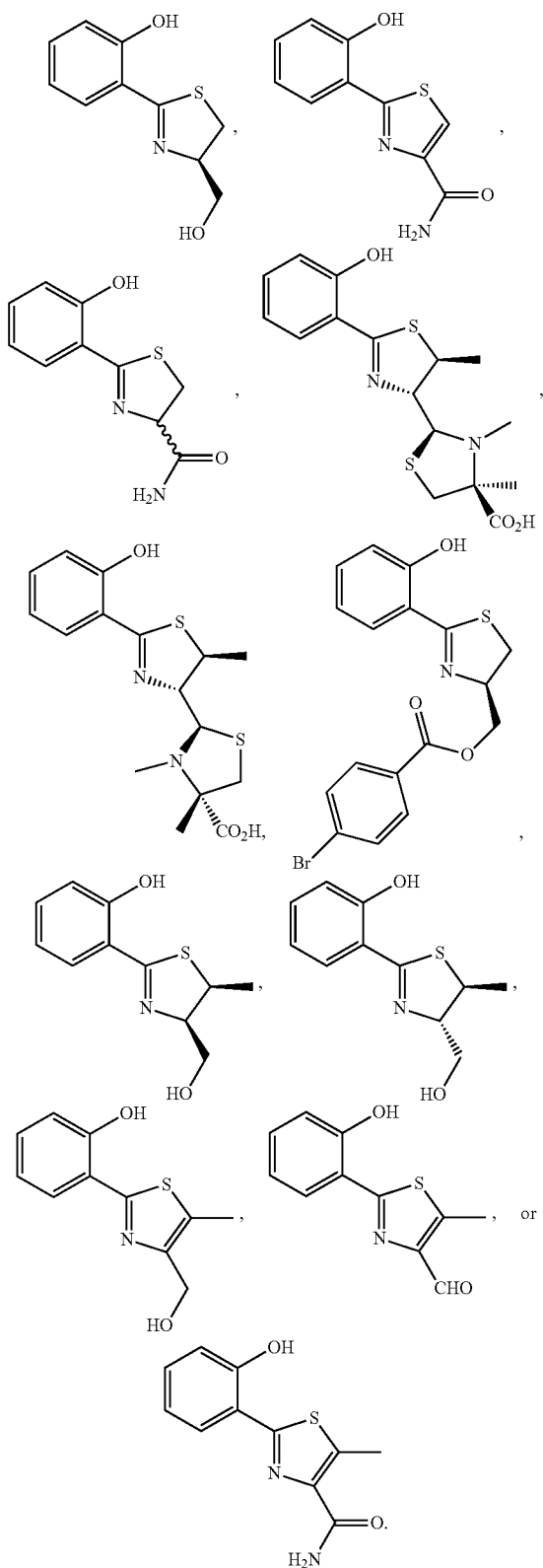

In a further aspect, the disorder is selected from motion sickness, emesis, post-operative nausea and vomiting (PONV), allergic disorders, allergic rhinitis, pruritus, psychiatric disorders, anxiety, neoplasia, cancer, periodontitis and osteoporosis, allergic conjunctivitis, ocular itching, allergic rhinitis, asthma, chronic urticaria, eczema dermatitis, prurigo, pruritus cutaneous, psoriasis vulgaris, erythema exsudativum multiforme, and an autoimmune disorder. In a further aspect, the autoimmune disorder is selected from rheumatoid arthritis, graft-versus host disease (GvHD), inflammatory bowel disease (IBD), insulin dependent diabetes mellitus (IDDM), multiple sclerosis, primary biliary cirrhosis, systemic sclerosis, psoriasis, autoimmune thyroiditis, and autoimmune thrombocytopenic purpura. In a yet further aspect, the autoimmune disorder is a Th1-mediated autoimmune disorder. In a still further, the Th1-mediated autoimmune disorder is multiple sclerosis.

In one aspect, the disorder is selected from anxiety, addiction, migraines, arthritis, allergy, viral infections, hypertension, diarrhea, psychosis, schizophrenia, depression, stress, anxiety, uropathy, addiction, ischemic trauma, L-dopa induced dyskinesia and obesity.

In one aspect, the disorder is selected from pulmonary hypertension, migraine, pain, hypertension, disorders of the gastrointestinal tract, restenosis, asthma, chronic heart disease, heart hypertrophy, obstructive airway disease, prostatic hyperplasia and priapism. In a further aspect, the pain disorder is selected from acute, chronic, neuropathic, inflammatory and cancer pain. In a still further aspect, the gastrointestinal tract disorder is selected from irritable bowel syndrome, hypertonic lower esophageal sphincter, and motility disorders. In a yet further aspect, prostatic hyperplasia disorder is selected from benign prostatic hyperplasia.

7. Non-Medical Uses

Also provided are the uses of the disclosed compounds and products as pharmacological tools in the development and standardization of in vitro and in vivo test systems for the evaluation of the effects of potentiators of calcium release in laboratory animals such as cats, dogs, rabbits, monkeys, rats and mice, as part of the search for new therapeutic agents for modulation of calcium release. In a further aspect, the invention relates to the use of a disclosed compound or a disclosed product as pharmacological tools in the development and standardization of in vitro and in vivo test systems for the evaluation of the effects of modulators of calcium release activity in laboratory animals such as cats, dogs, rabbits, monkeys, rats and mice, as part of the search for new therapeutic agents that modulate calcium release.

G. REFERENCES

Schmidt, E. W. Nat. Chem. Biol. 2008, 4, 466-473.
Piel, J. Nat. Prod. Rep. 2009, 26, 338-362.
Piel, J. Nat. Prod. Rep. 2004, 21, 519-538.
White, J. F.; Torres, M. S. CRC Press: New York, 2009.
Gil-Turnes, M. S.; Hay, M. E.; Fenical, W. Science 1989, 246, 116-118.
Terlau, H.; Olivera, B. M. Physiol. Rev. 2004, 84, 41-68.
Peraud, O.; Biggs, J. S.; Hughen, R. W.; Light, A. R.; Concepcion, G. P.; Olivera, B. M.; Schmidt, E. W. Appl. Environ. Microbiol. 2009, 75, 6820-6826.
Light, A. R.; Hughen, R. W.; Zhang, J.; Rainier, J.; Liu, Z.; Lee, J. J. Neurophysiol 2008, 100, 1184-1201.
Martin, D. J.; McClelland, D.; Herd, M. B.; Sutton, K. G.; Hall, M. D.; Lee, K.; Pinnock, R. D.; Scott, R. H. Neuropharmacology 2002, 42, 353-366.
Zamri, A.; Abdallah, M. A. Tetrahedron 1999, 56, 249-256.

Zunnundzhanov, A.; Bessonova, I. A.; Abdullaev, N. D.; Ogai, D. K. Khim. Prir. Soedin. 1987, 553-558.

You, M.-X.; Zhang, H.-P.; Hu, C.-Q. Chinese J Chem 2008, 26, 1332-1334.

Sasaki, O.; Igarashi, Y.; Saito, N.; Furumai, T. J. Antibiot. (Tokyo) 2002, 55, 249-255.

Mathur, K. B.; Iyer, R. N.; Dhar, M. L. J. Sci. Ind. Res., Sect. B 1962, 21B, 34-37.

Istanbullu, I.; Safak, C.; Sahin, M. F. Hacettepe Univ. Eczacilik Fak. Derg. 1986, 6, 21-28.

Yasuhara, F.; Yamaguchi, S. Tetrahedron Lett. 1977, 47, 4085-4088.

Sugimoto, Y.; Tsuyuki, T.; Moriyama, Y.; Takahashi, T. Bull. Chem. Soc. Jpn. 1980, 53, 3723-3724.

Len, C.; Pilard, S.; Lipka, E.; Vaccher, C.; Dubois, M.-P.; Shrinska, Y.; Tran, V.; Rabiller, C. Tetrahedron 2005, 61, 10583-10595.

Kikuchi, K.; Chen, C.; Adachi, K.; Nishijima, M.; Araki, M.; Sano, H. Tennen Yuki Kagobutsu Toronkai Koen Yoshishu 1996, 38th, 427-432.

Brea, J.; Castro-Palomino, J.; Yeste, S.; Cubero, E.; Parraga, A.; Dominguez, E.; Loza, M. I. Curr. Top. Med. Chem. 2010, 5, 493-503.

Aira, Z.; Buesa, I.; Salgueiro, M.; Bilbao, J.; Aguilera, L.; Zimmermann, M.; Azkue, J. J. Neuroscience 2010, 168, 831-841.

Yamada, Y.; Seki, N.; Kitahara, T.; Takahashi, M.; Matsui, M. Agr. Biol. Chem. 1970, 34, 780-783.

Kikuchi, K.; Chen, Y.; Adachi, K.; Nishijima, M.; Nishida, A.; Takatera, T.; Sano, H. Jpn. Kokai Tokkyo Koho, 1998, 6 pp. CODEN: JKXXAF JP 10245377 A 19980914 Heisei. CAN 129:244217 AN 1998:600005 CAPLUS.

Naegeli, H. U.; Zaehner, H. Helv. Chim. Acta 1980, 63, 1400-1406.

Cox, C. D.; Rinehart, K. L., Jr.; Moore, M. L.; Cook, J. C., Jr. Proc. Natl. Acad. Sci. U.S.A. 1981, 78, 4256-4260.

Drechsel, H.; Stephan, H.; Lotz, R.; Haag, H.; Zaehner, H.; Hantke, K.; Jung, G. Liebigs Ann. 1995, 10, 1727-1733.

Griffiths, G. L.; Sigel, S. P.; Payne, S. M.; Neilands, J. B. J. Biol. Chem. 1984, 259, 383-385.

Ino, A.; Kobayashi, S.; Hidaka, S.; Kawamura, Y.; Ozaki, M.; Hayase, Y.; Takeda, R.; Murabayashi, A. Tennen Yuki Kagobutsu Toronkai Koen Yoshishu 1996, 38th, 121-126.

Kobayashi, S.; Hidaka, S.; Kawamura, Y.; Ozaki, M.; Kayase, Y. J. Antibiot. 1998, 51, 323-327.

Shindo, K.; Takenaka, A.; Noguchi, T.; Hayakawa, Y.; Seto, H. J. Antibiot. 1989, 42, 1526-1529.

Bukovits, G. J.; Mohr, N.; Budzikiewicz, H.; Korth, H.; Pulverer, G. Z. Naturforsch., B: Anorg. Chem., Org. Chem. 1982, 37B, 877-880.

Waterfield, N. R.; Sanchez-Contreras, M.; Eleftherianos, I.; Dowling, A.; Wilkinson, P.; Parkhill, J.; Thomson, N.; Reynolds, S. E.; Bode, H. B.; Dorus, S.; ffrench-Constant, R. H. Proc. Natl. Acad. Sci. U.S.A. 2008, 105, 15967-15972.

Udwary, D. W.; Zeigler, L.; Asolkar, R. N.; Singan, V.; Lapidus, A.; Fenical, W.; Jensen, P. R.; Moore, B. S. Proc. Natl. Acad. Sci. U.S.A. 2007, 104, 10376-10381.

Crosa, J. H.; Walsh, C. T. Microbiol. Mol. Biol. Rev. 2002, 66, 223-249.

Li, C.; Kelly, W. L. Nat. Prod. Rep. 2010, 27, 153-164.

Taguchi, F.; Suzuki, T.; Inagaki, Y.; Toyoda, K.; Shiraishi, T.; Ichinose, Y. J. Bacteriol. 2010, 192, 117-126.

H. EXPERIMENTAL

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Methods for preparing and determining the structures of the compounds of this invention are illustrated in the following Examples. Biological activity, and methods used to determine the biological activity, of the compounds of this invention are illustrated in the following Examples. Optical rotations were measured on a Jasco DIP-370 polarimeter. UV spectra were obtained using a Perkin-Elmer Lambda2 UV/vis spectrometer. Circular dichroism spectra were obtained on a Jasco J720A spectropolarograph. NMR data were collected using either a Varian INOVA 500 ($^1$H 500 MHz, $^{13}$C 125 MHz) NMR spectrometer with a 3 mm Nalorac MDBG probe or a Varian NOVA 600 ($^1$H 600 MHz, $^{13}$C 150 MHz) NMR spectrometer equipped with a 5 mm $^1$H[$^{13}$C,$^{15}$N] triple resonance cold probe with a z-axis gradient, utilizing residual solvent signals for referencing. High-resolution mass spectra (HRMS) were obtained using a Bruker (Billerica, Mass.) APEXII FTICR mass spectrometer equipped with an actively shielded 9.4 T superconducting magnet (Magnex Scientific Ltd., UK), an external Bruker APOLLO ESI source, and a Synrad 50W CO2 CW laser.

1. Bacterial Material

Streptomyces sp. CP32 was cultivated from C. pulicarius obtained by professional collectors near Mactan Island, Cebu, Philippines as previously described. The strain was cultured from dissected foot and body tissue, purified, and later the strain was recovered from a glycerol stock and used for further chemical analysis.

2. Fermentation and Extraction

Streptomyces sp. CP32 was cultured at 30° C. with shaking at 200 rpm in 8 2.8 L Fernbach flasks each containing 1 L of the medium ISP2 (0.2% yeast extract, 1% malt extract, 0.2% glucose, 2% NaCl). After 8 days, the broth was centrifuged and the supernatant was extracted with HP-20 resin for 4 hours. The resin was filtered through cheesecloth and washed with water to remove salts. The filtered resin was eluted with MeOH to yield the crude extract. Crude extracts of pilot-scale cultures of strain CP32 were strongly active in the DRG assay, resulting in K$^+$-stimulated Ca$^{2+}$ influx.

3. Purification of Bacterial Extract

The crude extract (400 mg) was separated into 7 fractions (Fr1-Fr7) on a C$_{18}$ column using step-gradient elution of MeOH in H$_2$O (20%, 40%, 50%, 60%, 70%, 80%, 100%). Fr 3 eluting in 50% MeOH was further purified by C$_{18}$ HPLC using 45% CH$_3$CN in H$_2$O to obtain compound 8 (1.5 mg). Fr 4 eluting in 60% MeOH was further purified by C$_{18}$ HPLC using 65% MeOH in H$_2$O to obtain compounds 1 (3.0 mg), 2 (1.0 mg), and 3 (0.4 mg). Fr 5 eluting in 70% MeOH was further purified by C$_{18}$ HPLC using 68% CH$_3$CN in H$_2$O with 0.1% TFA to obtain compound 5 (5.0 mg) and subfraction Fr 5-1. Fr 5-1 was further purified by $C_{18}$ HPLC using 48% $CH_3CN$ in $H_2O$ with 0.1% TFA to obtain compounds 4 (1.0 mg), 6 (0.3 mg), 7 (1.5 mg), 9 (10.0 mg) and 10 (2.0 mg). Compound numbers correspond to the compounds listed in the next section ("Isolated Compounds").

4. Isolated Compounds

Using the methods described herein, exemplary compounds listed below were isolated and characterized.

| Compound Number | Name | Structure |
|---|---|---|
| 1 | (R)-2-(4-(hydroxymethyl)-4,5-dihydrothiazol-2-yl)phenol | 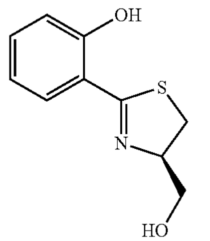 [SMILES: OC[C@@H]1CSC(c2ccccc2O)=N1] |
| 2 | 2-((4R,5S)-4-(hydroxymethyl)-5-methyl-4,5-dihydrothiazol-2-yl)phenol | 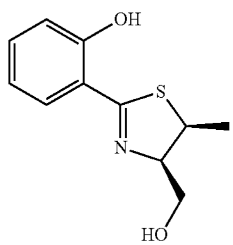 |
| 3 | 2-((4S,5S)-4-(hydroxymethyl)-5-methyl-4,5-dihydrothiazol-2-yl)phenol | 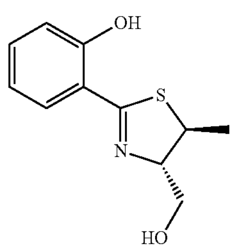 |
| 4 | 2-(4-(hydroxymethyl)-5-methylthiazol-2-yl)phenol | 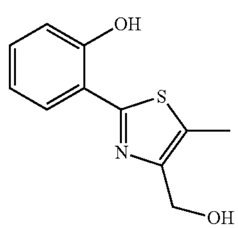 |
| 5 | 2-(2-hydroxyphenyl)-5-methylthiazole-4-carbaldehyde | 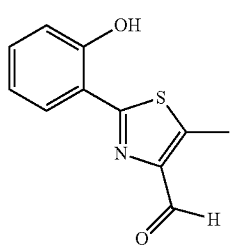 |
| 6 | 2-(2-hydroxyphenyl)-5-methylthiazole-4-carboxamide | |
| 7 | 2-(2-hydroxyphenyl)thiazole-4-carboxamide | |
| 8 | 2-(2-hydroxyphenyl)-4,5-dihydrothiazole-4-carboxamide | |
| 9 | (2S,4S)-2-((4R,5S)-2-(2-hydroxyphenyl)-5-methyl-4,5-dihydrothiazol-4-yl)-3,4-dimethylthiazolidine-4-carboxylic acid | |
| 10 | (2R,4S)-2-((4R,5S)-2-(2-hydroxyphenyl)-5-methyl-4,5-dihydrothiazol-4-yl)-3,4-dimethylthiazolidine-4-carboxylic acid | |

5. Spectroscopic Characterization of Isolated Compounds a. (R)-2-(4-(hydroxymethyl)-4,5-dihydrothiazol-2-yl)phenol (1)

Figure 3:
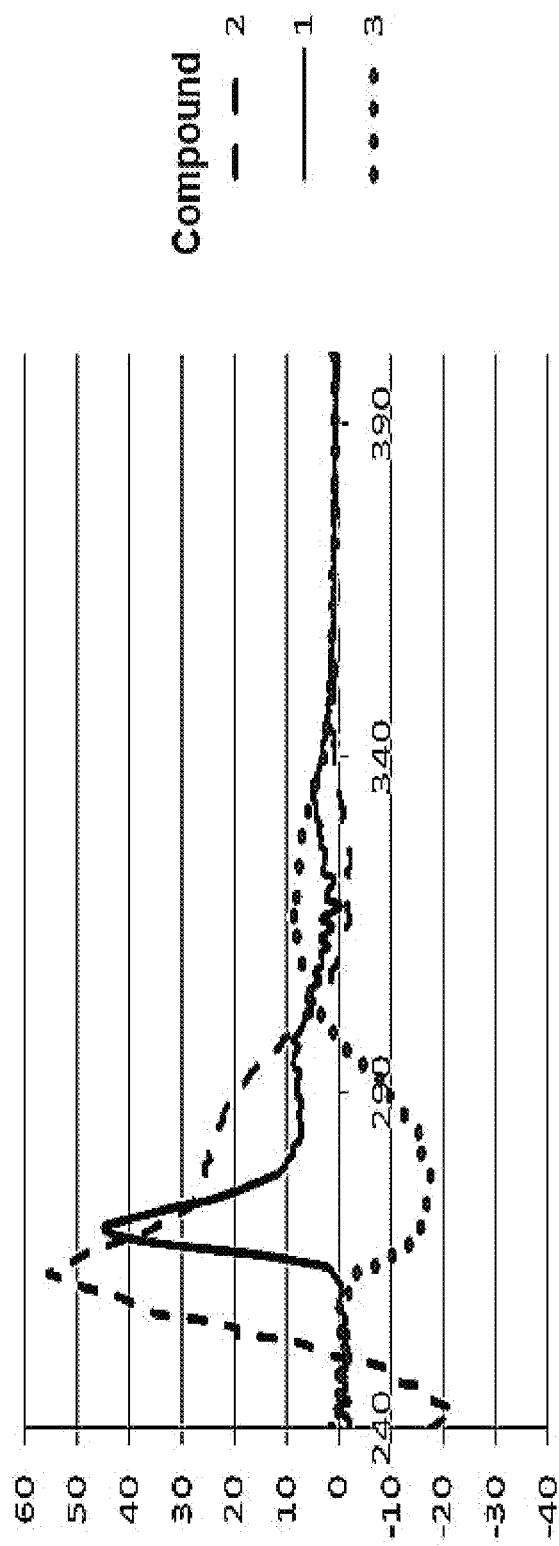
FIG. 3 shows representative circular dichroism spectra of three exemplary compounds.
Figure 27:
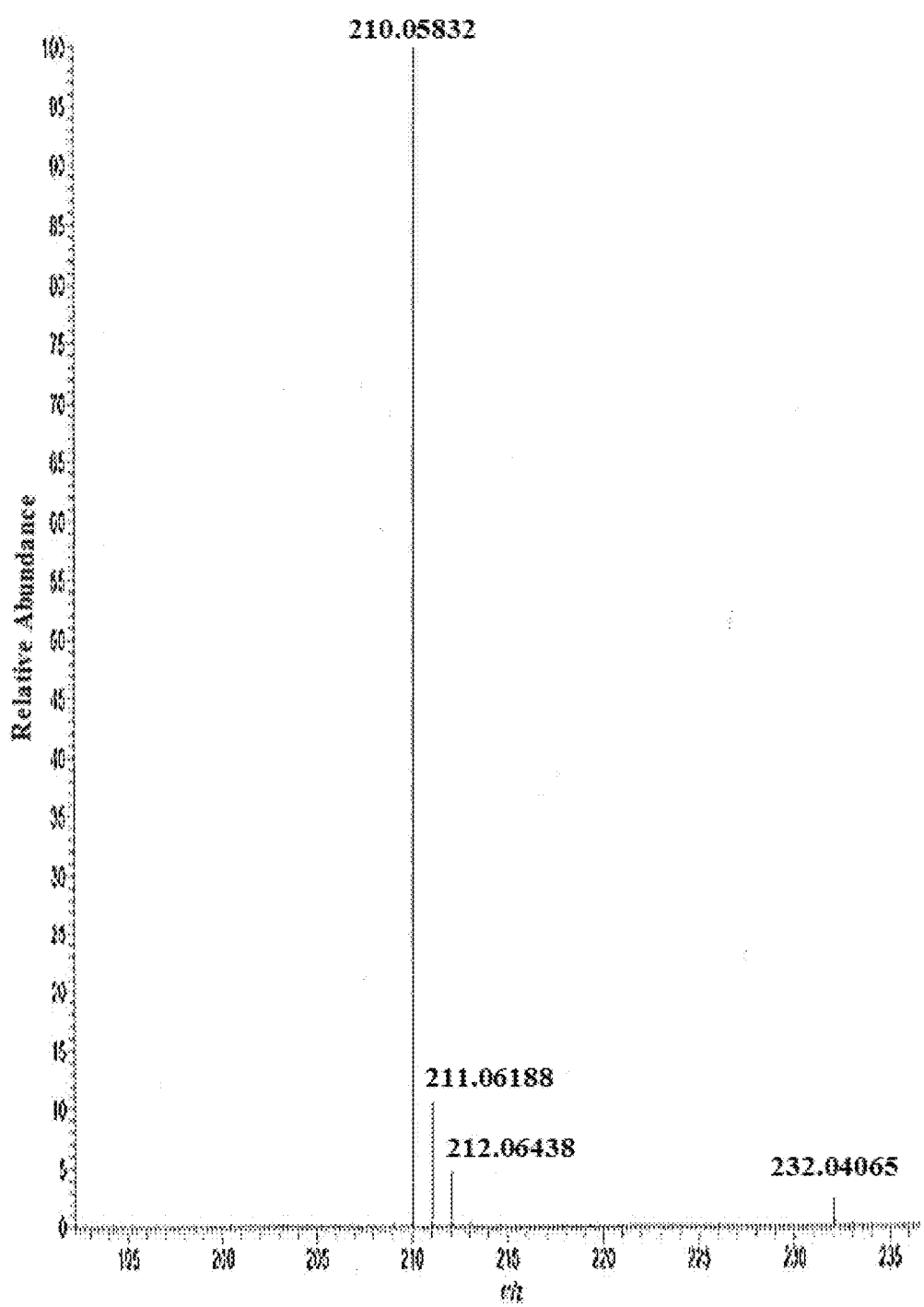
FIG. 27 shows a representative a spectrum obtained by high resolution electrospray ionization mass spectroscopy (HRESIMS) of an exemplary compound.

Compound 1 was isolated as a pale yellow solid. High-resolution electrospray mass spectrometry (HRESIMS)

revealed ions at m/z 210.0583 [M+H]+ (FIG. 27), indicating a molecular formula of $C_{10}H_{11}NO_2S$. A 4-bromobenzoyl derivative 1a was synthesized from 1, and a shift of C7' from 3.85 to 4.58 ppm indicated a primary alcohol group at C7'. HMBC correlations are shown in FIG. 2. A representative circular dichroism spectrum is shown in FIG. 3.

b. 2-((4R,5S)-4-(hydroxymethyl)-5-methyl-4,5-dihydrothiazol-2-yl)phenol (2)

Compound 2 is a pale yellow solid (MeOH); $[\alpha]^{25}_D$ −53.0 (c 0.1, CHCl$_3$); UV (MeOH) $\lambda_{max}$ (log ε) 211 (4.12), 250 (3.71), 312 (3.50) nm; IR (film) $\nu_{max}$: 2925, 1700, 1670, 1565, 1535, 1510, 1310, 1265, 760 cm$^{-1}$; $^1$H and $^{13}$C NMR (see below); HRESIMS m/z 224.0741 [M+H]+ (calcd for $C_{11}H_{14}NO_2S$, 224.0745). A representative circular dichroism spectrum is shown in FIG. 3.

Figure 6:
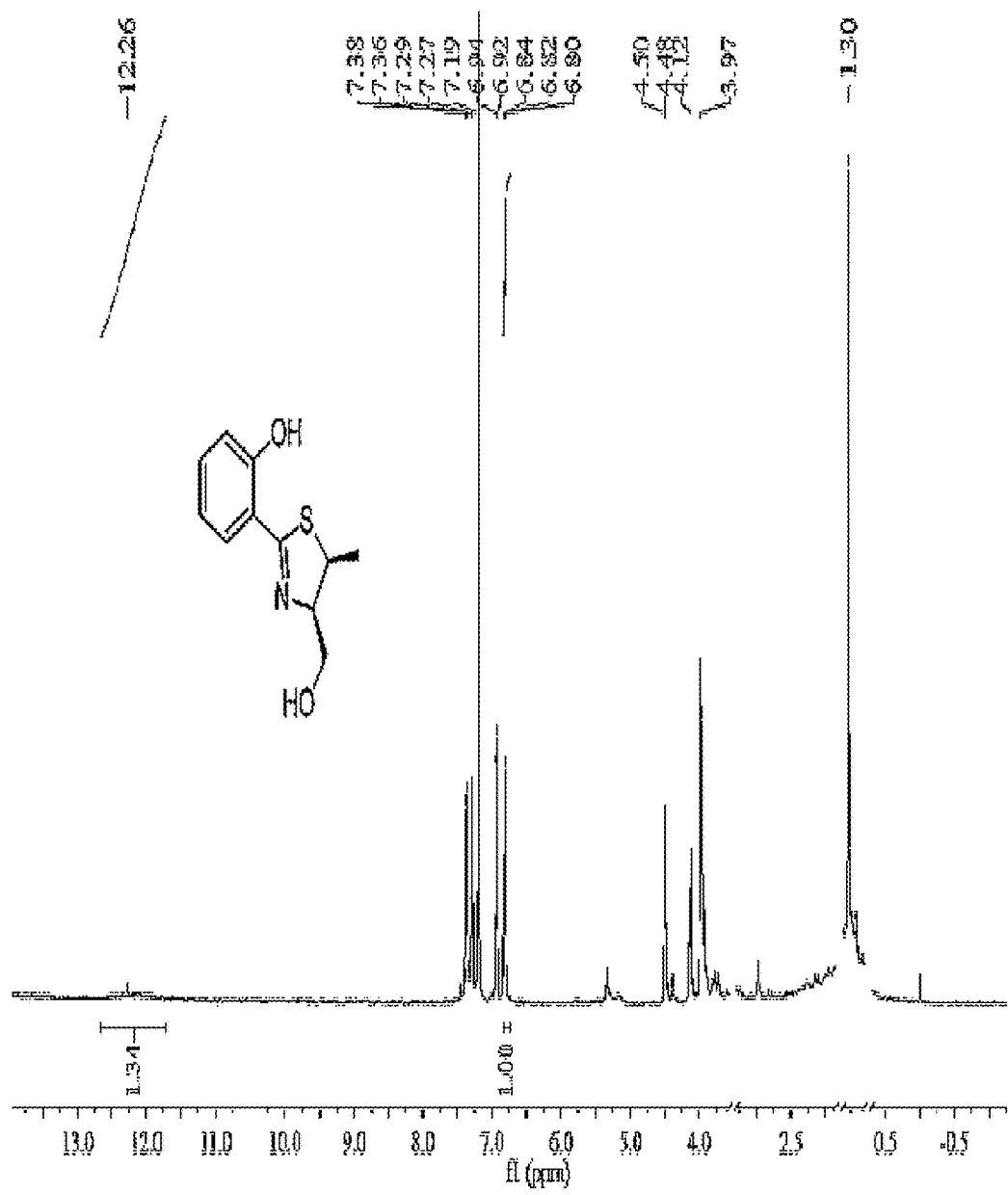
FIG. 6 shows a representative $^1$H NMR spectrum of an exemplary compound.
Figure 7:
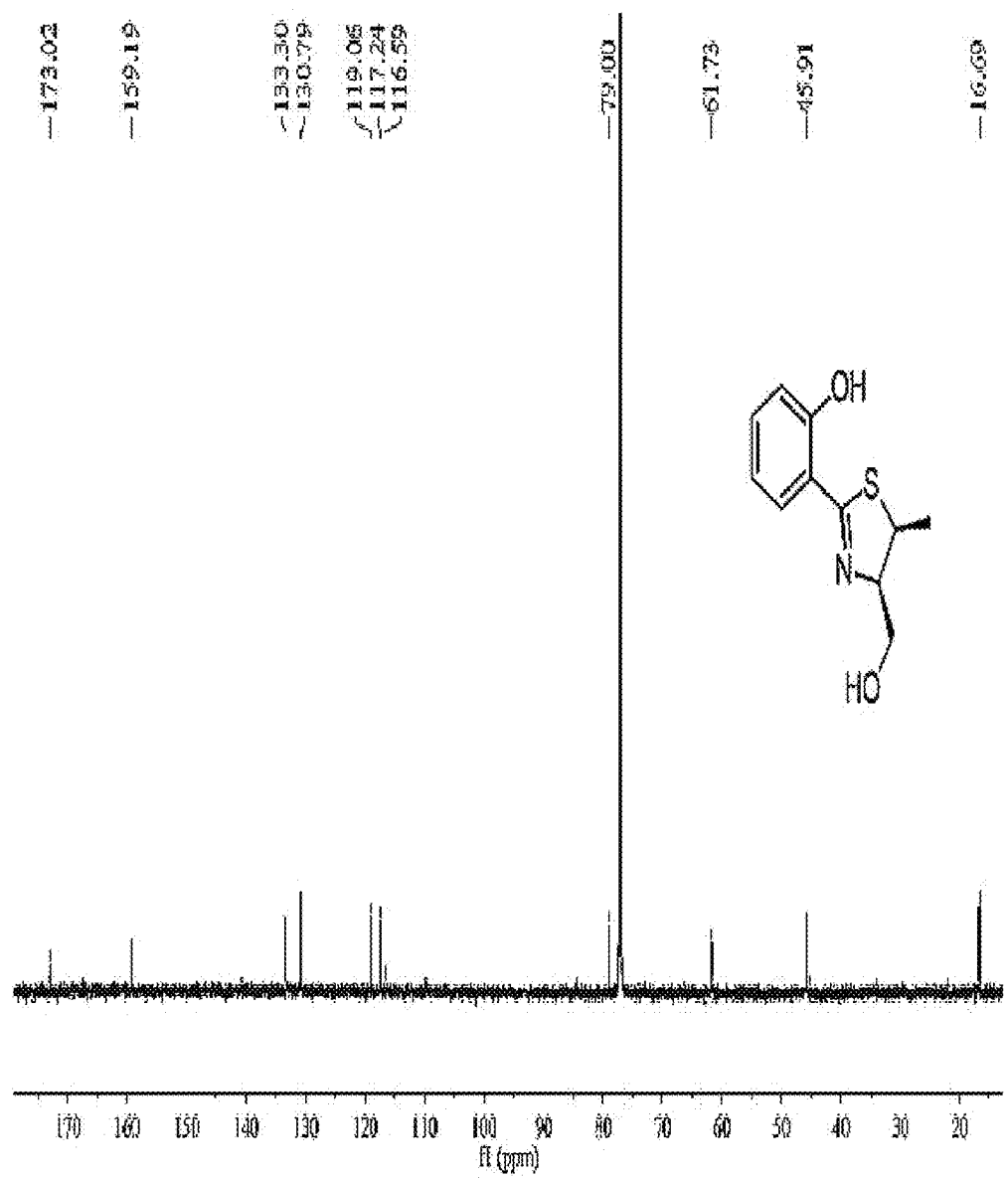
FIG. 7 shows a representative $^1$H NMR spectrum of an exemplary compound.
Figure 8:
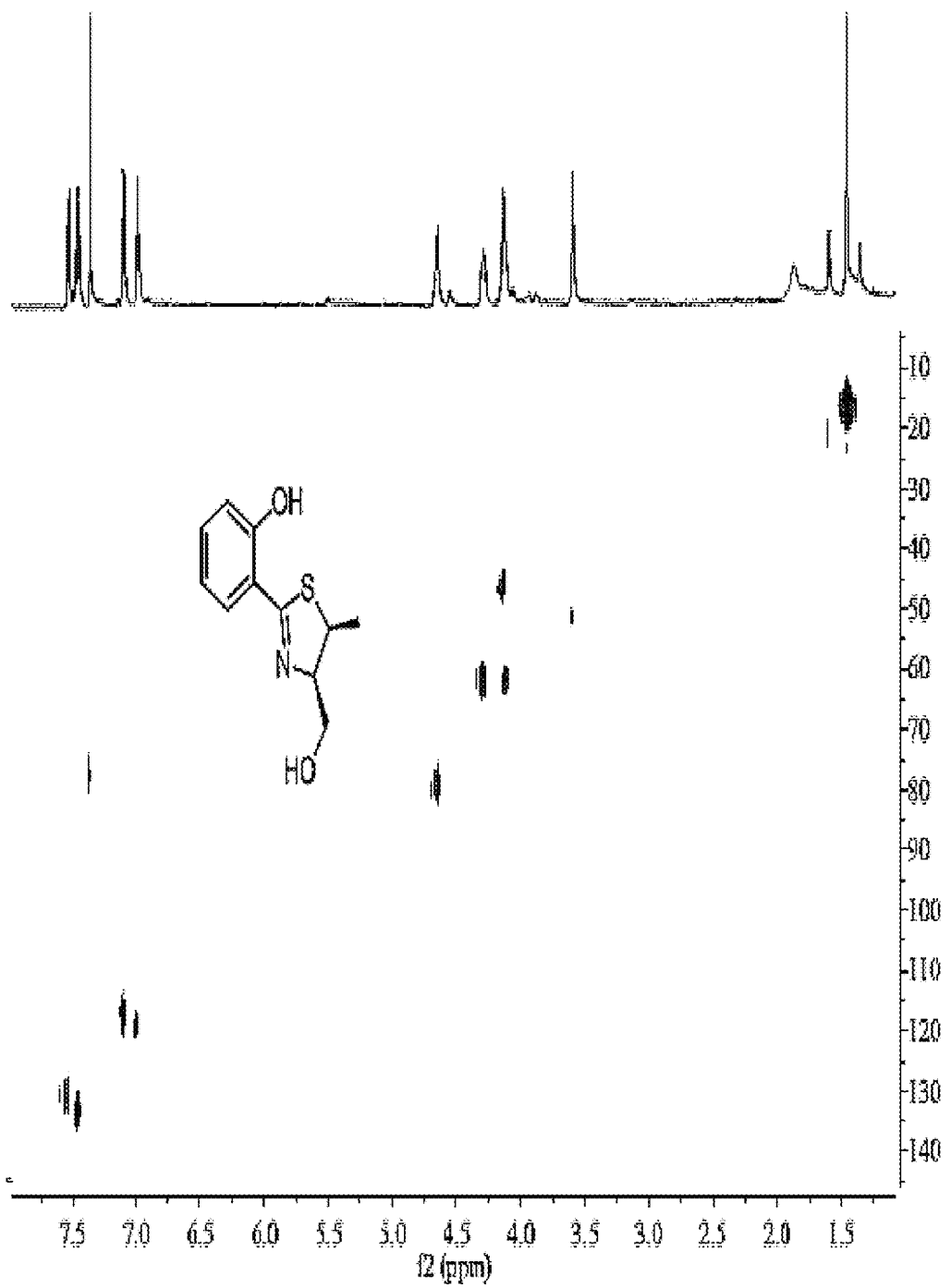
FIG. 8 shows a representative heteronuclear single quantum coherence (HSQC) spectrum of an exemplary compound.
Figure 9:
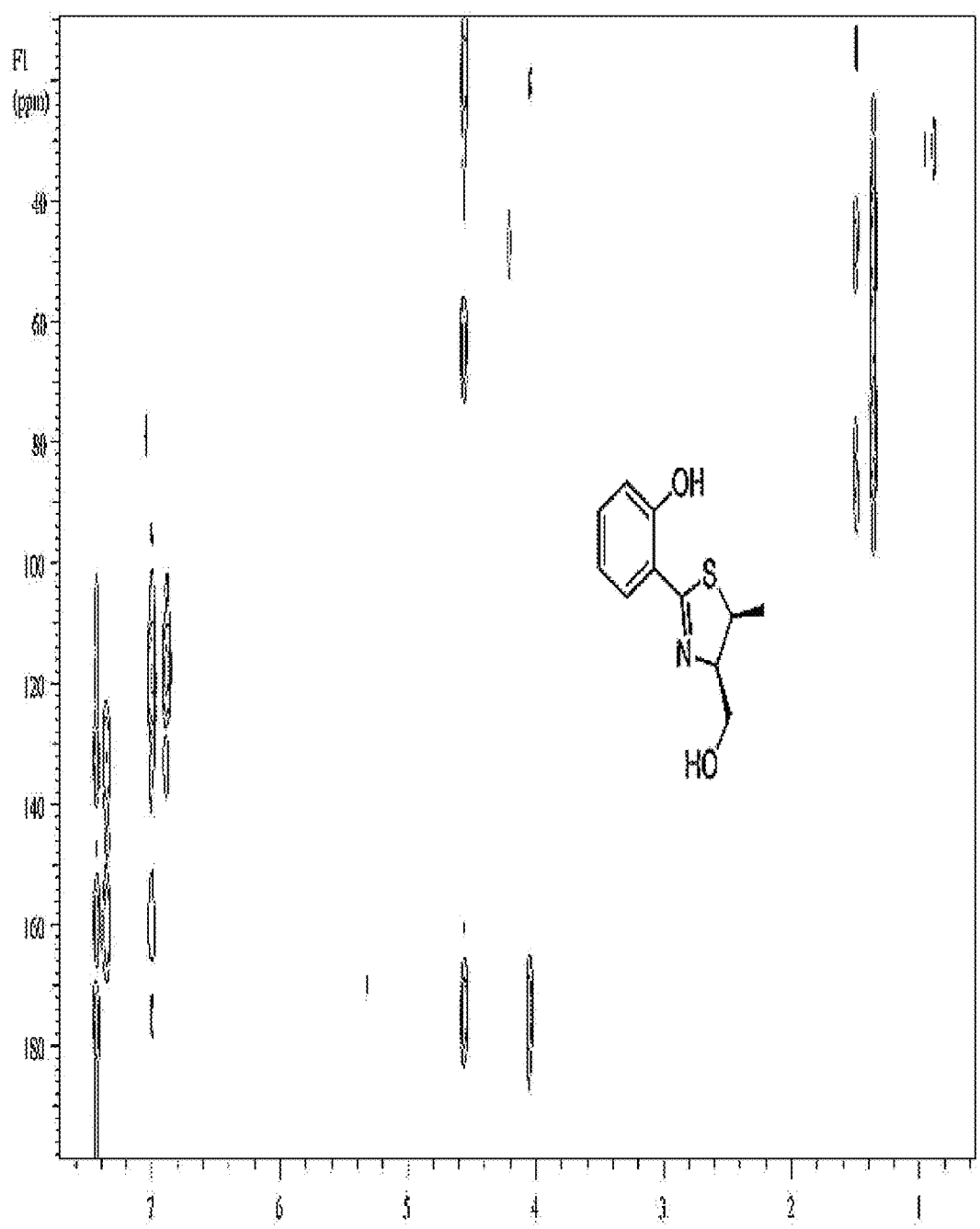
FIG. 9 shows a representative HMBC spectrum of an exemplary compound.
Figure 10:
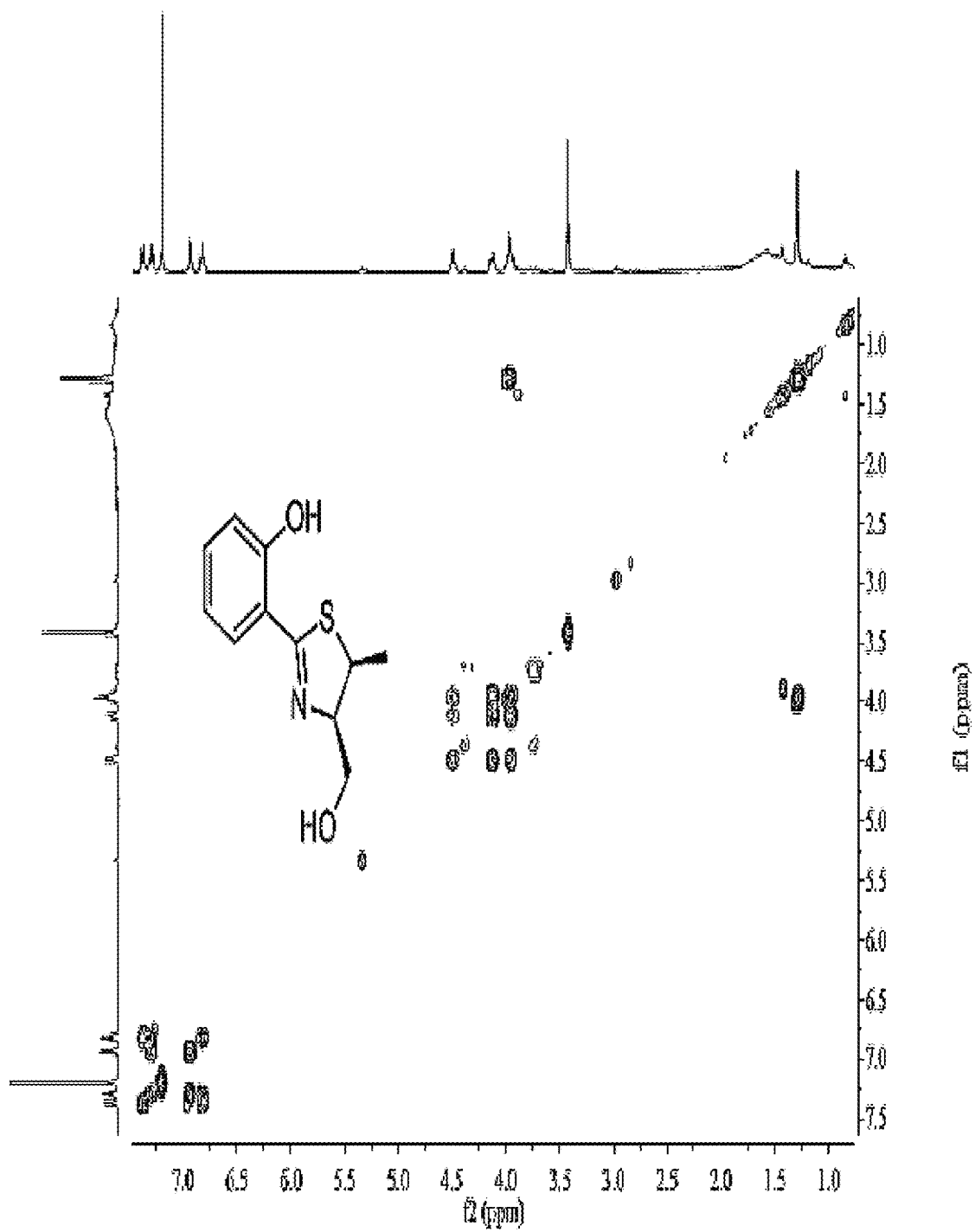
FIG. 10 shows a representative $^1$H-$^1$H COSY spectrum of an exemplary compound.
Figure 11:
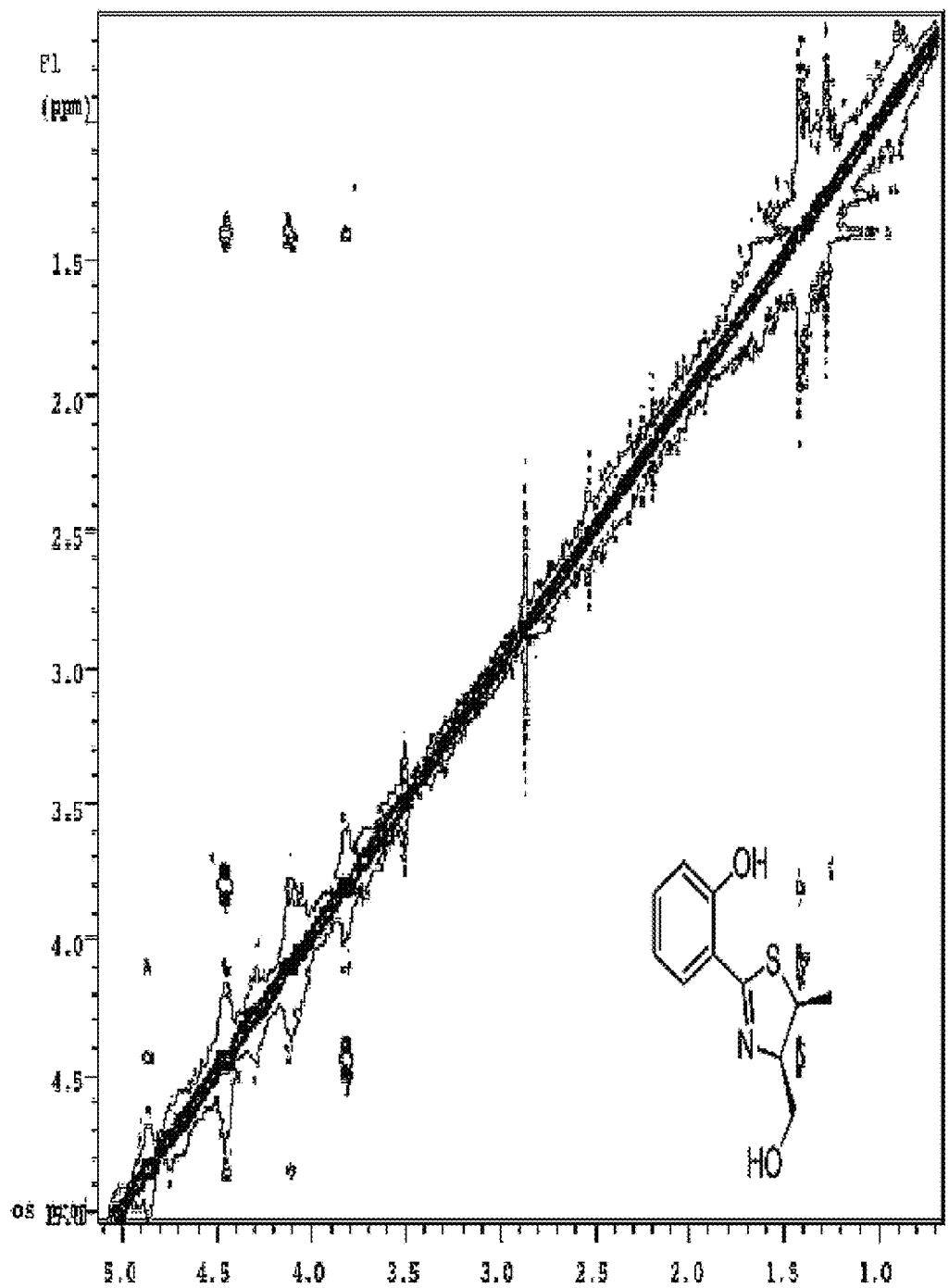
FIG. 11 shows a representative NOESY spectrum of an exemplary compound.
Figure 28:
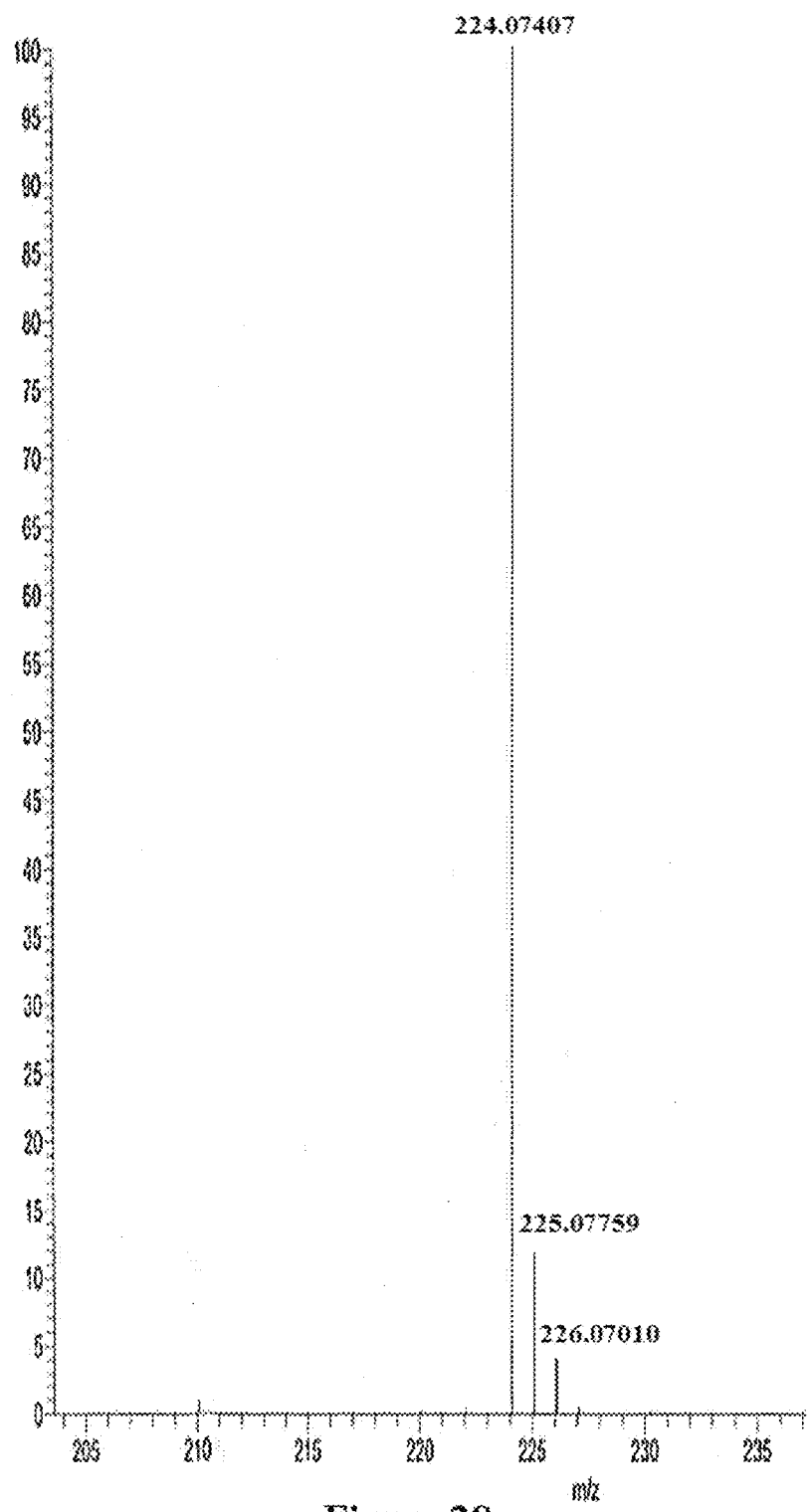
FIG. 28 shows a representative HRESIMS spectrum of an exemplary compound.

The molecular formula $C_{11}H_{13}NO_2S$ was assigned on the basis of HRESIMS analysis (m/z 224.0741 for [M+H]+) and NMR experiments (FIG. 28). Compound 2 was larger than compound 1 by 14 Da, indicating that an additional $CH_2$ was present. The $^1$H NMR and $^{13}$C NMR spectra of compound 2 were very similar to that of compound 1 except that they have signals corresponding to a methyl group at $\delta_H$ 1.35 (FIGS. 6 and 7). Compound 2 contained a methine group ($\delta_H$ 4.04 m; $\delta_C$ 45.9 CH) instead of the methylene group in compound 1. A COSY experiment (FIG. 10) led to the identification of the CH(CH$_3$)CHCH$_2$OH fragment. The HMBC cross-peaks observed from both H-4' and H-5' to C1' confirmed the planar structure of compound 2 (FIG. 9). The NOESY correlations between H-6' and H-7' indicated a 4'R*,5'R* relative configuration of compound 2 (FIG. 11). The HSQC spectrum is shown in FIG. 8. Key HMBC, $^1$H-$^1$H COSY, and NOESY correlations are shown in FIG. 2.

| position | $\delta_C$, mult | $\delta_H$ (J in Hz) |
|---|---|---|
| 1 | 116.6, qC | |
| 2 | 159.2, qC | |
| 2-OH | | 12.25, brs |
| 3 | 133.3, CH | 7.44, d (9.0) |
| 4 | 119.1, CH | 6.88, dd (9.0, 8.5) |
| 5 | 130.8, CH | 7.36, dd (8.5, 8.5) |
| 6 | 117.3, CH | 7.00, d (8.5) |
| 2' | 173.0, qC | |
| 4' | 45.9, CH$_2$ | 4.04, m |
| 5' | 79.0, CH | 4.56, ddd (6.8, 6.8, 6.7) |
| 6' | 16.7, CH$_3$ | 1.35, d (7.1) |
| 7' | 61.7, CH | 4.04 m, 4.19, dd (10.4, 6.1) | c. 2-((4S,5S)-4-(hydroxymethyl)-5-methyl-4,5-dihydrothiazol-2-yl)phenol (3)

Compound 3 is a pale yellow solid (MeOH); $[\alpha]^{25}_D$ −25.0 (c 0.1, CHCl$_3$); UV (MeOH) $\lambda_{max}$ (log ε) 211 (4.11), 250 (3.69), 312 (3.47) nm; IR (film) $\nu_{max}$: 2909, 1685, 1520, 1457, 1415, 1340, 1310, 1265, 770 cm$^{-1}$; $^1$H and $^{13}$C NMR (see below); HRESIMS m/z 224.0741 [M+H]+ (calcd for $C_{11}H_{14}NO_2S$, 224.0745).

Figure 12:
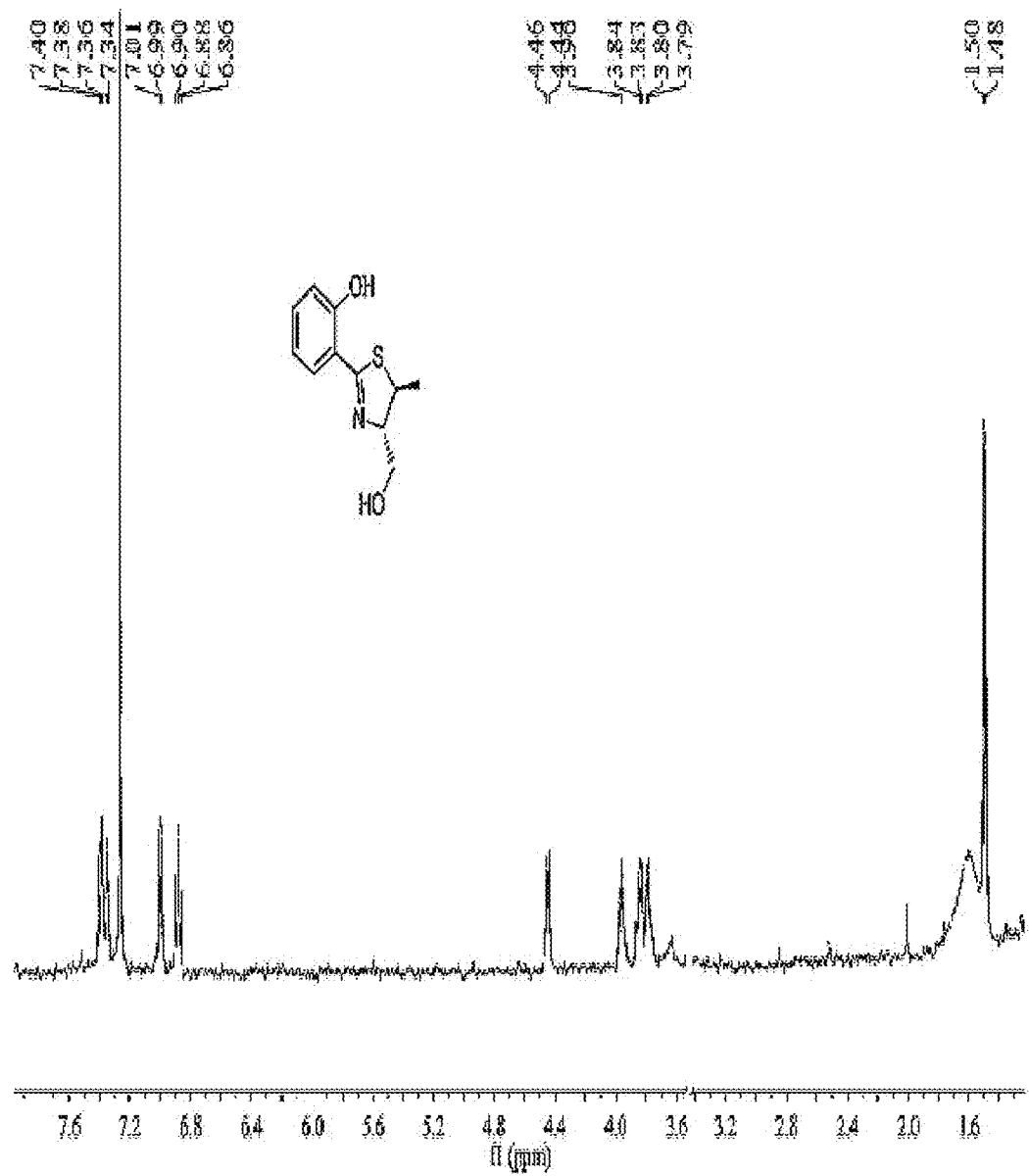
FIG. 12 shows a representative $^1$H NMR spectrum of an exemplary compound.
Figure 13:
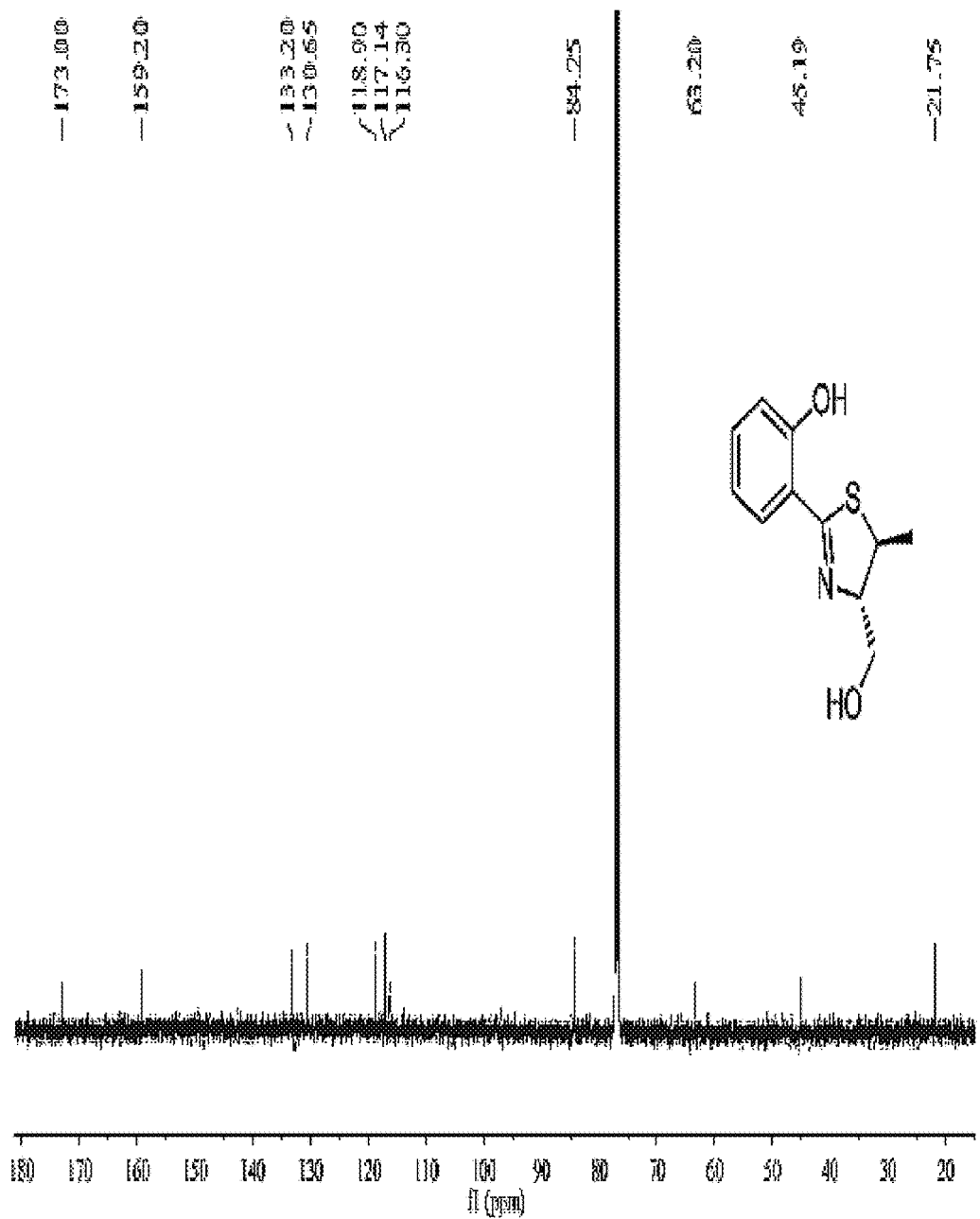
FIG. 13 shows a representative $^{13}$C NMR spectrum of an exemplary compound.
Figure 14:
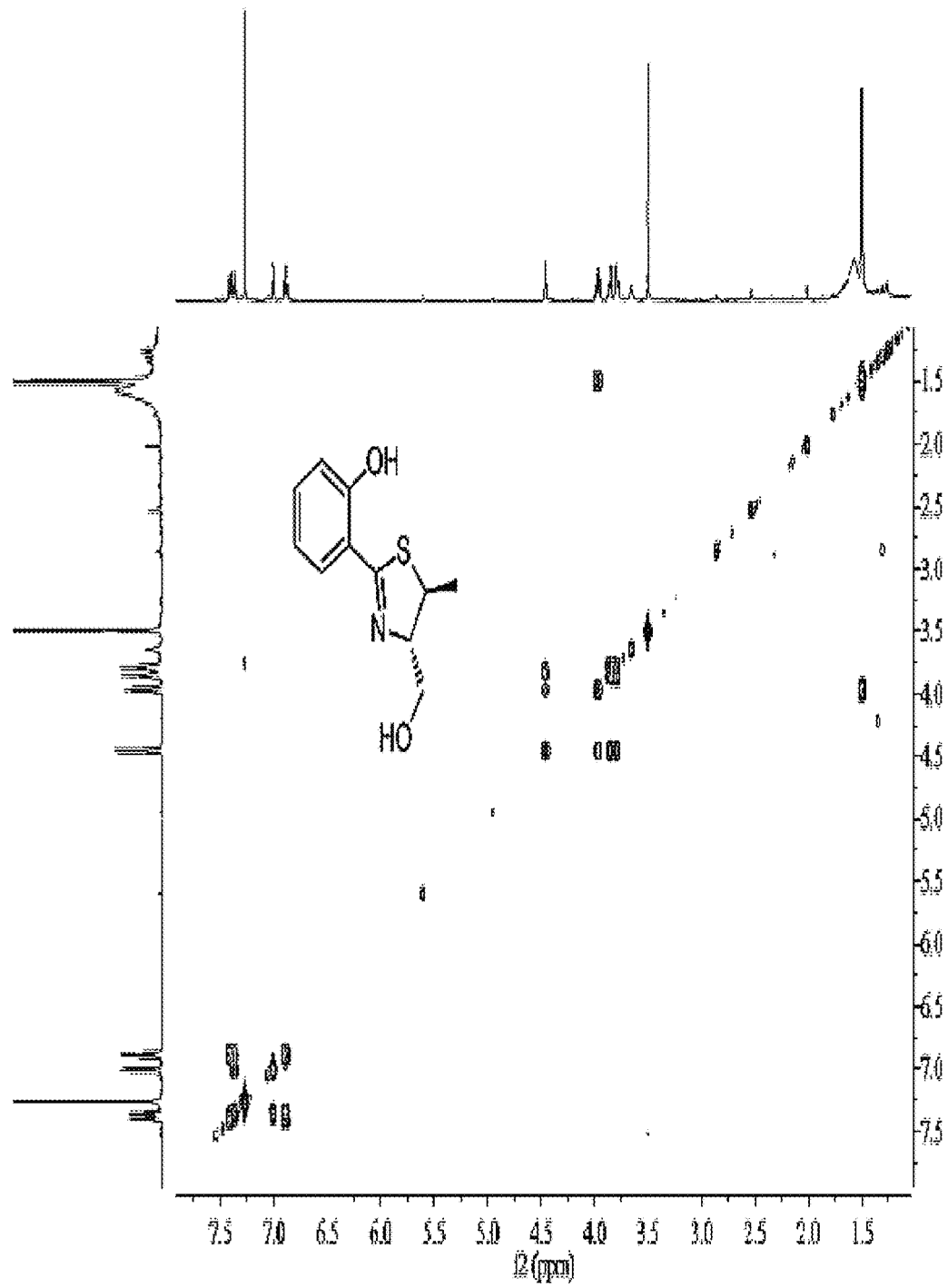
FIG. 14 shows a representative $^1$H-$^1$H COSY spectrum of an exemplary compound.
Figure 15:
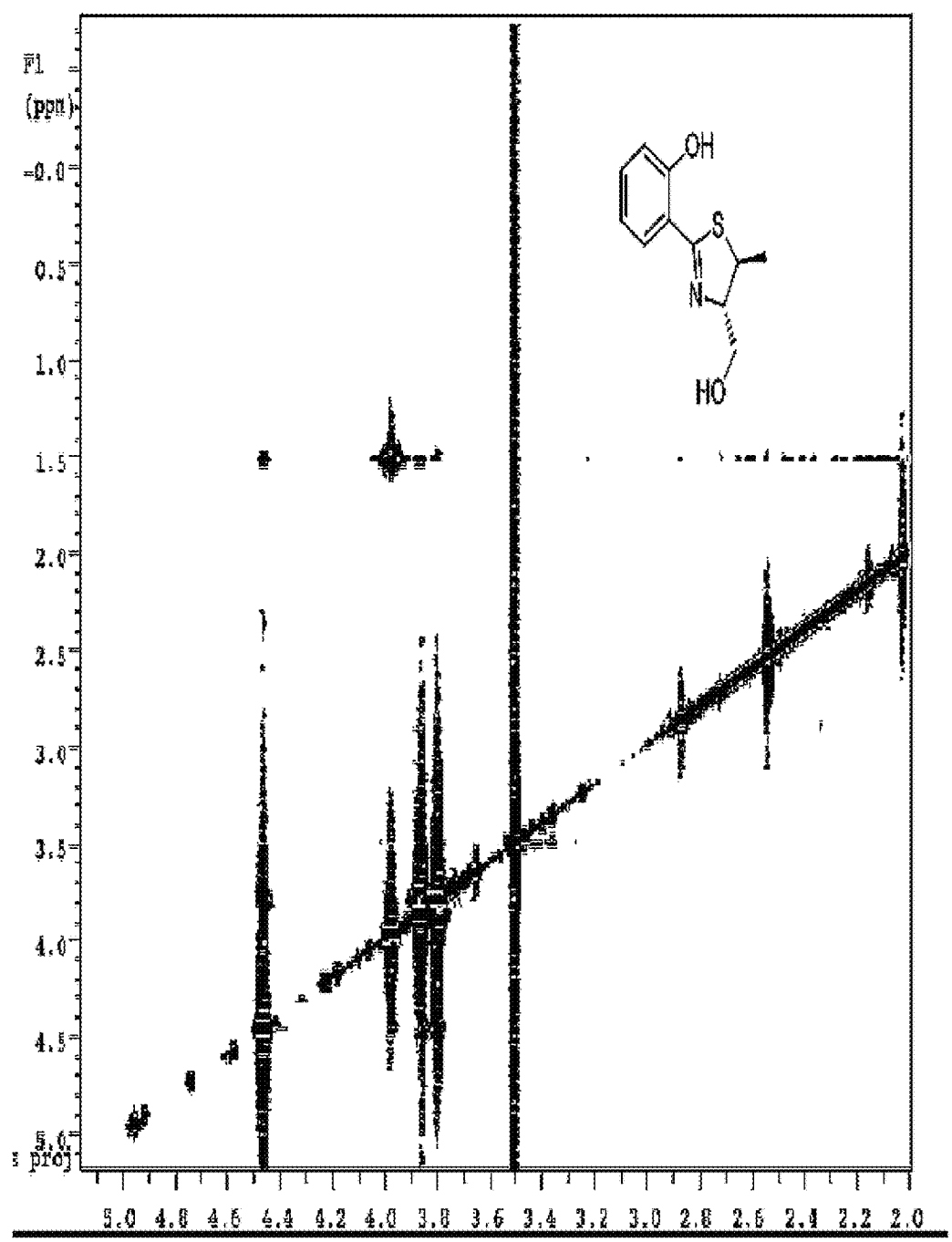
FIG. 15 shows a representative NOESY spectrum of an exemplary compound.
Figure 29:
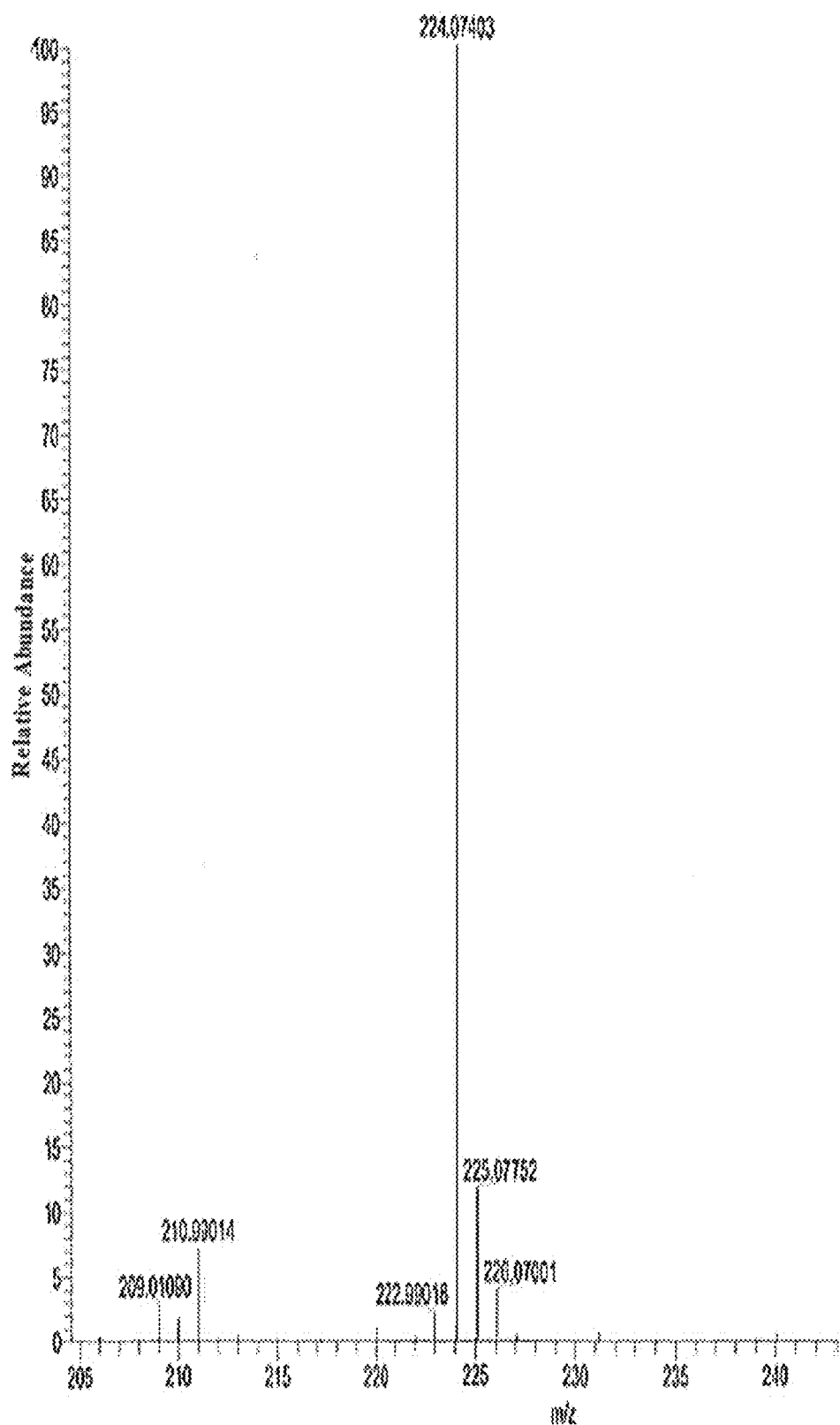
FIG. 29 shows a representative HRESIMS spectrum of an exemplary compound.

The MS (FIG. 29) and NMR data ($^1$H NMR, FIG. 12 and $^{13}$C NMR, FIG. 13) of compound 3 were almost identical to that of compound 2 except for that the chemical shifts of C5', C6' and C7' were observed slightly downfield of those in 2 suggesting that it was isomeric with compound 2. The NOESY correlations between H-6' and H-5' indicated 3 was a diastereoisomer of 2 with a 4'R*,5'S* relative configuration. (FIG. 15). A COSY experiment is shown in FIG. 14. Key $^1$H-$^1$H COSY and NOESY correlations are shown in FIG. 2.

| position | $\delta_C$, mult | $\delta_H$ (J in Hz) |
|---|---|---|
| 1 | 116.3, qC | |
| 2 | 159.2, qC | |
| 2-OH | | 12.4, brs |
| 3 | 133.1, CH | 7.39, d (8.3) |
| 4 | 118.9, CH | 6.88, dd (8.3, 8.2) |
| 5 | 130.6, CH | 7.36, dd (8.3, 8.2) |
| 6 | 117.1, CH | 6.99, d (8.3) |
| 2' | 173.0, qC | |
| 4' | 45.2, CH | 3.96, dq (6.8, 6.8) |
| 5' | 84.2, CH | 4.45, ddd (6.8, 5.5, 4.8) |
| 6' | 21.7, CH$_3$ | 1.49, d (6.8) |
| 7' | 63.2, CH$_2$ | 3.85, dd (11.2, 5.5); 3.78, dd (11.2, 4.8) | d. 2-(4-(hydroxymethyl)-5-methylthiazol-2-yl)phenol (4)

Compound 4 is a pale yellow solid (MeOH); UV (MeOH) $\lambda_{max}$ 204 (4.08), 296 (3.82), 326 (3.79) nm; IR (film) $\nu_{max}$: 2925, 1700, 1625, 1505, 1415, 1280, 1000, 775 cm$^{-1}$; $^1$H and $^{13}$C NMR (see below); HRESIMS m/z 222.0584 [M+H]+ (calcd for $C_{11}H_{12}NO_2S$, 222.0589).

Figure 16:
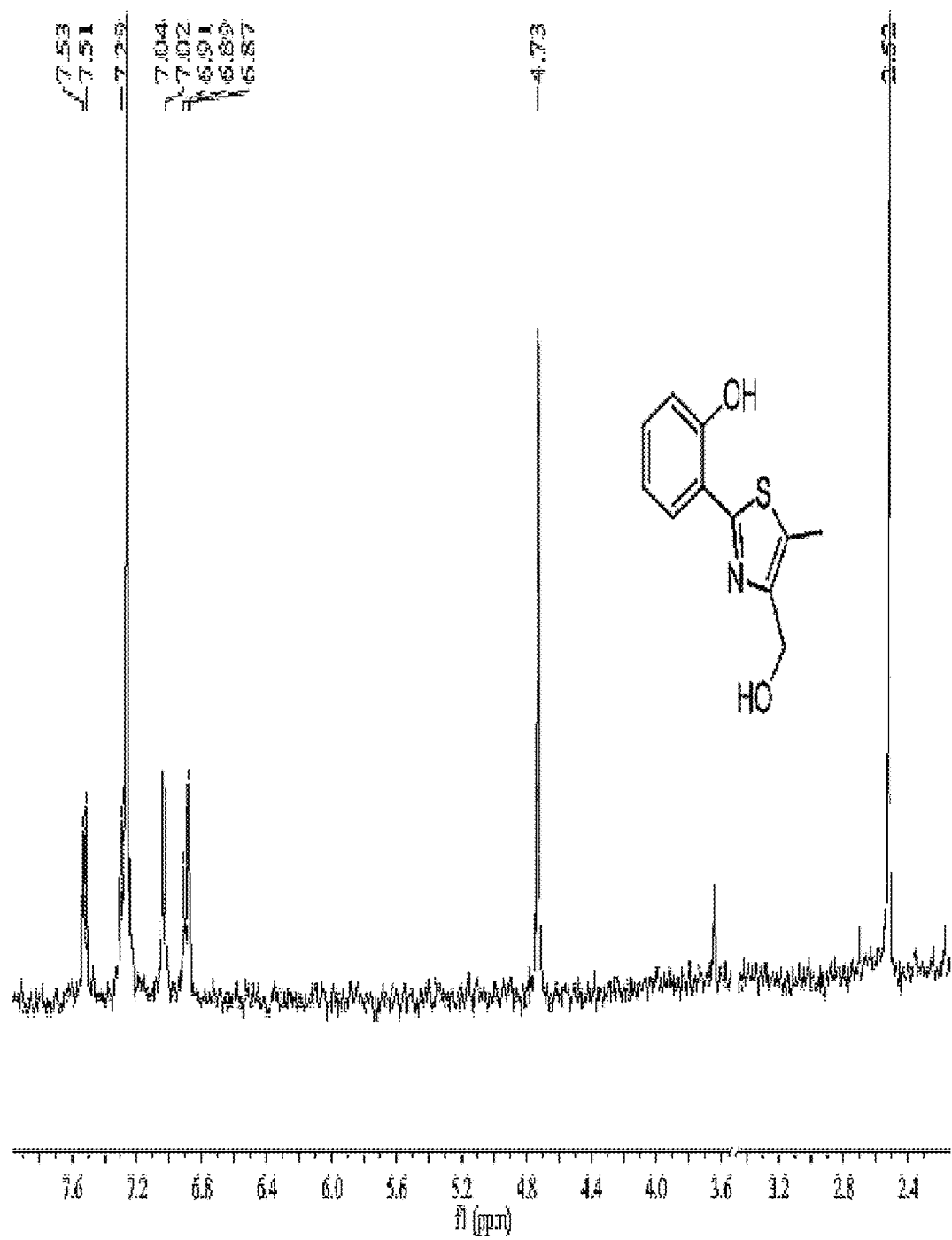
FIG. 16 shows a representative $^1$H NMR spectrum of an exemplary compound.
Figure 17:
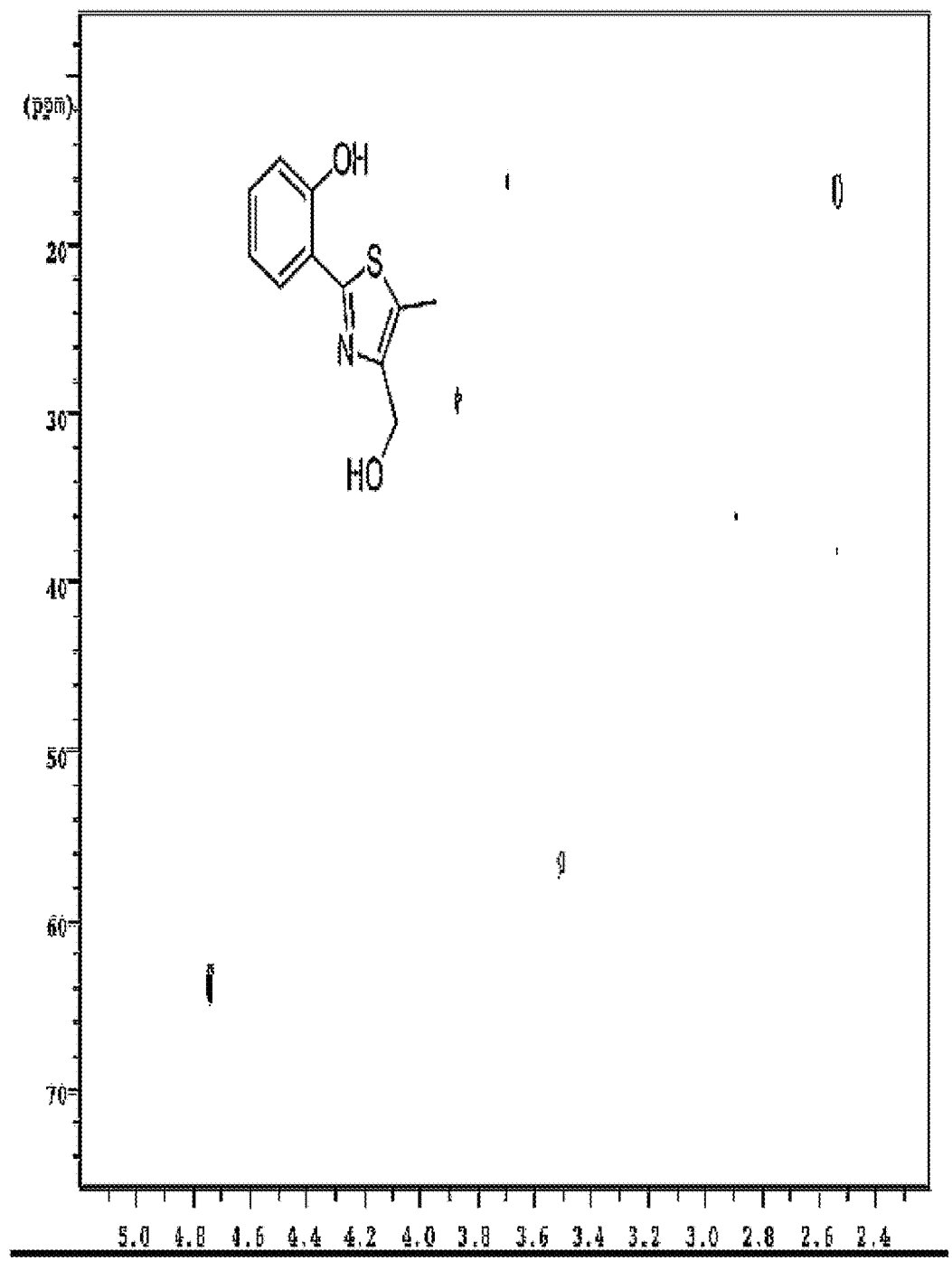
FIG. 17 shows a representative HSQC spectrum of an exemplary compound.
Figure 18:
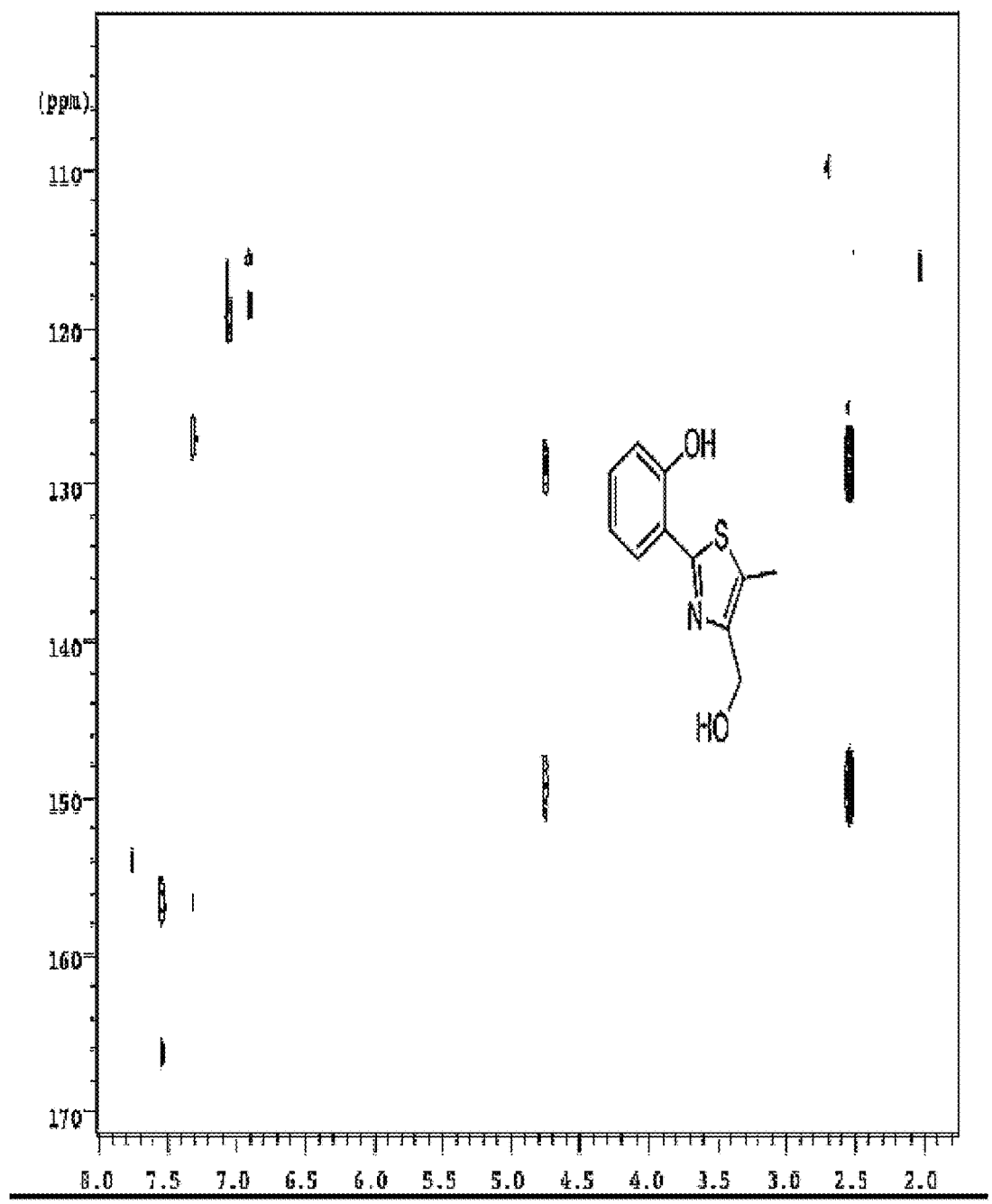
FIG. 18 shows a representative HMBC spectrum of an exemplary compound.
Figure 30:
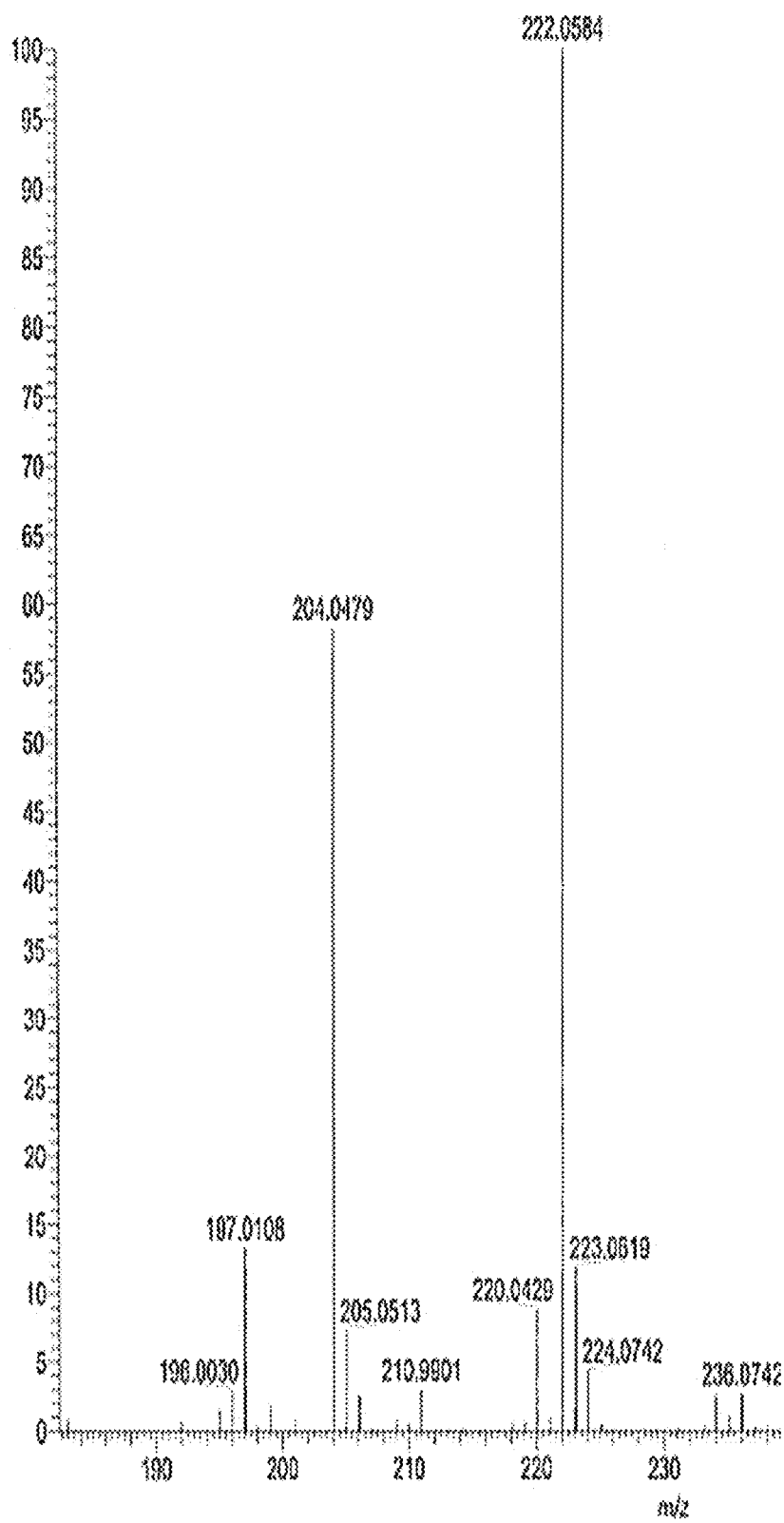
FIG. 30 shows a representative HRESIMS spectrum of an exemplary compound.

The molecular formula $C_{11}H_{10}NO_2S$ was assigned to compound 4 on the basis of HRESIMS analysis (m/z 222.0584 [M+H]+; FIG. 30) and NMR experiments ($^1$H NMR, FIG. 16 and $^{13}$C NMR, FIG. 17). In contrast to compound 2, compound 4 has NMR signals for a quaternary double bond ($\delta_C$ 128.6 qC, 149.5 qC) instead of the two sp3 hybridized carbons in compound 2. A singlet was assigned to a vinylic methyl ($\delta_H$ 2.52 s, $\delta_C$ 10.9 CH$_3$). These data indicate that compound 4 was the 4',5'-dehydro derivative of compound 2. This was also supported by the HMBC correlations (FIG. 18) from H-6' to C4' and C5' and from H-7' to C4' and C5'. Key HMBC correlations are shown in FIG. 2.

| position | $\delta_C$, mult | $\delta_H$ (J in Hz) |
|---|---|---|
| 1 | 115.4, qC | |
| 2 | 156.6, qC | |
| 2-OH | | 11.90, brs |
| 3 | 126.8, CH | 7.53, d (8.5) |
| 4 | 119.2, CH | 6.89, dd (8.5, 7.3) |
| 5 | 131.2, CH | 7.29, dd (8.2, 7.3) |
| 6 | 117.5, CH | 7.03, d (8.2) |
| 2' | 166.3, qC | |
| 4' | 128.6, qC | |
| 5' | 149.5, qC | |
| 6' | 10.9, CH$_3$ | 2.52, s |
| 7' | 58.5, CH$_2$ | 4.73, s | e. 2-(2-hydroxyphenyl)-5-methylthiazole-4-carbaldehyde (5)

Compound 5 is a white solid (CHCl$_3$); UV (MeOH) $\lambda_{max}$ 219 (4.10), 289 (3.84), 321 (3.77) nm; IR (film) $\nu_{max}$: 2835, 1700, 1670, 1535, 1415, 1430, 1295, 1250, 745 cm$^{-1}$; $^1$H and $^{13}$C NMR (see below); HRESIMS m/z 220.0427 [M+H]+ (calcd for $C_{11}H_{10}NO_2S$, 220.0432).

Figure 19:
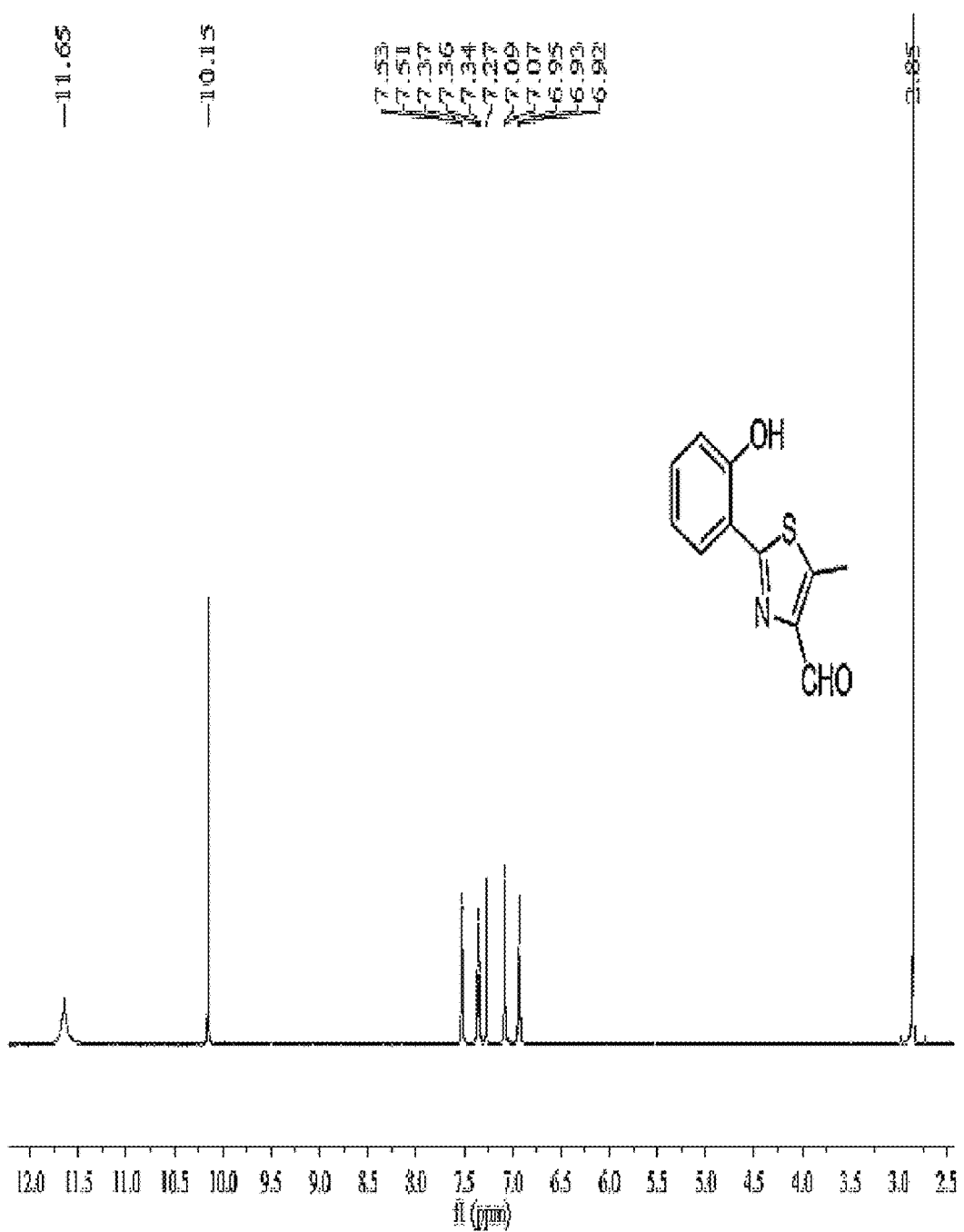
FIG. 19 shows a representative $^1$H NMR spectrum of an exemplary compound.
Figure 20:
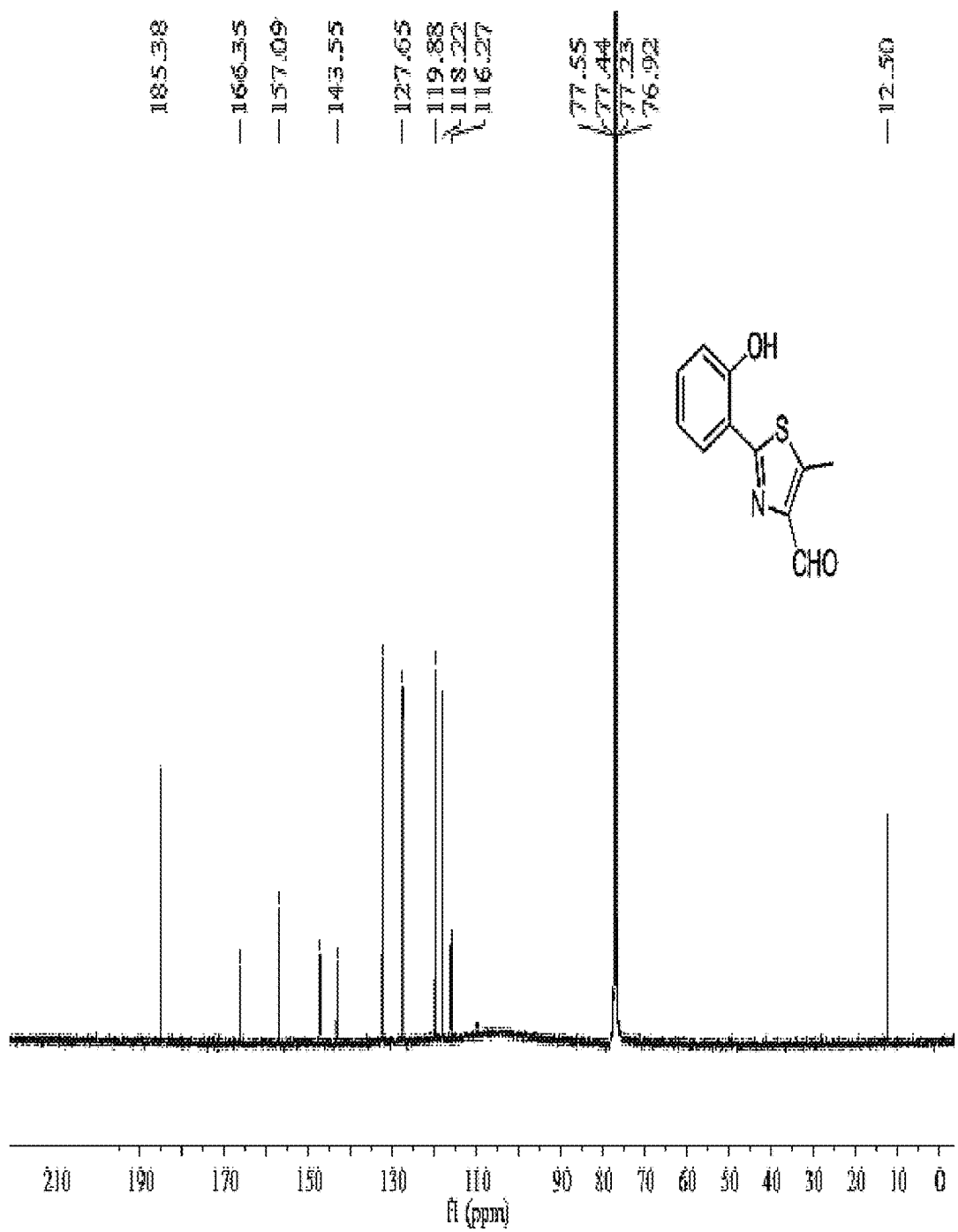
FIG. 20 shows a representative $^{13}$C NMR spectrum of an exemplary compound.
Figure 21:
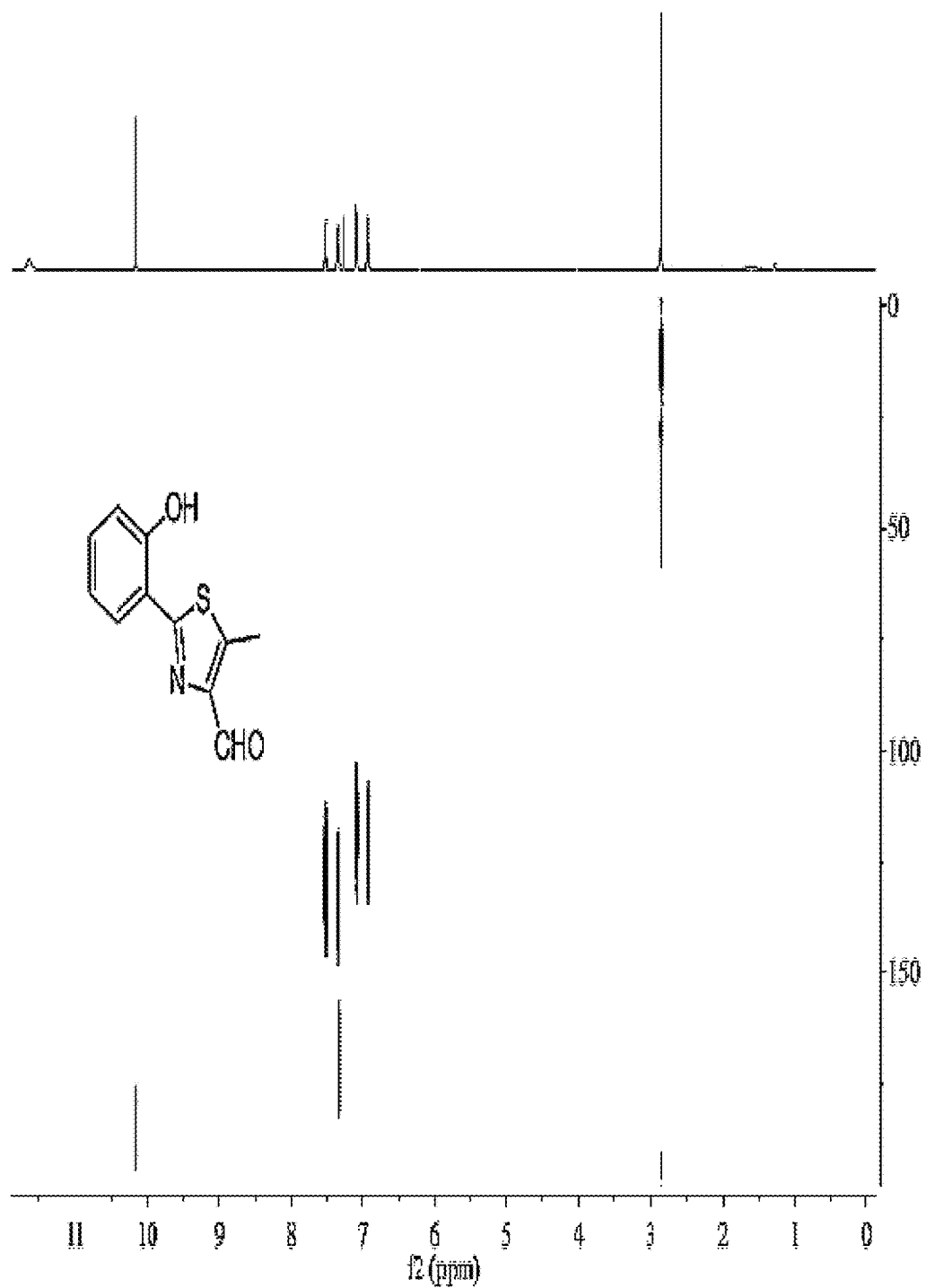
FIG. 21 shows a representative HSQC spectrum of an exemplary compound.
Figure 22:
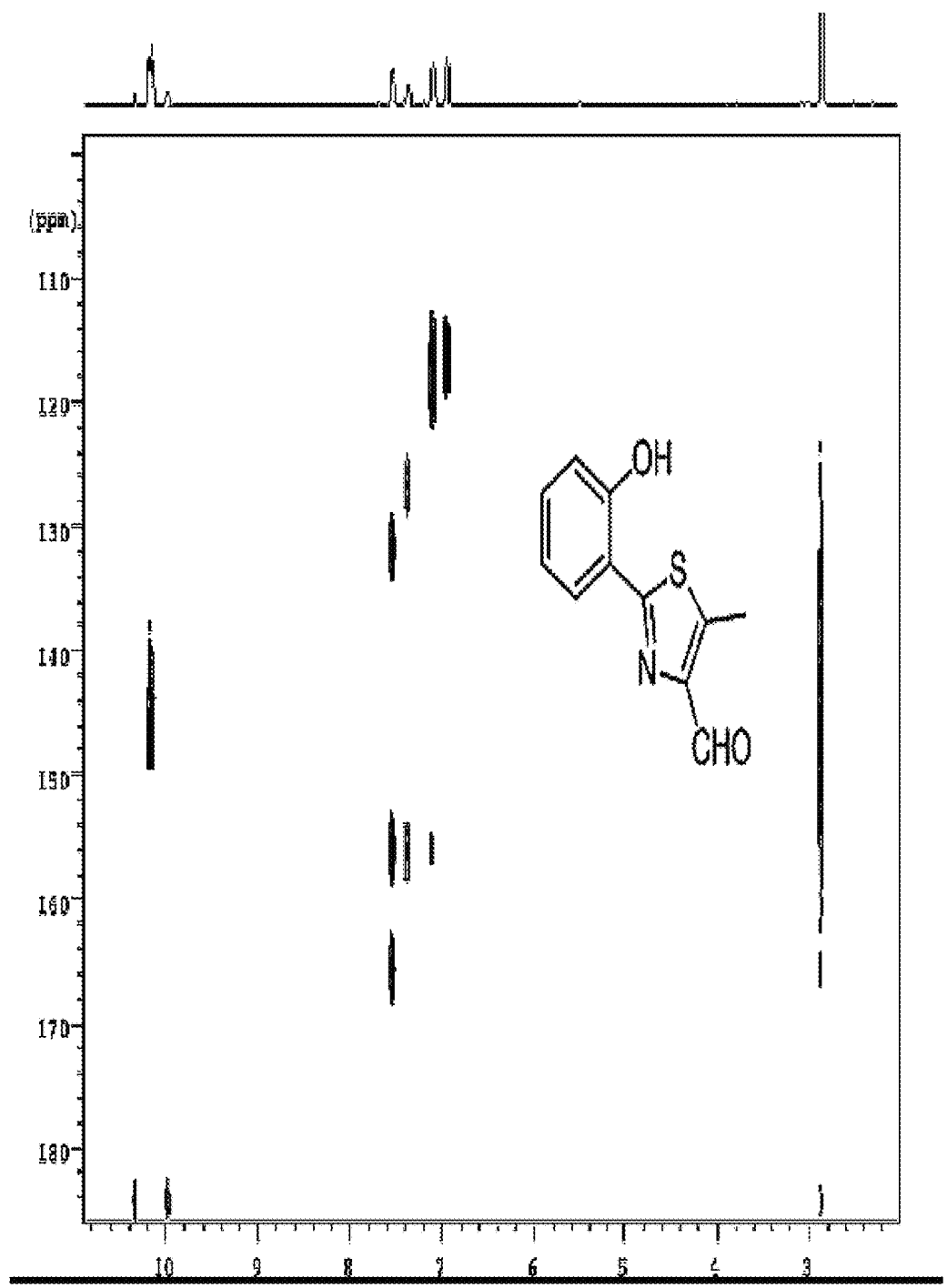
FIG. 22 shows a representative HMBC spectrum of an exemplary compound.
Figure 31:
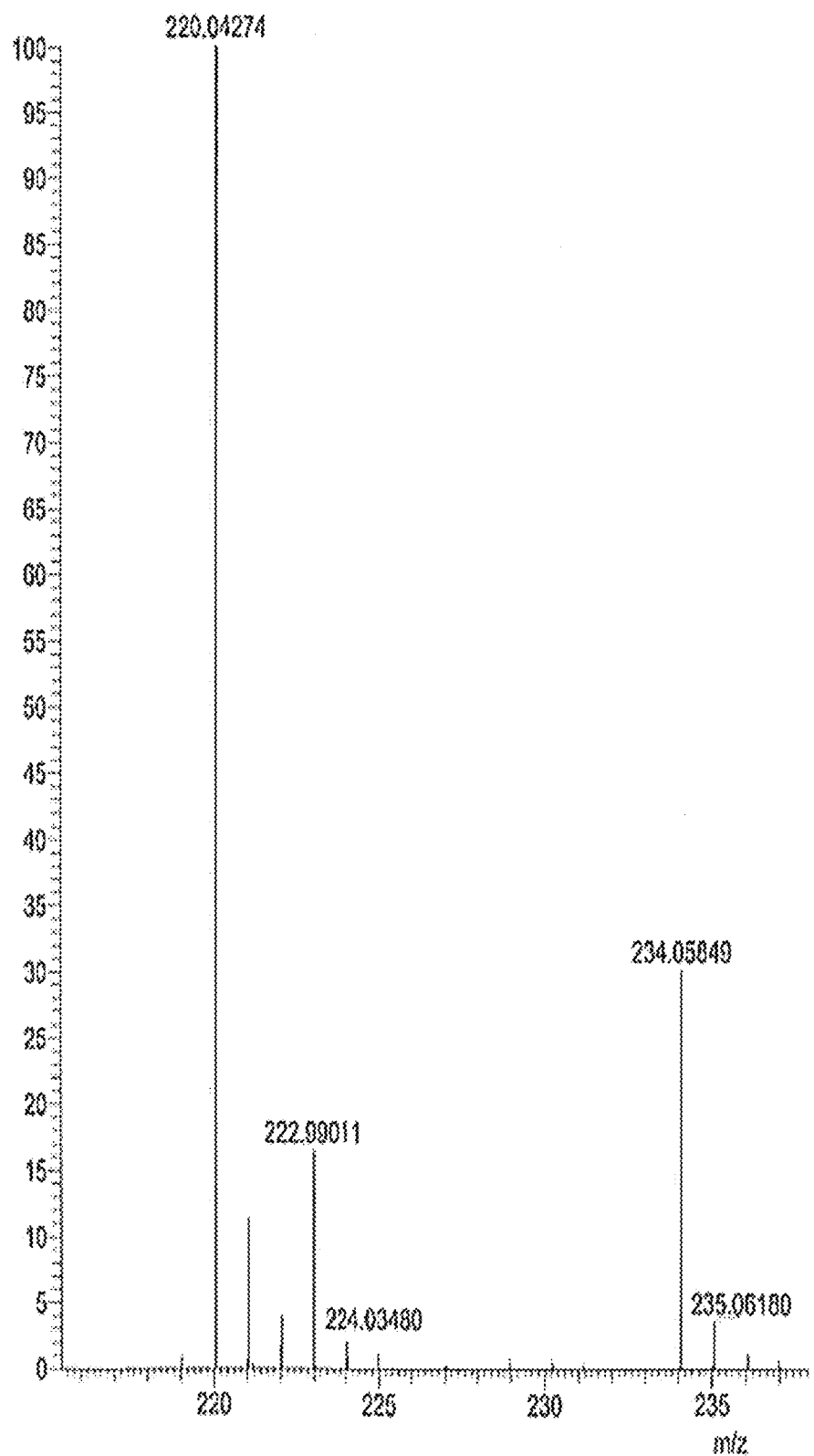
FIG. 31 shows a representative HRESIMS spectrum of an exemplary compound.

The molecular formula for compound 5, $C_{11}H_8NO_2S$, was derived from NMR data ($^1$H NMR, FIG. 19 and $^{13}$C NMR, FIG. 20) and the HRESIMS ion at m/z 220.0427 [M+H]+ (FIG. 31). The NMR data were very similar to that of compound 4, except that compound 5 had an aldehyde group ($\delta_C$ 185.4 CH) that was assigned to C7'. The chemical shift of the aldehyde carbon indicated it was conjugated with C4'-C5' double bond. This was also supported by the HMBC correlations (FIG. 22) from H-6' to C4' and C5' and from H-7' to C4' and C5'. The HSQC spectrum is shown in FIG. 21. Key HMBC correlations are shown in FIG. 2.

| position | $\delta_C$, mult | $\delta_H$ (J in Hz) |
|---|---|---|
| 1 | 116.3, qC | |
| 2 | 157.1, qC | |
| 2-OH | | 11.64, brs |
| 3 | 127.6, CH | 7.51, d (8.5) |
| 4 | 119.9, CH | 6.92, dd (8.5, 7.5) |
| 5 | 132.5, CH | 7.35, dd (8.5, 7.3) |
| 6 | 118.2, CH | 7.07, d (8.3) |
| 2' | 166.3, qC | |
| 4' | 143.5, qC | |
| 5' | 147.3, qC | |
| 6' | 12.5, $CH_3$ | 2.86, s |
| 7' | 185.4, qC | 10.15, s | f. 2-(2-hydroxyphenyl)-5-methylthiazole-4-carboxamide (6)

Compound 6 is a pale yellow solid (MeOH); UV (MeOH) $\lambda_{max}$ 212 (4.11), 279 (3.87), 321 (3.79) nm; IR (film) $v_{max}$: 2924, 1670, 1595, 1490, 1475, 1415, 1360, 1150, 750 $cm^{-1}$; $^1H$ and $^{13}C$ NMR (see below); HRESIMS m/z 235.0546 $[M+H]^+$ (calcd for $C_{11}H_{11}N_2O_2S$, 234.0463).

Figure 23:
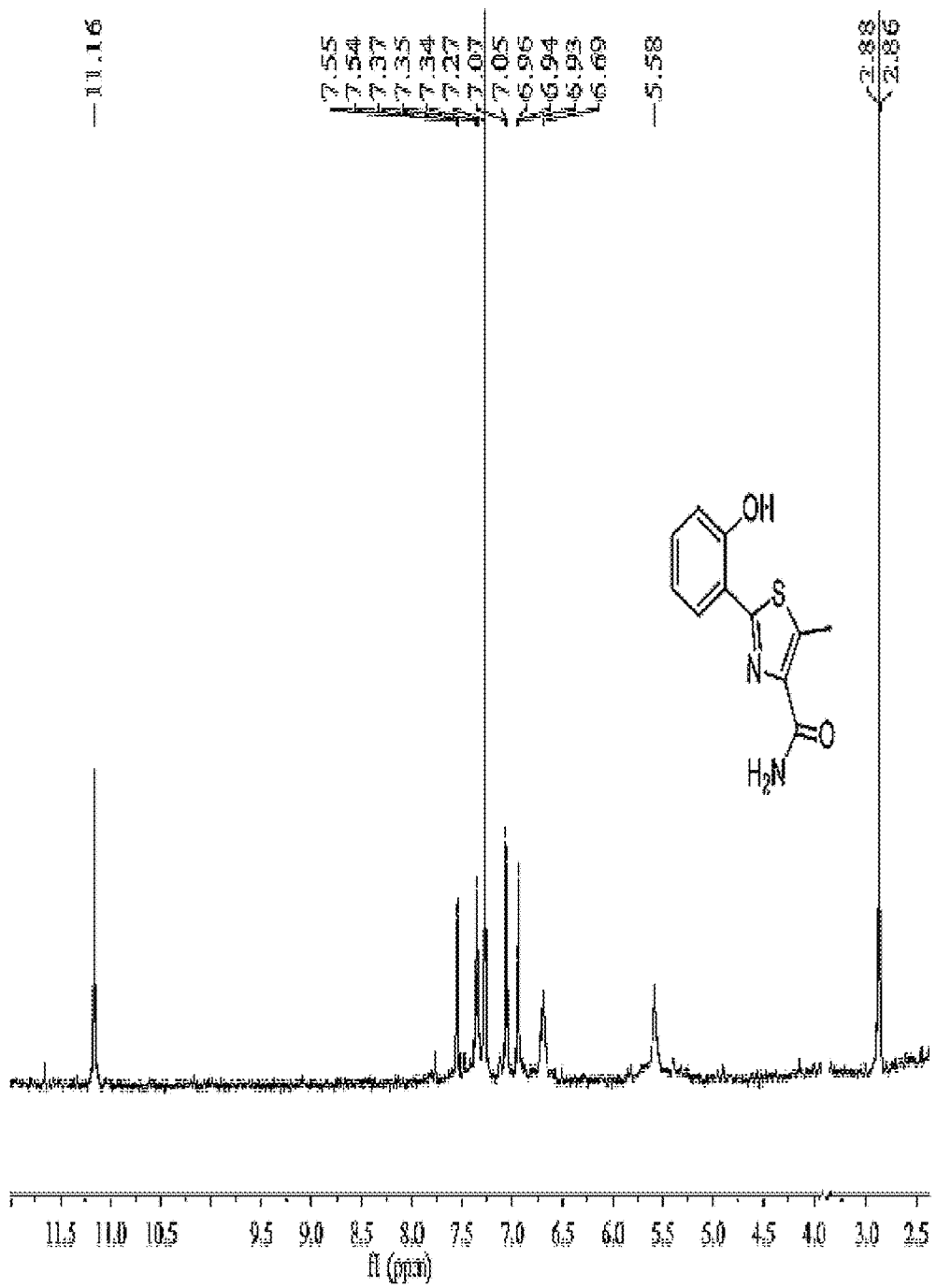
FIG. 23 shows a representative $^1$H NMR spectrum of an exemplary compound.
Figure 24:
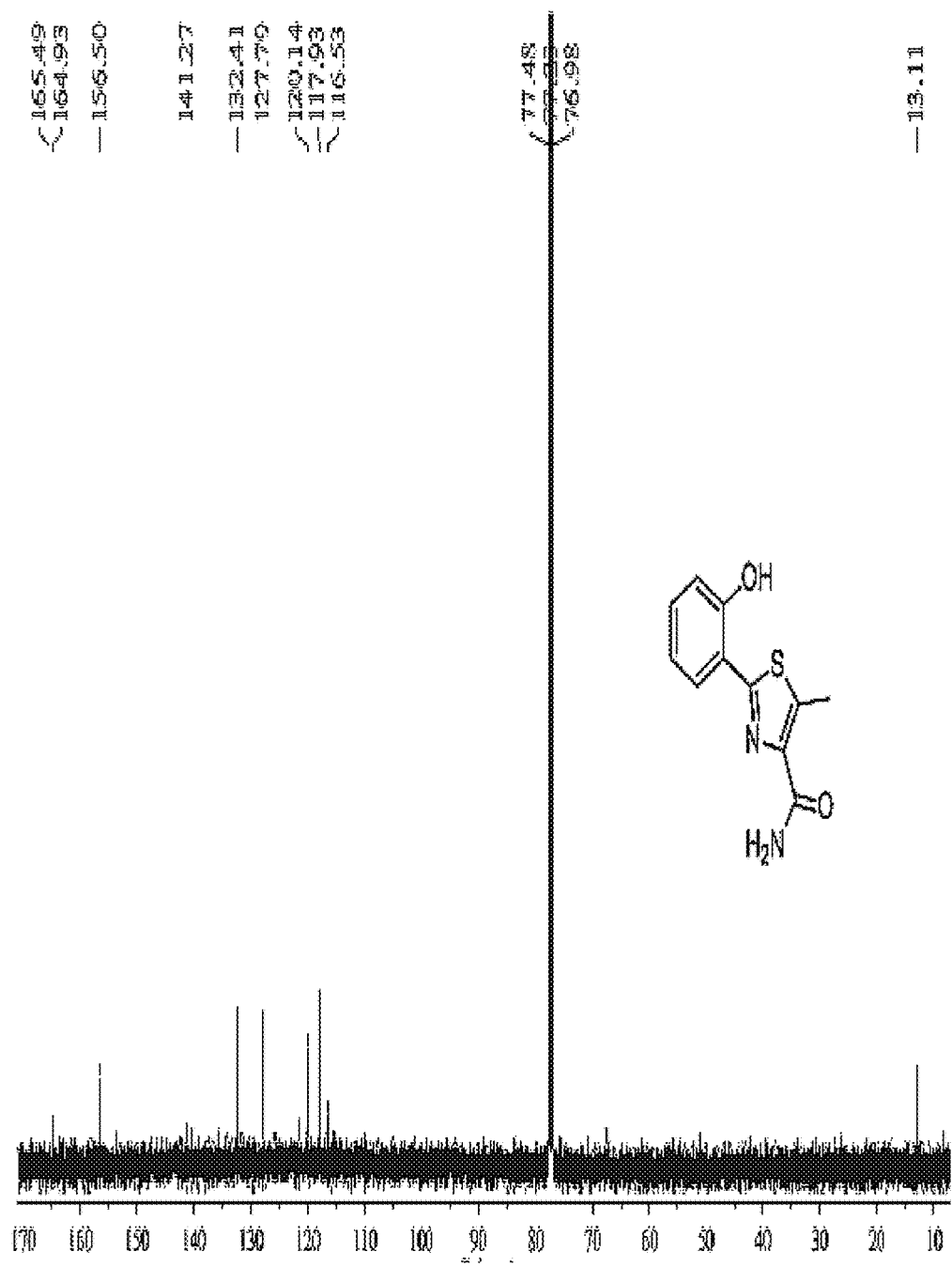
FIG. 24 shows a representative $^{13}$C NMR spectrum of an exemplary compound.
Figure 25:
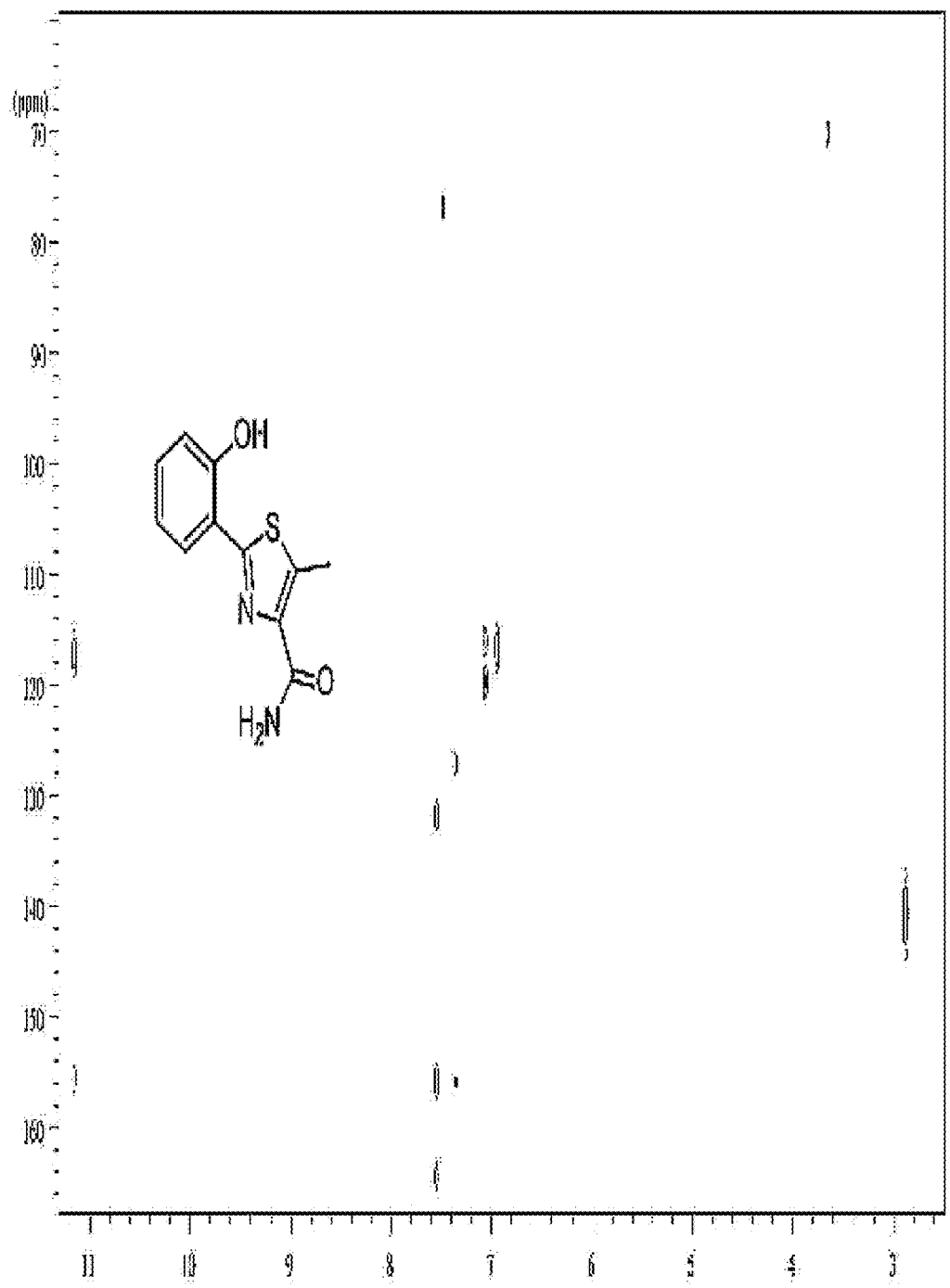
FIG. 25 shows a representative HMBC spectrum of an exemplary compound.
Figure 32:
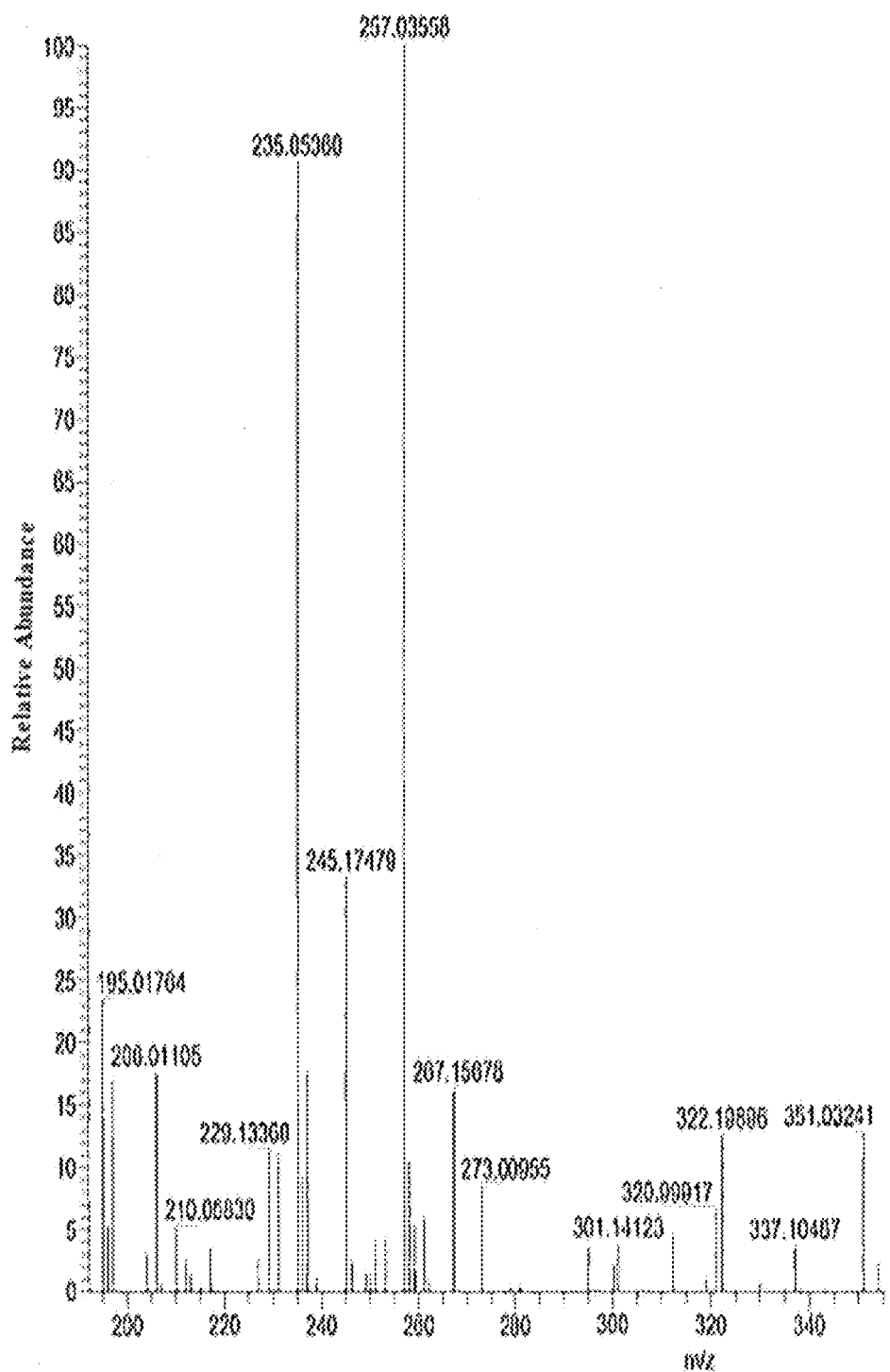
FIG. 32 shows a representative HRESIMS spectrum of an exemplary compound.

The molecular formula $C_{11}H_{10}N_2O_2S$ was assigned to compound 6 on the basis of HRESIMS analysis (m/z 235.0546 $[M+H]^+$; FIG. 32) and NMR experiments ($^1H$ NMR, FIG. 23 and $^{13}C$ NMR, FIG. 24). Analysis of the NMR spectra of compound 6 showed this compound to have a carbonyl at 164.9 ppm instead of the aldehyde group present in compound 5. Based on the molecular formula, the carbonyl at 164.9 ppm was assigned to a methanamide group located at C-5'. The HMBC spectrum is shown in FIG. 25. Key HMBC correlations are shown in FIG. 2.

| position | $\delta_C$, mult | $\delta_H$ (J in Hz) |
|---|---|---|
| 1 | 116.5, qC | |
| 2 | 156.5, qC | |
| 2-OH | | 11.16, s |
| 3 | 127.8, CH | 7.55, d (7.0) |
| 4 | 120.1, CH | 6.94, dd (7.7, 7.5) |
| 5 | 132.4, CH | 7.35, dd (7.4, 7.4) |
| 6 | 117.9, CH | 7.06, d (8.1) |
| 2' | 165.5, qC | |
| 4' | 121.6, qC | |
| 5' | 141.3, qC | |
| 6' | 13.1, $CH_3$ | 2.88, s |
| 7' | 164.9, qC | | g. 2-(2-hydroxyphenyl)thiazole-4-carboxamide (7)

Compound 7 is a pale yellow solid (MeOH); UV (MeOH) $\lambda_{max}$ 211, 276, 319 nm; $^1H$ NMR (CDCl$_3$, 500 MHz) δ 7.05 (1H, d, J=8.3 Hz, H-3), 7.36 (1H, dd, J=8.5, 7.3 Hz, H-4), 6.95 (1H, dd, J=8.5, 7.5 Hz, H-5), 7.65 (1H, d, J=8.5 Hz, H-6), 8.14 (1H, s, H-4'); $^{13}C$ NMR (CDCl$_3$, 125 MHz) δ 116.4 (C, C-1), 155.9 (C, C-2), 117.2 (CH, C-3), 132.6 (CH, C-4), 120.0 (CH, C-5), 127.5 (CH, C-6), 169.5 (C, C-2'), 123.4 (CH, C-4'), 148.4 (C, C-5'), 162.1, (C, C-7'). ESIMS m/z 221 $[M+H]^+$.

h. 2-(2-hydroxyphenyl)-4,5-dihydrothiazole-4-carboxamide (8)

Compound 8 is a pale yellow solid (MeOH); UV (MeOH) $\lambda_{max}$ 211, 252, 312 nm; $^1H$ NMR (CDCl$_3$, 500 MHz) δ 11.95 (1H, s, 2-OH), 7.02 (1H, d, J=10.0 Hz, H-3), 7.41 (1H, dd, J=10.0, 10.0 Hz, H-4), 6.93 (1H, dd, J=9.9, 9.4 Hz, H-5), 7.47 (1H, d, J=9.9 Hz, H-6), 3.72 (1H, m, H-4'), 5.32 (1H, t, J=9.9 Hz, H-7'); $^{13}C$ NMR (CDCl$_3$, 125 MHz) δ 116.1 (C, C-1), 159.0 (C, C-2), 117.5 (CH, C-3), 131.1 (CH, C-4), 119.7 (CH, C-5), 134.2 (CH, C-6), 172.7 (C, C-2'), 34.2 ($CH_2$, C-4'), 78.0 (CH, C-5'), 176.4, (C, C-7'). HRESIMS m/z 223.0538 $[M+H]^+$ (calcd for $C_{10}H_{11}N_2O_2S$, 223.0541).

6. Preparation of (S)- and (R)-MTPA Esters

Figure 26:
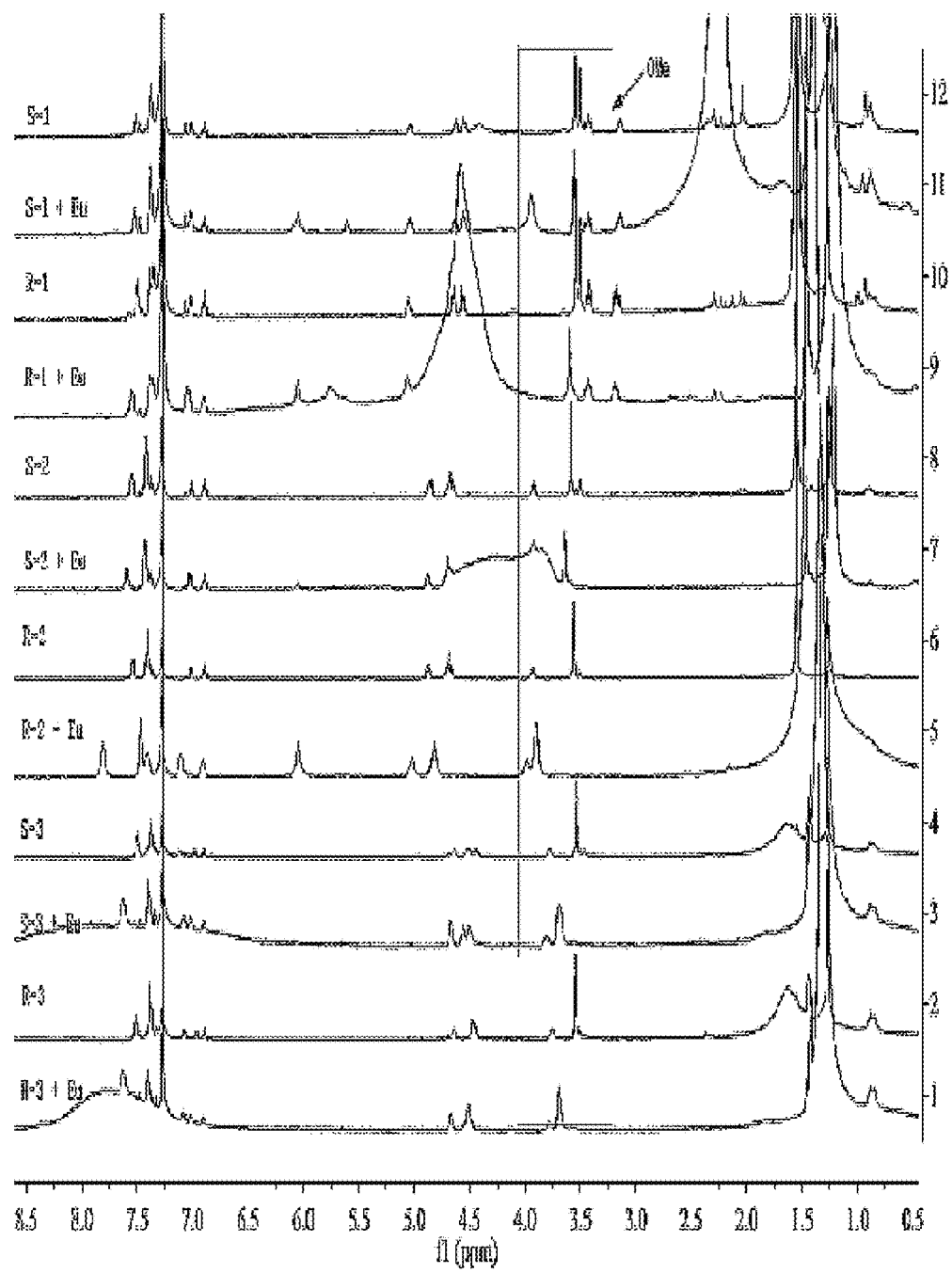
FIG. 26. shows representative $^1$H NMR spectra of MTPA esters of exemplary compounds.

Compound 1 (100 μg), 2 (500 μg) and 3 (100 μg) were separately transferred into clean reaction bottles and dried completely under vacuum. Pyridine (0.5 mL) and α-methoxy-α-(trifluoromethyl)phenylacetyl chloride (1 equiv) were added into the reaction bottle quickly under a $N_2$ gas stream and then stirred for 12 h at room temperature. The organic layer was then washed with water and concentrated under reduced pressure to obtain the ester. Final purification was achieved by HPLC (90% MeOH, 4.0 mL/min) $^1H$ NMR spectra for MTPA esters for compounds 1, 2, and 3 are shown in FIG. 26.

7. Chiral Analysis with Eu(fod)$_3$

Figure 4:
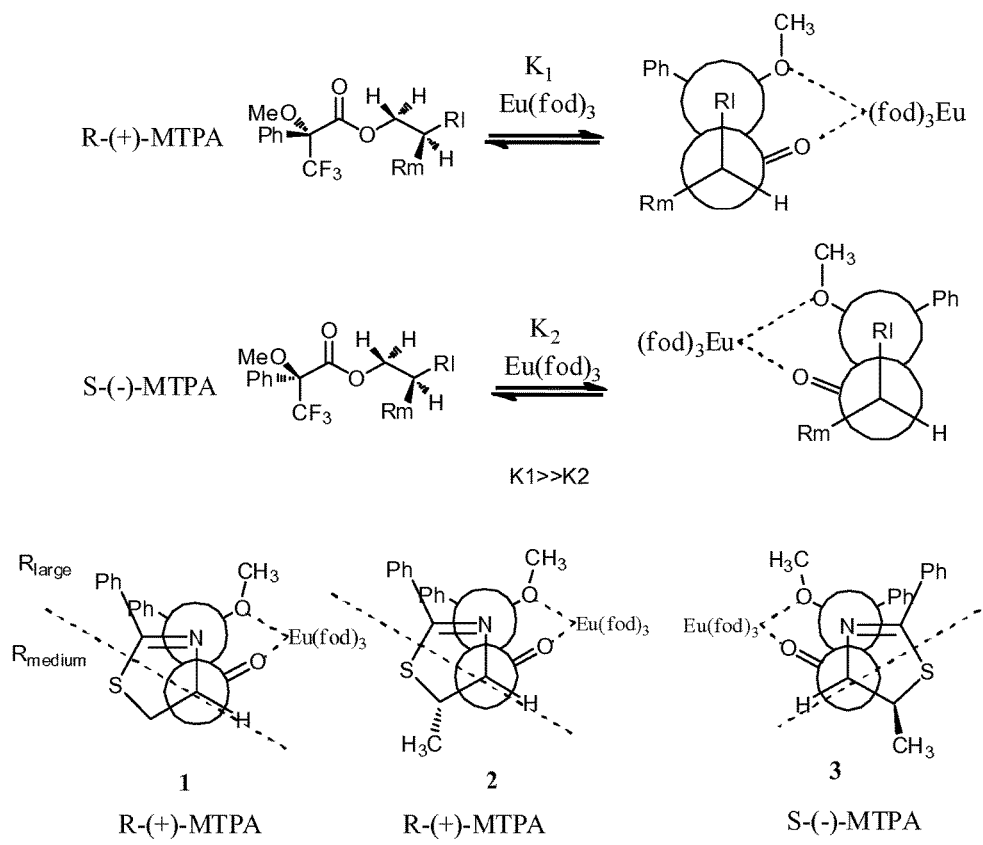
FIG. 4 shows application of lanthanide-induced shift analysis used in analysis of exemplary compounds.

The method of Yamaguchi and Yasuhara for determination of the absolute configurations of primary alcohols with the chiral center at the 2-position to determine the configuration of compounds 2 and 3. In this approach, an acyclic alcohol is converted to the corresponding (R)-(+)-MTPA ester and (S)-(−)-MTPA ester. The magnitude of lanthanoid induced shift (LIS) by Eu(fod)$_3$ for the methoxyl group of the (R)-(+)-MTPA ester is larger than that of the (S)-(−)-MTPA ester when the chiral center is in R-configuration. Sugimoto applied this method to a primary alcohol in which a hydroxymethyl group is situated on the chiral ring carbon atom of the carbocycle. Len et al. assumed that complexation of europium salts with both oxygens of the ester and methoxy groups induced the existence of different conformers. Chemical shift differences are measured for OCH$_3$ groups of (R)- and (S)-MTPA esters, allowing determination of the absolute configuration of alcohols. $K_1$ and $K_2$ are the equilibrium constants between the complexed and the free forms of diastereoisomeric Mosher's esters; Δδ OCH3=difference between the chemical shift for the methoxy group of the esters with and without the Europium salt. The structural relationship of the complexed and free forms of the diastereoisomeric Mosher's esters is shown in FIG. 4.

Compounds 1-3 were transformed in to the corresponding (R)-(+)-MTPA esters and (S)-(−)-MTPA esters as described above. Each MTPA ester of 1-3 was added to an NMR tube in CDCl$_3$, and an equimolar mixture of Eu(fod)$_3$ was added to each tube. The difference in chemical shift with and without the chiral reagent was recorded: $\Delta\delta_{OCH3}$ (ppm)= $\Delta\delta_{OCH3}$ (with Eu(fod)$_3$)−$\Delta\delta_{OCH3}$ (without Eu(fod)$_3$. $^1H$ NMR spectra for MTPA esters for compounds 1, 2, and 3 are shown in FIG. 26.

The LIS values of the methoxyl groups were given are given below. For 1 and 2, the LIS values for (R)-(+)-MTPA esters were larger than (S)-(−)-MTPA esters, indicating that the chiral centers at C5' of compounds 1 and 2 were in the R-configurations. Compound 3 showed larger LIS values for the (S)-(−)-MTPA ester, indicating that the chiral center at C5' of 3 was in an S-configuration. These conclusions were consistent with the circular dichroism spectra of compounds 1-3: the CD spectra of compound 1 and 2 were very similar, but opposite to that of compound 3 (FIG. 3).

| Compound MTPA esters | $\Delta\delta_{OCH_3}$ (S)- | (R)- | Configuration of C5' |
|---|---|---|---|
| 1 | +0.01 | +0.05 | R |
| 2 | +0.05 | +0.34 | R |
| 3 | +0.16 | +0.13 | S |

8. Synthesis of (R)-(2-(2-hydroxyphenyl)-4,5-dihydrothiazol-4-yl)methyl 4-bromobenzoate (1a)

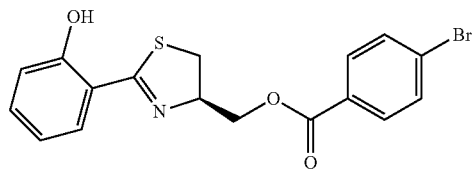 [SMILES: O=C(OC[C@@H]1CSC(c2ccccc2O)=N1)c1ccc(Br)cc1]

Figure 5:
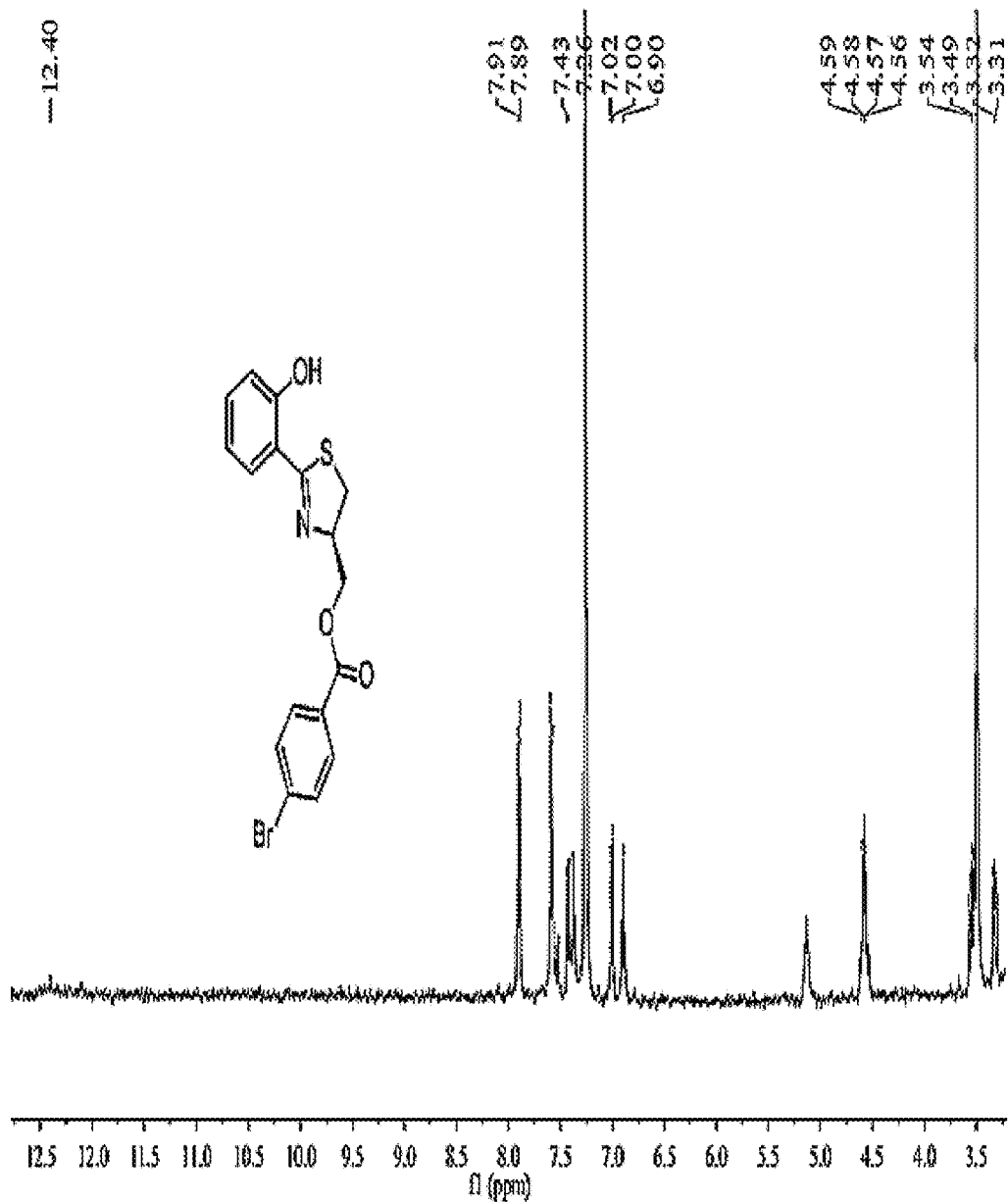
FIG. 5 shows a representative $^1$H NMR spectrum of an exemplary compound.

To a stirred suspension of 1 (1.0 mg) in dry $CH_2Cl_2$ (2 mL) was added $Et_3N$ (1 mL) and p-$BrC_6H_4COCl$ (3 mg) at room temperature. Four hours later the reaction was quenched by adding $H_2O$ (2 mL). The mixture was extracted with EtOAc (3×5 mL), and the EtOAc solution was dried on anhydrous $Na_2SO_4$ and evaporated at reduced pressure. The residue was subjected to $C_{18}$ HPLC (95% MeOH/$H_2O$) to give 1a (1.1 mg). $^1$H NMR data of compound 1a (CDCl$_3$, 400 MHz) δ: 7.36~7.99 (8H, m, ArH), 4.92 (1H, m, H-4'), 4.35, 4.28 (each 1H, m, H-7'), 3.46, 3.24 (each 1H, m, H-4'). ESI MS: m/z 392.0, 394.0 [M+H]$^+$ (FIG. 5).

9. Dorsal Root Ganglion (DRG) Assay

For details of the isolation and culture of dorsal root ganglion neurons see Light et al. Briefly, dorsal root ganglia (DRG) cells from cervical and lumbar regions were obtained from mice and used in an assay with bacterial culture extracts and pure compounds. DRG cells were suspended in medium with additives and loaded with Fura-2 AM (Molecular Probes), a fluorescent dye used to measure intracellular calcium levels. Experiments were performed at room temperature (20 to 25° C.) in a 24-well plate format using fluorescence microscopy. Individual cells were treated as single samples, so that the individual responses of diverse neuron subtypes from the DRG could be examined. After baseline measurements, the cells were treated with 25 mM KCl solution and then washed. After return to baseline, bacterial extracts, fractions, or pure compounds were applied. This solution was then later replaced with 25 mM KCl solution. The use of KCl permitted observation of direct, modulatory, as well as inhibitory and excitatory effects of the samples assayed.

Figure 33:
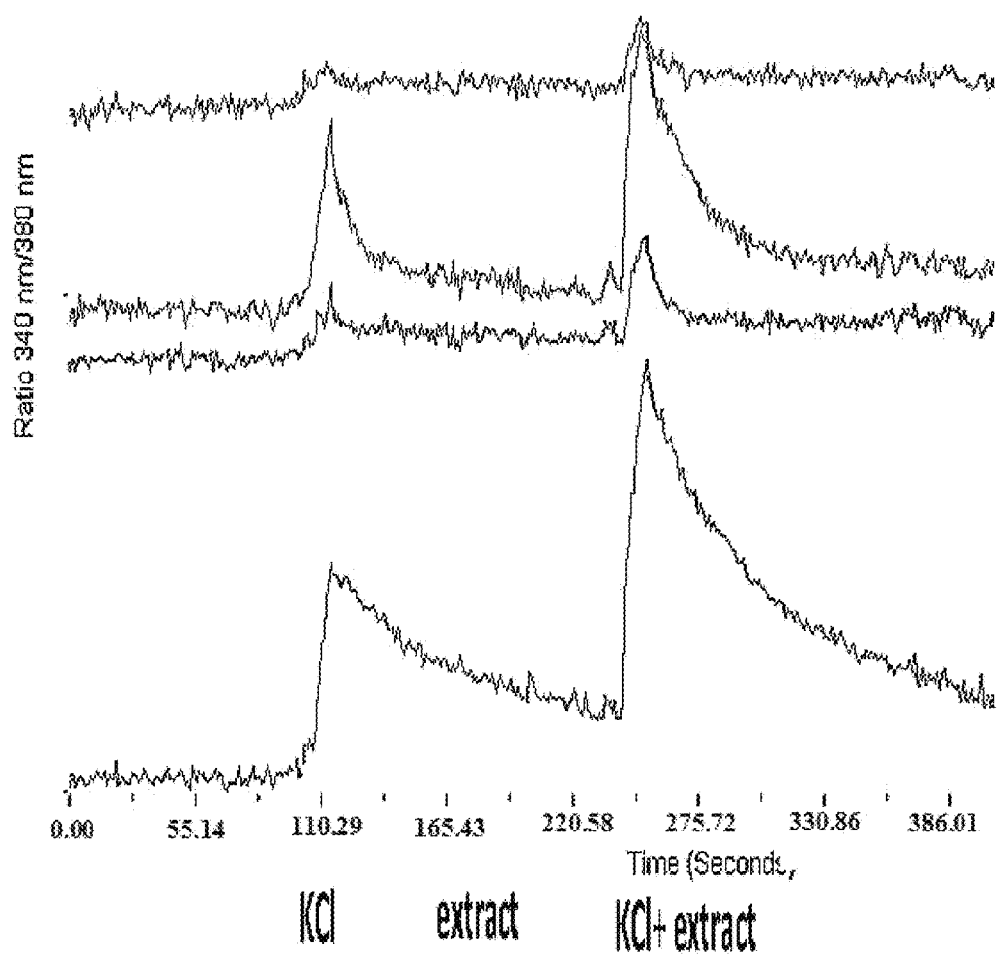
FIG. 33 shows representative dorsal root ganglion (DRG) assay results for an extract from Streptomyces sp. CP32.
Figure 34:
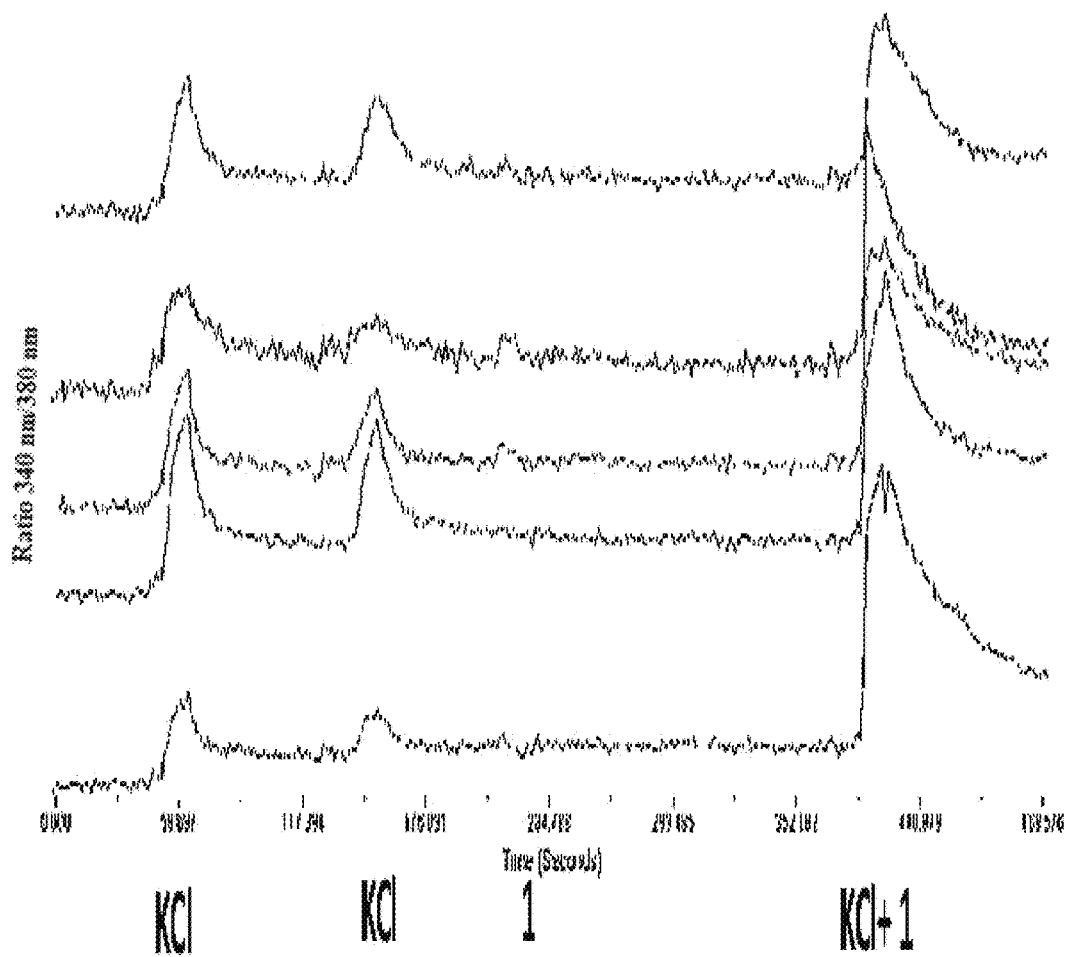
FIG. 34 shows representative DRG assay results for an exemplary compound.
Figure 35:
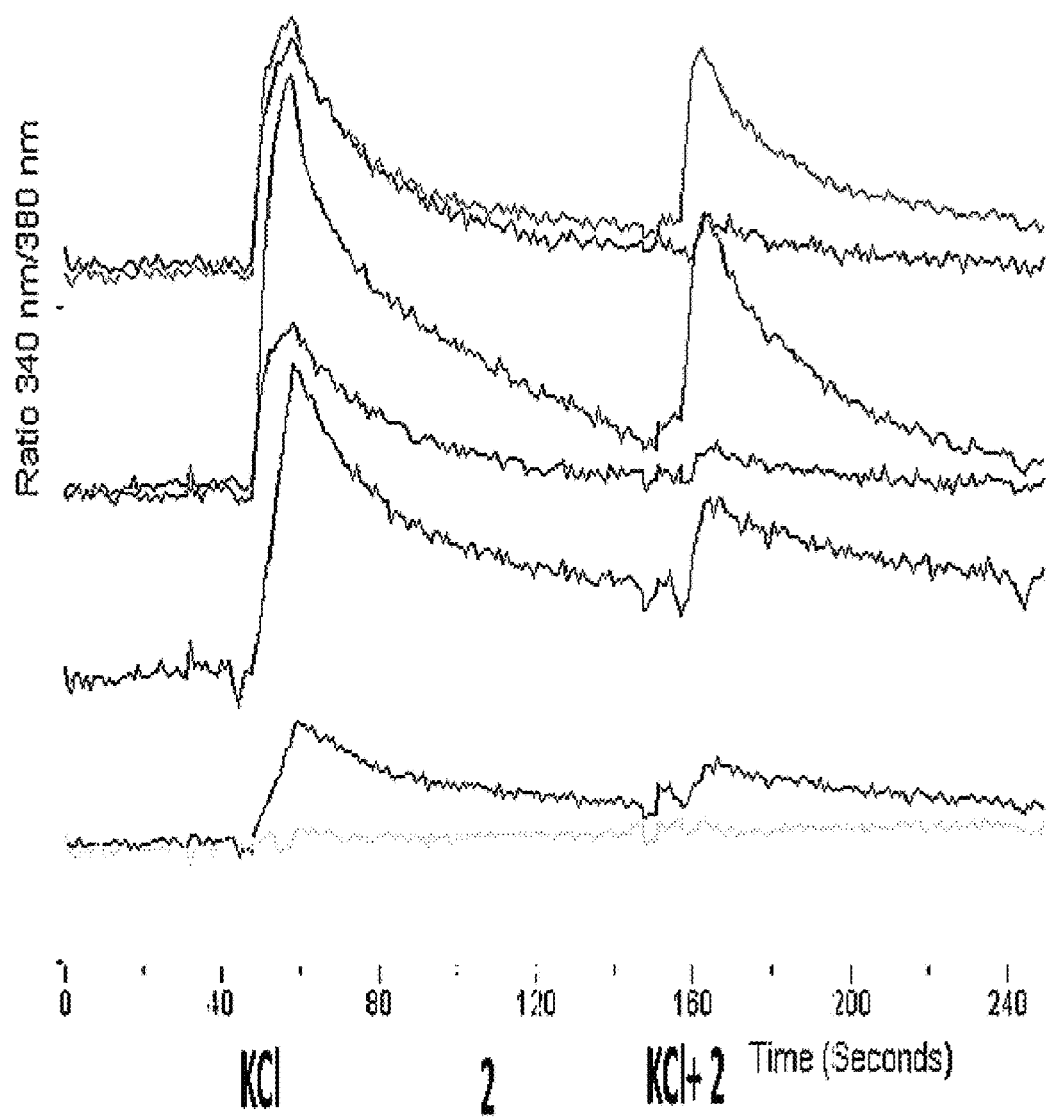
FIG. 35 shows representative DRG assay results for an exemplary compound.
Figure 36:
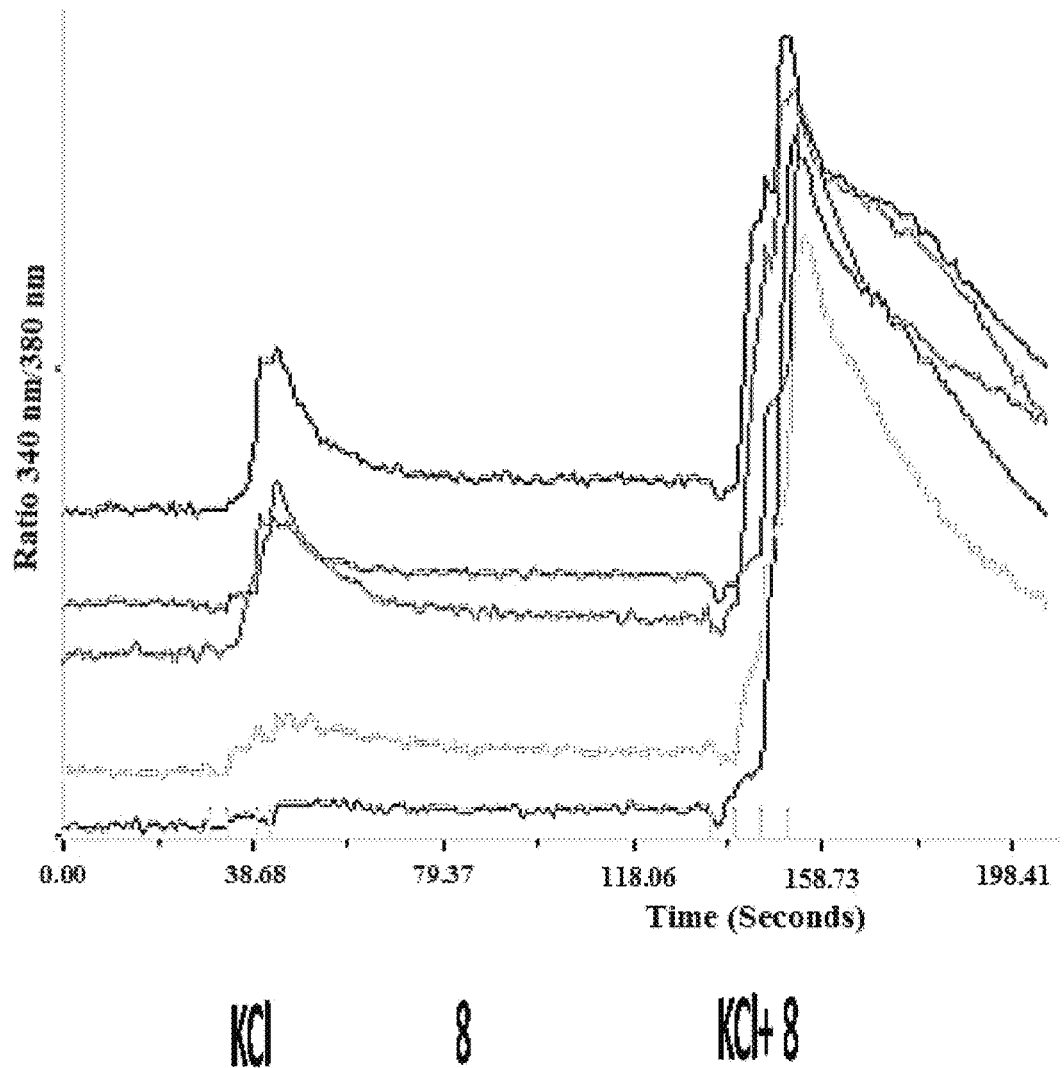
FIG. 36 shows representative DRG assay results for an exemplary compound.

Representative data for assay results obtained with a sample of crude extract (100 μg/mL; FIG. 33), as well as compounds 1, 2, and 8 (20 μg/mL; respectively, FIGS. 33, 34, 35 and 36). The y-axis indicates the ratio between 340 nm and 380 nm fluorescence. A higher value indicates more $Ca^{2+}$ in the cell. The x-axis indicates time. Each line indicates an individual DRG cell followed over the experimental time course. In each experiment, KCl is applied either once or twice, the compounds or extracts are incubated with cells, then the compound is co-applied with KCl. The data show an increase in excitation in the presence of crude extract when the extract is co-applied in the presence of KCl (FIG. 33). The results also show an excitatory response (or increase in $Ca^{2+}$ influx) in the presence of compound 1 (FIG. 34), an inhibitory response (or decrease in $Ca^{2+}$ influx) in the presence of 2 (FIG. 35), and an excitatory response (or increase in $Ca^{2+}$ influx) in the presence of compound 8 (FIG. 36). An observable effect in these neurons requires a relatively high dose that essentially completely blocks the target.

In the DRG assay on purified compounds, two major metabolites (1 and 8) observably increased $Ca^{2+}$ influx at 20 μg/mL and were responsible for the activity of the crude extract of CP32, while compound 2 showed a decreased $Ca^{2+}$ influx 10. Receptor Assays Potential molecular targets and potencies underlying the observations made in the DRG assay were assessed by further screening of compounds 1, 2, 5, and 7-10 at the National Institute of Mental Health's Psychoactive Drug Screening Program (PDSP). Receptor affinity assays were carried out according to methods as described at http://pdsp.med.unc.edu/ (accessed on Oct. 13, 2010).

Activity was assayed for the following receptors: (1) muscarinic receptors: M1, M2, M3, M4, M5; (2) Serotonin receptors: 5ht1a, 5ht1b, 5ht1d, 5ht1e, 5ht2a, 5ht2b, 5ht2c, 5ht3, 5ht4, 5ht5a, 5ht6, 5ht7; (3) GABA receptors: BZP (Rat Brain Site), GABA A, GABA B; (4) histaminergic receptors: H1, H2, H3, H4; (5) Dopamine receptors: D1, D2, D3, D4, D5; (6) Transporters: NET, SERT, DAT; (7) Opiate receptors: DOR, KOR, MOR; (8) Adrenergic receptors: Alpha1A, Alpha1B, Alpha1D, Alpha2A, Alpha2B, Alpha2C, Beta1, Beta2, Beta3; and, (9) others: Sigma 1, Sigma 2, Ca+Channel.

A primary assay was performed against the above targets at a final concentration of 10 μM of each compound. Initial hits were obtained in radioligand displacement assays. For targets where significant activity was detected, secondary binding assays were performed, and Ki values were calculated using radioligand displacement with test compound concentrations from 1 to 10,000 nM. Representative activity is highlighted in the table below showing in radioligand displacement activity at 10 μM of the in dicated compound. Ki was determined as indicated.

| Compound* | Condition | 5HT2B | DAT | H1 | KOR | $Ca^{2+}$ Channel |
|---|---|---|---|---|---|---|
| 1 | inhibition (10 μM) | 79.2% | −1.5% | 39.0% | 57.2% | −0.7% |
|   | Ki (nM) | 1360 ± 110 | — | — | >10000 | — |

-continued

| Compound* | Condition | 5HT2B | DAT | H1 | KOR | Ca2+ Channel |
|---|---|---|---|---|---|---|
| 2 | inhibition (10 μM) | 89.7% | 6.0% | 45.8% | 60.8% | — |
|   | Ki (nM) | 505 ± 29 | — | — | >10000 | 6601 |
| 5 | inhibition (10 μM) | 77.0% | 88.3% | 42.5% | 37.1% | -18.9% |
|   | Ki (nM) | 1541 ± 134 | 5185 | — | — | — |
| 7 | inhibition (10 μM) | 84.9% | 2.4% | 88.0% | 31.8% | 29.6% |
|   | Ki (nM) | 1031 ± 76 | — | 517 ± 28 | — | — |
| 8 | inhibition (10 μM) | 65.8% | 13.8% | 71.6% | 50.4% | -3.4% |
|   | Ki (nM) | 1260 ± 99 | — | 678 ± 46 | 3708 ± 145 | — |
| 9 | inhibition (10 μM) | 68.0% | 83.8% | 16.3% | 41.4% | 0.1% |
|   | Ki (nM) | 3922 ± 465 | >10000 | — | — | — |
| 10 | inhibition (10 μM) | 40.3% | -0.3% | -3.0% | 31.9% | 110.4% |
|   | Ki (nM) | 4695 ± 262 | — | — | — | 9750.5 |

*Compound number refers to compounds listed above.

Compounds 7 and 8 showed selectivity for histamine H1 receptor, at 517±28 nM and 678±46 nM, respectively. Compound 8 was significantly active against kappa opioid receptor (3708±145 nM).

All of the seven tested compounds showed binding activity toward 5HT-2B receptor, with Ki values from 505 nM to 4695 nM (see below). The compounds show good selectivity for 5HT-2B versus other serotonin receptors, for which no significant activity was detected at 10 μM. Compound 2 showed at least a 20-fold selectivity for the 5HT-2B receptor versus the other serotonin receptors.

| Compounds | Ki (nM) vs 5-HT$_{2B}$ |
|---|---|
| 1 | 1360 ± 110 |
| 2 | 505 ± 29 |
| 5 | 1541 ± 134 |
| 7 | 1031 ± 76 |
| 8 | 1260 ± 99 |
| 9 | 3922 ± 465 |
| 10 | 4695 ± 262 |

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for treating a disorder in a mammal, the method comprising the step of administering to the mammal an effective amount of least one compound having a structure represented by a formula:

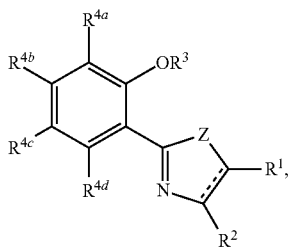

wherein ----- is an optional covalent bond, wherein valency is satisfied;
wherein Z is selected from O and S;
wherein $R^1$ is selected from hydrogen and optionally substituted C1-C6 alkyl;
wherein $R^2$ is selected from nitrile, formyl, optionally substituted heteroaryl, optionally substituted heterocycloalkyl, optionally substituted alkoxyl, optionally substituted thioalkyl, optionally substituted alkylsulfonyl, thioamido, amino-carbonyl, and alkylamine-carbonyl;
wherein $R^3$ is selected from hydrogen and optionally substituted C1-C6 alkyl;
wherein each of $R^{4a}$, $R^{4b}$, $R^{4c}$, and $R^{4d}$ is independently selected from hydrogen, halogen, hydroxyl, nitrile, nitro, thiol, formyl, optionally substituted amino, optionally substituted aryl, optionally substituted heteroaryl, optionally substituted alkoxyl, optionally substituted thioalkyl, optionally substituted alkylsulfinyl, optionally substituted alkyl sulfonyl, optionally substituted alkylamino, thioamido, amidosulfonyl, alkoxycarbonyl, carboxamide, amino-carbonyl, alkylamine-carbonyl, and optionally substituted C1-C6 alkyl;
or a pharmaceutically acceptable salt thereof,
wherein the disorder is asthma.

2. The method of claim 1, wherein the mammal is a human.

3. The method of claim 1, wherein the mammal has been diagnosed with a need for treatment of the disorder prior to the administering step.

4. The method of claim 1, wherein Z is S.

5. The method of claim 1, wherein $R^1$ is methyl.

6. The method of claim 1, wherein $R^2$ is selected from formyl, optionally substituted heteroaryl, optionally substituted heterocycloalkyl, alkoxycarbonyl, amino-carbonyl, and alkylamine-carbonyl.

7. The method of claim 1, wherein $R^2$ has a structure represented by a formula:

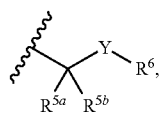

wherein Y is selected from O and S;
wherein $R^{5a}$ and $R^{5b}$ together comprise =O or =S, or wherein each of $R^{5a}$ and $R^{5b}$ is independently selected from hydrogen and optionally substituted C1-C6 alkyl;
wherein $R^6$ is selected from hydrogen, optionally substituted C1-C6 alkyl, optionally substituted aryl, optionally substituted heteroaryl, optionally substituted cycloalkyl, optionally substituted heterocycloalkyl, and optionally substituted benzyl.

8. The method of claim 1, wherein $R^3$ is hydrogen.

9. The method of claim 1, wherein the compound has a structure represented by a formula:

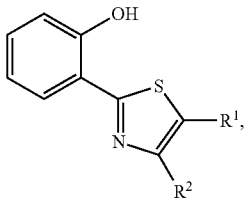

wherein R¹ is selected from hydrogen and optionally substituted C1-C6 alkyl;
wherein R² is selected from nitrile, formyl, optionally substituted heteroaryl, optionally substituted heterocycloalkyl, optionally substituted alkoxyl, optionally substituted thioalkyl, optionally substituted alkyl sulfonyl, thioamido, amino-carbonyl, and alkylamine-carbonyl;
or a pharmaceutically acceptable salt thereof.

10. The method of claim 1, wherein the compound is selected from:

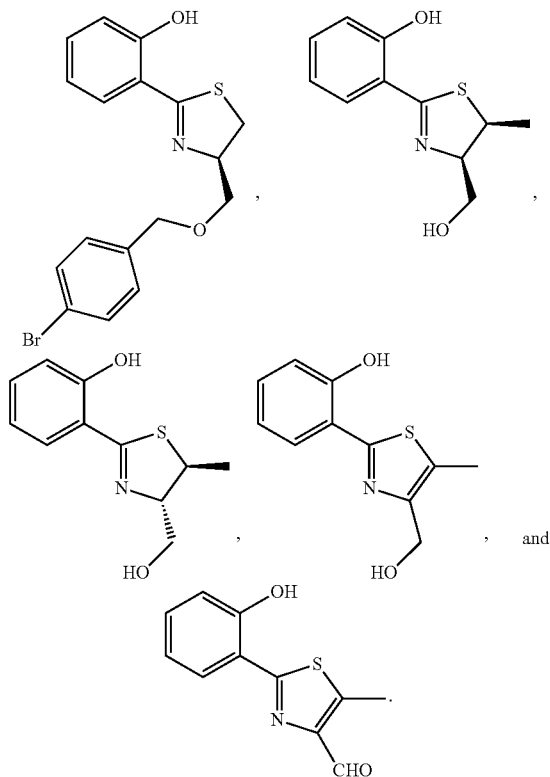

11. The method of claim 1, wherein the compound has a structure represented by a formula:

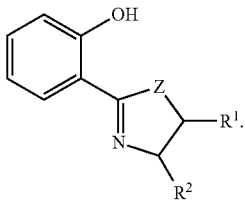

12. A method for treating a disorder in a mammal, the method comprising the step of administering to the mammal an effective amount of least one compound having a structure represented by a formula:

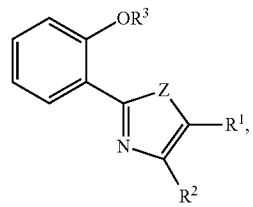

wherein Z is selected from O and S;
wherein R¹ is optionally substituted C1-C6 alkyl;
wherein R² is selected from nitrile, formyl, optionally substituted heteroaryl, optionally substituted heterocycloalkyl, optionally substituted alkoxyl, optionally substituted thioalkyl, optionally substituted alkyl sulfonyl, thioamido, carboxamide, amino-carbonyl, and alkylamine-carbonyl;
wherein R³ is selected from hydrogen and optionally substituted C1-C6 alkyl;
or a pharmaceutically acceptable salt thereof,
wherein the disorder is asthma.

13. The method of claim 12, wherein the mammal is a human.

14. The method of claim 12, wherein the mammal has been diagnosed with a need for treatment of the disorder prior to the administering step.

15. The method of claim 1, wherein Z is S.

16. The method of claim 1, wherein R¹ is methyl.

17. The method of claim 1, wherein R² is selected from formyl, optionally substituted heteroaryl, optionally substituted heterocycloalkyl, alkoxycarbonyl, carboxamide, amino-carbonyl, and alkylamine-carbonyl.

18. The method of claim 1, wherein R² has a structure represented by a formula:

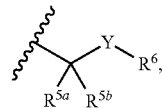

wherein Y is selected from O and S;
wherein $R^{5a}$ and $R^{5b}$ together comprise =O or =S, or wherein each of $R^{5a}$ and $R^{5b}$ is independently selected from hydrogen and optionally substituted C1-C6 alkyl;
wherein R⁶ is selected from hydrogen, optionally substituted C1-C6 alkyl, optionally substituted aryl, optionally substituted heteroaryl, optionally substituted cycloalkyl, optionally substituted heterocycloalkyl, and optionally substituted benzyl.

19. The method of claim 12, wherein R³ is hydrogen.

20. The method of claim 12, wherein the compound has a structure represented by a formula:

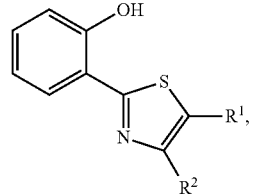

wherein R¹ is optionally substituted C1-C6 alkyl;
wherein R² is selected from nitrile, formyl, optionally substituted heteroaryl, optionally substituted heterocycloalkyl, optionally substituted alkoxyl, optionally substituted thioalkyl, optionally substituted alkylsulfonyl, thioamido, carboxamide, amino-carbonyl and alkylamine-carbonyl;
or a pharmaceutically acceptable salt thereof.

21. The method of claim 12, wherein the compound is selected from:

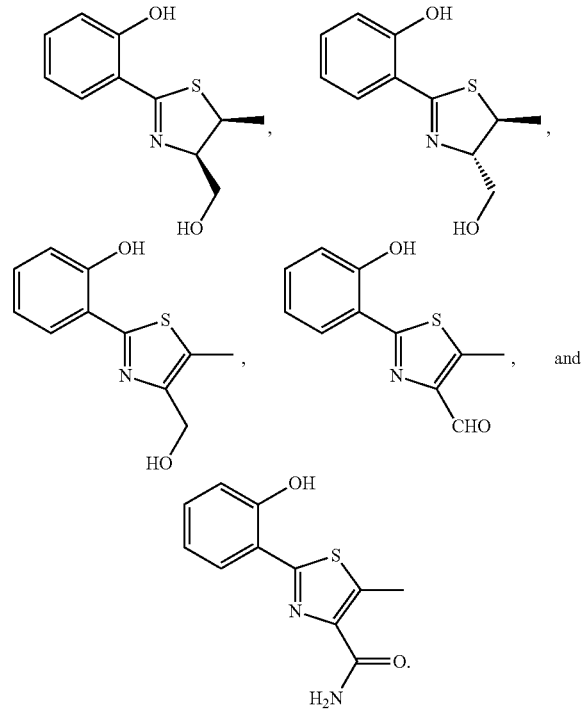

22. The method of claim 12, wherein the compound has a structure represented by a formula:

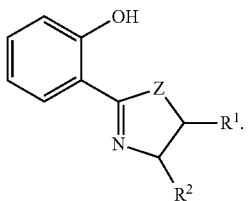

23. A method for treating a disorder in a mammal, the method comprising the step of administering to the mammal an effective amount of least one compound having a structure represented by a formula:

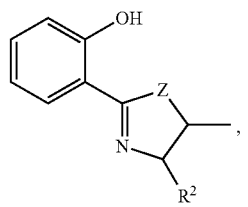

wherein Z is selected from O and S;
wherein $R^2$ is selected from nitrile, formyl, optionally substituted heteroaryl, optionally substituted heterocycloalkyl, optionally substituted alkoxyl, optionally substituted thioalkyl, optionally substituted alkyl sulfonyl, thioamido, alkoxycarbonyl, amino-carbonyl, and alkylamine-carbonyl;
or a pharmaceutically acceptable salt thereof,
wherein the disorder is asthma.

24. The method of claim 23, wherein $R^2$ is —CH$_2$OH.

* * * * *